(12) United States Patent
Olson et al.

(10) Patent No.: US 7,160,720 B2
(45) Date of Patent: Jan. 9, 2007

(54) CHAMP—A NOVEL CARDIAC HELICASE-LIKE FACTOR

(75) Inventors: Eric Olson, Dallas, TX (US); Zhi-Ping Liu, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 532 days.

(21) Appl. No.: 10/077,583

(22) Filed: Feb. 15, 2002

(65) Prior Publication Data

US 2003/0077810 A1 Apr. 24, 2003

Related U.S. Application Data

(60) Provisional application No. 60/351,713, filed on Jan. 24, 2002, provisional application No. 60/269,764, filed on Feb. 16, 2001.

(51) Int. Cl.
*C07H 21/04* (2006.01)
*C12N 15/63* (2006.01)
*C07K 14/00* (2006.01)

(52) U.S. Cl. .................................. 435/320.1; 536/23.1
(58) Field of Classification Search ............... 536/23.1; 435/320.1, 325, 70.1
See application file for complete search history.

(56) References Cited

OTHER PUBLICATIONS

Accession No. HSM801339, Feb. 18, 2000.*
Accession No. AF285604, Apr. 12, 2001.*
Acession No. AX247728, Sep. 28, 2001.*
Bork (Genome Research, 10:398-400, 2000).*
Smith et al (Nature Biotechnology 15:1222-1223, 1997).*
Brenner (TIG 15:132-133, 1999).*
Broun et al. (Science 282:1315-1317, 1998).*
Van de Loo et al. (Proc. Natl. Acad. Sci. 92:6743-6747, 1995).*
Sigmund, C.D. 2000. Arterioscler Thromb Vasc Biol.20:1425-1429.*
Wall, R.J. 1996. Theriogenology 45:57-68.*
Verma et al. (1997, Nature, vol. 389, pp. 239-242).*
GENEMBL Database Accession No. AL133068.
GENEMBL Database Accession No. AW552067.
Black and Olson, "Transcriptional control of muscle development by myocyte enhancer factor-2 (MEF2) proteins," *Annual Rev. Cell Dev. Biol.*, 14:167-196, 1998.
Chen, et al., "Evidence for regulation of transcription and replication of the human neurotropic virus JCV genome by the human S9mu)bp-2 protein in glial cells," *Gene*, 185:55-62, 1997.
Cui, et al., "Identification and characterization of genes that are required for the accelerated degradation of mRNAs containing a premature translational termination codon," *Genes Devel.*, 9:423-436, 1995.
Czaplinski, et al., "Purification and characterization of the Upf1 protein: a factor involved in translation and mRNA degradation," *RNA*, 1:610-623, 1995.

De la Crus, et al., "Undwinding RNA in *Saccharomyces cerevisiae*, DEAD-box proteins and related families," *Trends in Biochem. Sciences*, 24:192-198, 1999.
DeMarini, et al., "SEN1, a positive effector of tRNA-splicing endonuclease in *Saccharomyces cerevisiae*," *Molecular Cellular Biol.*, 12:2154-2164, 1992.
Edmondson, et al., "Mef2 gene expression marks the cardiac and skeletal muscle lineages during mouse embryogenesis," *Development*, 120:1251-1263, 1994.
Firulli, et al., "Heart and extra-embryonic mesodermal defects in mouse embryos lacking the bHLH transcription factor Hand1," *Nature Gene.*, 18:266-270, 1998.
Frey et al., "Calsarcins, a novel family of sarcomeric calcineurin-binding proteins," *Proc. Nat'l Acad. Sci. USA*, 97:14632-14637, 2000.
Gulley, et al., "Translocations of 11q13 in mantle cell lymphoma fail to disrupt the S mu bp-2 gene," *Hematopathology Molecular Hematology*, 11:1-11, 1997.
Kim, et al., "The sen1(+) gene of *Schizosaccharomyces pombe*, a homologue of budding yeast SEN1, encodes an RNA and DNA helicase," *Biochemistry*, 38:14697-14710, 1999.
Kuisk, et al., "A single MEF2 site governs desmin transcription in both heart and skeletal muscle during mouse embryogenesis," *Developmental Biology*, 174:1-13, 1996.
Leeds, et al., "The product of the yeast UPF1 gene is required for rapid turnover of mRNAs containing a premature translational termination codon," *Genes Development*, 5:2303-2314, 1991.
Lelivelt and Culbertson, "Yeast Upf proteins required for RNA surveillance affect global expression of the eyast transcriptome," *Molecular Cellular Biology*, 19:6710-6719, 1999.
Lin, et al., "Control of mouse cardiac morphogenesis and myogenesis by transcription factor MEF2C," *Science*, 276;1404-1407, 1997.
Liu and Olson, "Suppression of proliferation and cariomyocyte hypertrophy by CHAMP, a cardiac-specific RNA helicase," *Proc. Natl. Acad. USA*, 99:2043-2048, 2002.

(Continued)

*Primary Examiner*—Celine Qian
(74) *Attorney, Agent, or Firm*—Fulbright & Jaworski

(57) ABSTRACT

The present invention relates to a new polypeptide and the gene encoding therefore, said gene being regulated in cardiac tissue by the transcription factor MEF2C. This polypeptide, CHAMP (cardiac helicase activated by MEF2 protein), bears striking resemblance to a number of other helicase proteins and appears to play a role in RNA processing and transcriptional control in heart muscle. For example, CHAMP has been demonstrated to inhibit both hypertrophy of primary cardiomyocytes and proliferation of non-cardiac cells. Also disclosed are methods of using the gene and protein in drug screening and therapy, including, for example, use of the gene in gene therapy to treat cardiovascular disease.

16 Claims, 7 Drawing Sheets

OTHER PUBLICATIONS

Liu, et al., "CHAMP, a novel cardiac-specific helicase regulated by MEF2C," *Dev. Biol.*, 234:497-509, 2001.

Nakagawa, et al., "HRT1, HRT2, and HRT3: a new subclass of bHLH transcription factors marking specific cardiac, somitic, and pharyngeal arch segment," *Develop. Biol.*, 216:72-84, 1999.

Nakajima, et al., "RNA helicase A mediates association of CBP with RNA polymerase II," *Cell*, 90:1107-1112, 1997.

Nicol, et al., "Activated MEK5 induces serial assembly of sarcomeres and eccentric cardiac hypertrophy," EMBO J., 20:2757-2767, 2001.

Nozato et al., "Overexpression of cdk inhibitor p16$^{INK4a}$ by adenovirus vector inhibits cardiac hypertrophy in vitro and in vivo: a novel strategy for the gene therapy of cardiac hypertrophy," *J. Mol. Cell. Cardiol.*, 33:1493-1504, 2001.

Ross, et al., "An HF-1a/HF-1b/MEF-2 combinatorial element confers cardiac ventricular specificity and established an anterior-posterior gradient of expression," *Development*, 122:1799-1809, 1996.

Sebastiani, et al., "Localization of the Catf1 transcription factor gene to mouse chromosome 19," *Mammalian Genome*, 6:147-148, 1995.

Siomi and Dreyfuss, "RNA-binding proteins as regulators of gene expression," *Curr. Opin. Genet. Dev.*, 7:345-353, 1997.

Weng, et al., "Genetic and biochemical characterization of mutations in the ATPase and helicase regions of the Upf1 protein," *Molecular Cellular Biol.*, 16:5477-5490, 1996.

Zhang, et al., "Sµbp-2 represses the Epstein-Barr virus lytic switch promoter," *Virology*, 255:160-170, 1999.

\* cited by examiner

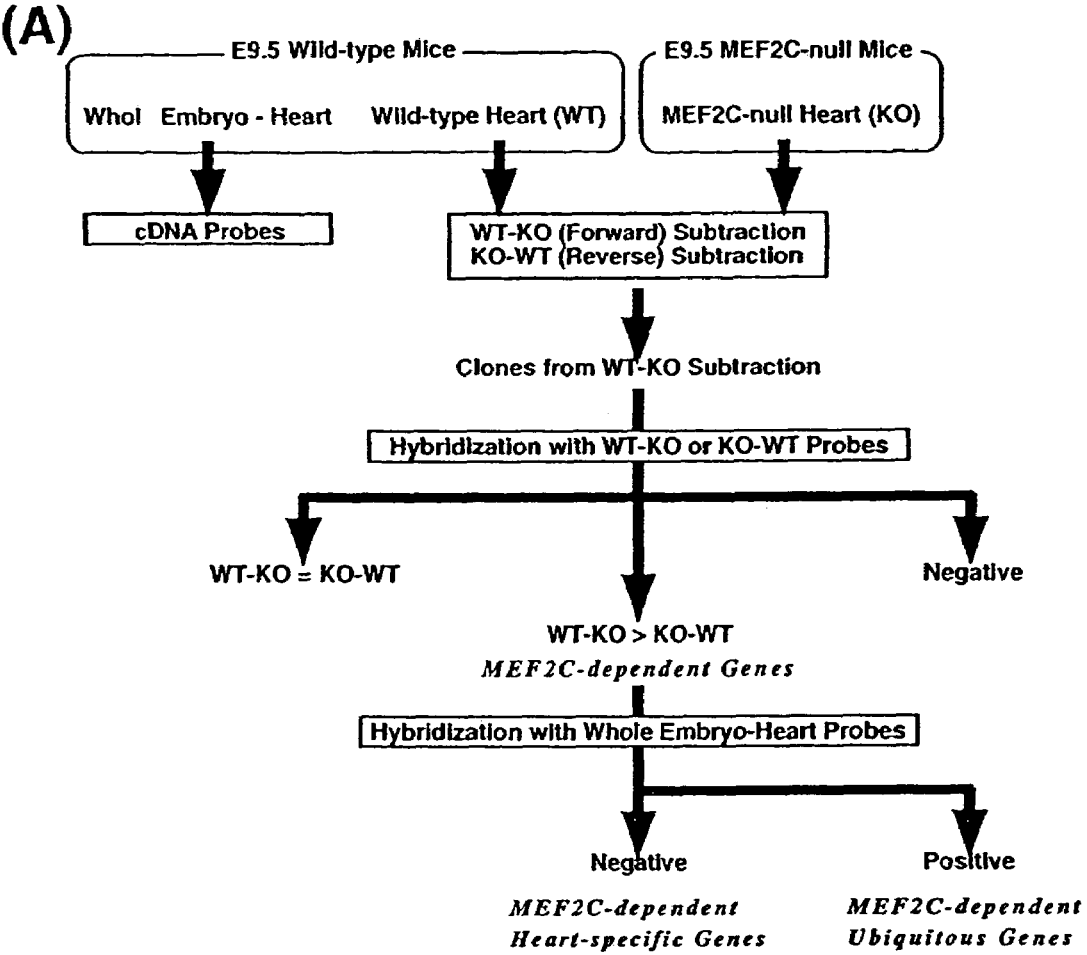
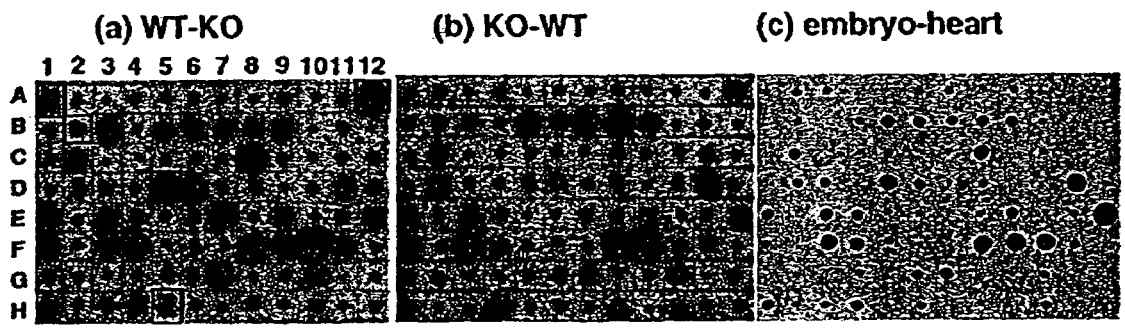
FIG. 1A–B

 
MEF2C +/+    MEF2C -/-
FIG. 2

(A)

```
GATAAGGAGTTCTTCAACCCAGTGCTCAATGAAAACCAAAAGCTGACCGTGAGGAGGATCCTGAGTGGCGACTGCCGGCCTCTCCCATAT 90
 D  K  E  P  F  N  P  V  L  N  E  N  Q  K  L  T  V  R  R  I  L  S  G  D  C  R  P  L  P  Y

ATCCCTTTTGGACCTCCGGGAACTGGAAACACTGTGACTATAATCGAGGCTGTTTTGCAGGTACATTATGCTTTGCCGGACAGTCGGATT 180
 I  P  P  G  P  P  G  T  G  K  T  V  T  I  I  E  A  V  L  Q  V  H  Y  A  L  P  D  S  R  I
         ─────────────────
          I

TTGGTCTGCGCTCCTTCCAACAGTGCTGCTGACCTTGTGTGTTTGCCGACTTCATCAGAGCAAGGTGCTGAAGCCAGCCTGCCATGGTCCGG 270
 L  V  C  A  P  S  N  S  A  A  D  L  V  C  L  R  L  H  E  S  K  V  L  K  P  A  A  H  V  R
 ─────────────
      Ia

GTGAATGCCACCTGCAGATTTGAAGAGACTATTATTGATGCCATCAAACCGTATTGCAGAGATGGAGAAGATATCTGGAGAGCCTCACGC 360
 V  N  A  T  C  R  F  E  E  T  I  I  D  A  I  K  P  Y  C  R  D  G  E  D  I  W  R  A  S  R

TTCAGGATAATAATCACTACATGTAGCAGTGCAGGACTGTTTTACCAAATAGGAGTGAGAGTTGGATACTTCACACATGTATTTGTGGAC 450
 F  R  I  I  I  T  T  C  S  S  A  G  L  F  Y  Q  I  G  V  R  V  G  Y  F  T  H  V  F  V  D

GAGGCAGGACAGGCAAGTGAGCCAGAATGCCTTATTCCTTTGGGACTGATTTCAGACATCAATGGCCAGATCGTGCTTGCTGGAGACCCC 540
 E  A  G  Q  A  S  E  P  E  C  L  I  P  L  G  L  I  S  D  I  N  G  Q  I  V  L  A  G  D  P
 ─────────                                                                        ──────
     II                                                                              III

ATGCAGCTCGGCCCAGTCATCAAGTCCAGGCTGGCCATGGCCTATGGGTTGAATGTGTCCATGTTGGAGAGGCTGATGTCCAGACCAGCG 630
 M  Q  L  G  P  V  I  K  S  R  L  A  M  A  Y  G  L  N  V  S  M  L  E  R  L  M  S  R  P  A

TACCTGAGAGACGAAAATGCCTTTGGCGCTTGCGGTGCATATAACCCATTGTTGGTCACAAAGCTTGTGAAGAACTACAGGTCCCACTCG 720
 Y  L  R  D  E  N  A  F  G  A  C  G  A  Y  N  P  L  L  V  T  K  L  V  K  N  Y  R  S  H  S
                                                            ──────────────────
                                                                    IV

GCTCTGCTGGCACTGCCCTCACGCCTGTTCTACCATAGGGAGCTTGAGGTCTGTGCTGATCCCAAAGTAGTGACTTCACTGCTGGGCTGG 810
 A  L  L  A  L  P  S  R  L  F  Y  H  R  E  L  E  V  C  A  D  P  K  V  V  T  S  L  L  G  W

GAGAAGCTGCCCAGAAAAGGCTTTCCCTCTCATCTTCCATGGAGTGAGGGGGAACGAGGCTCGTGAAGGGAGAAGCCCATCGTGGTTCAGC 900
 E  K  L  P  R  K  G  F  P  L  I  F  H  G  V  R  G  N  E  A  R  E  G  R  S  P  S  W  F  S

CCAGCCGAGGCTGTCCAGGTCATGCGCTACTGTTGCCTCTTGGCCCGGAGTGTCTCCAGTCAAGTGTCTTCCAAGGATATAGGTGTCATC 990
 P  A  E  A  V  Q  V  M  R  Y  C  C  L  L  A  R  S  V  S  S  Q  V  S  S  K  D  I  G  V  I

ACACCCTATCGGAACCAGGTGGAAAAAAATAAAAATCCTTCTGCGAAATGTGGATTTGACTGACATAAAGGTTGGCTCGGTAGAGGAGTTC 1080
 T  P  Y  R  Q  V  E  K  I  K  I  L  L  R  N  V  D  L  T  D  I  K  V  G  S  V  E  E  F
                                                                              ─────────
                                                                                  V

CAGGGACAAGAGTACCTGGTCATCGTCATCTCCACTGTGCGGTCAAATGAAGATAGATTTGAAGATGACCGTTATTTTTTGGGTTTCTTG 1170
 Q  G  Q  E  Y  L  V  I  V  I  S  T  V  R  S  N  E  D  R  P  E  D  D  R  Y  F  L  G  F  L

TCCAATTCAAAAAGATTTAATGTTGCAATCACAAGACCCAAAGCACTGCTGATCATTCTGGGAAACCCTCATGTGCTTGTCAGAGATCCC 1260
 S  N  S  K  R  F  N  V  A  I  T  R  P  K  A  L  L  I  I  L  G  N  P  H  V  L  V  R  D  P
     ───────────────────────
                VI

TGTTTTGGAGCGCTGCTAGAATACAGTGTTAGCAATGGTGTCTACACAGGGTGTGATCTGCCTCCTGAACTCCAGGCTCTCCAAAAGTGA 1350
 C  F  G  A  L  L  E  Y  S  V  S  N  G  V  Y  T  G  C  D  L  P  P  E  L  Q  A  L  Q  K  *

GCACTCCAGTCCACTTCCTAAAAGGTAAAGCACCGTGGAGGAAAGAGTGTGGCCTCCACGTGTTCACCTTAAGCAGGCTGTGGCTAGACAG
CTGTGCCAGGACCTGTGGACATGGTGGAGTCTGCTACAACAGGGAGCCATTGAGCCTCACCCTATGGGCATTAGTCCAGCCATGCTTCA
GTCTTCTGTGACTCCTGCGGCTTCCTGGTCTCAAGACTGAAATGTTGGTATGCATGGGACCACTGAGTCAGCTGGGCTGCTCCTGCTTCCT
TGGACTGACCTTGGTTCCTAACAGTTAGTTTCTGCCTGTGGGCAATCACTGCCACTACACTCCCCCA AATAA CACTTCCATAACCCCAG
AAAAAAAAAA-1720
```

CHAMP—A NOVEL CARDIAC HELICASE-LIKE FACTOR

This application claims the benefit of priority to provisional applications U.S. Ser. No. 60/269,764, filed Feb. 16, 2001 and 60/351,713, filed Jan. 24, 2002, both which are hereby incorporated by reference in their entirety.

The government may own rights in the present invention pursuant to grant number RO1HL61544 from the National Institute of Health.

BACKGROUND OF THE INVENTION

1. Field of the Invention

The present invention relates generally to the fields of developmental biology and molecular biology. More particularly, it concerns an anti-hypertrophic helicase expressed specifically in heart tissue.

2. Description of Related Art

It has been reported by the American Heart Association (1997, Statistical Supplement), that almost 60 million people in the United States suffer from one or more cardiovascular diseases. Cardiovascular diseases are responsible for almost a million deaths annually in the United States representing over 40% of all deaths. Coronary heart disease, characterized by atherosclerotic narrowing of the coronary arteries, resulted in death for almost half a million people in 1997 and is the single leading cause of death in America today. This year it is estimated more than one million Americans will have a new or recurrent coronary attack, and more than 40 percent of the people experiencing these attacks will die of them. Myocardial infarction (MI), commonly referred to as heart attack, is a leading cause of mortality with 30% being fatal in the first months following the attack. Myocardial infarctions result from narrowed or blocked coronary arteries in the heart which starves the heart of needed nutrients and oxygen.

Another form of heart disease, congestive heart failure, represents the most frequent non-elective cause of hospitalization in the U.S. Each year, close to half a million patients are diagnosed with CHF, which is defined as abnormal heart function resulting in inadequate cardiac output for metabolic needs (Braunwald, 1988). Symptoms of CHF include breathlessness, fatigue, weakness, leg swelling, and exercise intolerance. On physical examination, patients with heart failure tend to have elevations in heart and respiratory rates, rales (an indication of fluid in the lungs), edema, jugular venous distension, and, in general, enlarged hearts, indicative of cardiac hypertrophy. Although medical therapy can initially attenuate the symptoms of heart failure (e.g., edema, breathlessness and fluid in the lungs), and in some cases prolong life, the prognosis in this disease, even with medical treatment, is grim (see, e.g., Baughman, 1995). Once symptoms of heart failure are moderately severe, the prognosis is worse than most cancers in that 50% of such patients may die within 2 years (Braunwald, 1988).

Cardiac hypertrophy is an adaptive response of the heart to virtually all forms of cardiac disease, including those arising from hypertension, mechanical load, myocardial infarction, cardiac arrythmias, endocrine disorders and genetic mutations in cardiac contractile protein genes. While the hypertrophic response is initially a compensatory mechanism that augments cardiac output, sustained hypertrophy can lead to dilated cardiomyopathy, heart failure, and sudden death. In the United States, approximately half a million individuals are diagnosed with heart failure each year, with a mortality rate approaching 50%. Because cardiac hypertrophy can be viewed as an aberration in heart growth and development, a relevant inquiry may be made into the molecular basis of cardiac tissue specification and differentiation.

The heart is the first organ to form during mammalian embryogenesis (Olson and Srivastava, 1996; Fishman and Olson, 1997). Formation of the heart involves commitment of cells from the anterior lateral mesoderm to a cardiogenic fate in response to inductive cues from adjacent endoderm. During mouse development, cardiac precursor cells are localized to a region known as the cardiac crescent, which spans the anterior ventral midline of the embryo. These cells migrate ventrolaterally to form a linear heart tube at E8.0. The linear heart tube is patterned along its anterior-posterior axis into segments that give rise to the atria, left ventricle, right ventricle, and outflow tract. Rightward looping of the heart tube is essential for orientation of the right and left ventricular chambers and alignment of the heart with the inflow and outflow tracts. Later events of chamber maturation, septation, endocardial development, and valvulogenesis give rise to the mature multi-chambered heart.

Several mouse and zebrafish mutants exhibit specific defects in cardiac looping, ventricular morphogenesis and chamber maturation (Fishman and Olson, 1997). The phenotypes of these mutants, which often result in ablation of specific segments of the heart, have led to the notion that distinct transcriptional networks control formation of different cardiac compartments. Many of the genes shown to be required for these morphogenetic events encode transcription factors, but the target genes that mediate the actions of these factors are largely unknown.

The basic helix-loop-helix (bHLH) transcription factors, dHAND and eHAND, are expressed specifically in the developing right and left ventricular chambers, respectively. dHAND is required for formation of the left ventricle of the heart (Srivastava et al., 1995, 1997; Firulli et al., 1998; Srivastava, 1999). Similarly, the cardiac homeodomain protein Nkx2.5 is required for looping morphogenesis (Lyons, 1995), and is a regulator of eHAND expression (Biben and Harvey, 1997). The zinc finger transcription factors GATA-4 in mice and GATA-5 in zebrafish have also been shown to be required for ventral morphogenesis and formation of the linear heart tube (Kuo et al., 1997; Molkentin et al., 1997; Reiter et al., 1999).

Recently, the inventors showed that the MADS-box transcription factor MEF2C, which is expressed throughout the linear, looping, and multichambered heart, is required for looping morphogenesis and right ventricular development (Lin et al., 1997). There are four MEF2 genes in vertebrates, MEF2A, -B, -C, and -D, which are expressed in overlapping patterns in developing muscle and neural cell lineages, and at lower levels in other cell types (Black and Olson, 1998). MEF2 factors bind an A/T-rich sequence in the control regions of numerous skeletal, cardiac, and smooth muscle-specific genes. Functional redundancy among the vertebrate MEF2 genes has precluded a complete analysis of MEF2 function in the mouse. However, in *Drosophila*, there is only one MEF2 gene, which, like the vertebrate MEF2 genes, is expressed in developing muscle cell lineages (Lilly et al., 1994; Nguyen et al., 1994). In *Drosophila* embryos lacking MEF2, skeletal, cardiac, and visceral myoblasts are properly specified and positioned, but they cannot differentiate, and there are severe abnormalities in morphogenesis of the visceral musculature (Lilly et al., 1995; Ranganayakulu et al., 1995; Bour, 1905). This severe muscle phenotype suggests that MEF2 acts in myoblasts to activate downstream muscle-specific genes involved in differentiation and morphogenesis.

In addition to regulating muscle-specific genes, MEF2 has been implicated in activation of growth factor-inducible and stress-responsive genes (Naya and Olson, 1999). The c-jun promoter, for example, contains a MEF2 site that confers serum and EGF-inducibility (Han et al., 1992, 1995). Signal-dependent activation of MEF2-targeted genes has been shown to involve MAP kinase (Zhao et al., 1999), CaM kinase (Passier et al., 2000), and calcineurin (Chin et al., 1998; Mao et al., 1999). The Notch signaling pathway has been shown to inhibit MEF2 activity in vertebrates and *Drosophila* (Wilson-Rawls et al., 1999). However, relatively little is know about the targets of MEF2 activation.

SUMMARY OF THE INVENTION

In one aspect, the present invention provides an isolated CHAMP polypeptide, in particular a CHAMP polypeptide comprising the amino acid sequence of SEQ ID NO:2 or 8. Also provided are polynucleotides encoding a CHAMP polypeptide comprising an amino acid sequence of SEQ ID NO:2, 4, 6 or 8. By way of illustration, the polynucleotide may have the nucleic acid sequence of SEQ ID NO:1, 3, 5 or 7. The polynucleotide may further comprise a promoter operable in eukaryotic cells, for example, a promoter heterologous to the natural sequence of SEQ ID NO: 1, 3, 5 or 7. Exemplary promoters include hsp68, SV40, CMV, MKC, GAL4$_{UAS}$, HSV, Hef-1α and β-actin. Alternativley, the promoter may be tissue specific promoter, for example, muscle or cardiac specific.

In another embodiment, there is provided a nucleic acid of 15 to about 2000 base pairs comprising from about 15, 20, 25, 30, 40, 50, 100, 150, 250, 500, 1000, 2000 or more contiguous base pairs of SEQ ID NO:1, 3, 5 or 7, or the complement thereof. Also provided is a peptide comprising 10, 15, 20, 25, 30, 40, 50 or more contiguous amino acids of SEQ ID NO:2, 4, 6 or 8.

In yet another embodiment, there is provided an expression cassette comprising a polynucleotide encoding a CHAMP polypeptide, for example a CHAMP polypeptide having the sequence of SEQ ID NO:2, 4, 6 or 8. In preferred embodiments the polynucleotide within the expression cassette is under the control of a promoter operable in eukaryotic cells. The promoter may be heterologous to the coding sequence and may be a ubiquitous promoter, for example a CMV, Hef-1α or RSV promoter or may be a tissue specific promoter, for example, a muscle specific promoter, such as a cardiac specific promoter. Exemplary tissue specific promoters include myosin light chain-2 promoter, α actin promoter, troponin 1 promoter, Na$^+$/Ca$^{2+}$ exchanger promoter, dystrophin promoter, creatine kinase promoter, α7 integrin promoter, brain natriuretic peptide promoter, αB-crystallin/small heat shock protein promoter, α myosin heavy chain promoter and atrial natriuretic factor promoter. The promoter may be a constitutive or an inducible promoter.

The expression cassette may be comprised within a viral vector, for example, a retroviral vector, an adenoviral vector, and adeno-associated viral vector, a vaccinia viral vector, a herpesviral vector, a polyoma viral construct or a Sindbis viral vector. Alternatively, the expression cassette may be comprised within a non-viral vector, for example a lipid based vector. The expression cassette may further comprise various regulatory sequences, such as for example, an enhancer sequence, a polyadenylation signal or the like. The expression cassette may comprise a one or more additional polynucleotides encoding one or more additional polypeptides, under the control of the same or a different promoter.

In still another embodiment, there is provided a method of screening for modulators of CHAMP expression comprising (a) providing a cell in which a CHAMP promoter directs the expression of a polypeptide; (b) contacting said cell with a candidate modulator; and (c) measuring the effect of said candidate modulator on said polypeptide, wherein a difference in expression of said polypeptide, as compared to an untreated cell, indicates that said candidate modulator is a modulator of CHAMP expression. Measuring may comprise Northern analysis, PCR, RT-PCR, or immunologic detection of CHAMP (including ELISA and immunohistochemistry). The cell may be located in an animal. The cell type may be a myocyte, or more specifically, a cardiomyocyte. The method may further comprise screening for modulation of expression of a second MEF2-regulated gene. The modulator may increase or decrease expression. The polypeptide may be CHAMP or a screenable marker polypeptide.

In still yet another embodiment, there is provided a method of screening for modulators of CHAMP helicase activity comprising (a) providing an active CHAMP preparation; (b) contacting said CHAMP preparation with a candidate modulator; and (c) measuring the helicase activity of said CHAMP preparation, wherein a difference in helicase activity of said CHAMP preparation, as compared to an untreated CHAMP preparation, indicates that said candidate modulator is a modulator of CHAMP helicase activity.

Further embodiments include a method of screening for an inhibitor of MEF2 transactivation comprising (a) providing a cell in which a CHAMP promoter directs the expression of a polypeptide; (b) contacting said cell with a candidate modulator; and (c) measuring the effect of said candidate modulator on said polypeptide, wherein a difference in expression of said polypeptide, as compared to an untreated cell, indicates that said candidate modulator is a modulator of MEF2 transactivation. The cell may be a myocyte, for example, a cardiomyocyte. The polypeptide may be a CHAMP or a screenable marker polypeptide.

Also provided is a method of producing a CHAMP polypeptide in a cell comprising (a) transforming a cell with an expression cassette comprising a nucleic acid encoding CHAMP under the control of a promoter active in said cell; (b) culturing said cell under conditions suitable for expression of CHAMP. The cell may be, for example a cardiomyocyte or a fibroblast, such as a cardiac fibroblast. The cell may be located in an animal. The transforming step may comprise infection with a viral vector, such as an adenoviral construct, a retroviral construct, an adeno-associated viral construct, a herpesviral construct, a vaccinia viral construct, a polyoma viral construct or a Sindbis viral vector. The transforming step may also comprise contacting the cell with a liposome comprising the expression cassette, electroporation, calcium phosphate precipitation or protoplast fusion. The cell may be a prokaryotic or eukaryotic cell. The method may further comprise the step of purifying said CHAMP polypeptide away from other cellular components.

In other embodiments, there are provided a non-human transgenic animal comprising a selectable or screenable marker protein under the control of a CHAMP promoter; a non-human transgenic animal comprising a CHAMP encoding nucleic acid under the control of an inducible promoter; a non-human transgenic animal comprising a CHAMP encoding nucleic acid under the control of a constitutive promoter, and a non-human transgenic animal lacking at least one CHAMP allele, or both.

In yet other embodiments, methods of treating heart disease comprising enhancing CHAMP function in heart cells of a subject are provided. In one aspect, heart disease is treated employing gene therapy methods whereby a polynucleotide encoding a CHAMP polypeptide is delivered to a subject's heart wherein it is expressed and one or more symptoms of cardiovascular disease are ameliorated or prevented. By way of illustration, a gene delivery vehicle, such as a viral or non-viral vector, comprising a polynucleotide encoding a CHAMP polypeptide may be administered to the heart of a patient, for example, to inhibit hypertrophy of cardiomyocytes and/or to suppress proliferation of other cell types, such as, for example, cardiac fibroblasts. Such methods may be employed, for example, to treat myocardial infarction, heart failure, dilated cardiomyopathy or other heart disease. In another aspect, CHAMP function may be enhanced by administration of a modulator of CHAMP expression, for example a transactivator such as MEF2. Such methods may be conducted ex vivo, but are preferably performed in vivo.

In additional embodiments, there are provided:
a method of producing a modulator of CHAMP expression comprising (a) providing a cell in which a CHAMP promoter directs the expression of a polypeptide; (b) contacting said cell with a candidate modulator; (c) measuring the effect of said candidate modulator on said polypeptide, wherein a difference in expression of said polypeptide, as compared to an untreated cell, indicates that said candidate modulator is a modulator of CHAMP expression; and (d) producing said modulator;
a method of producing a modulator of CHAMP helicase activity comprising (a) providing an active CHAMP preparation; (b) contacting said CHAMP preparation with a candidate modulator; (c) measuring the helicase activity of said CHAMP preparation, wherein a difference in helicase activity of said CHAMP preparation, as compared to an untreated CHAMP preparation, indicates that said candidate modulator is a modulator of CHAMP helicase activity; and (d) producing said modulator; and
a method of producing an inhibitor of MEF2 transactivation comprising (a) providing a cell in which a CHAMP promoter directs the expression of a polypeptide; (b) contacting said cell with a candidate modulator; (c) measuring the effect of said candidate modulator on said polypeptide, wherein a difference in expression of said polypeptide, as compared to an untreated cell, indicates that said candidate modulator is a modulator of MEF2 transactivation; and (d) producing said modulator.

Also provided are modulator identified according to each of the preceding methods.

There also are provided an antibody that binds immunologically to CHAMP, a polyclonal antibody preparation of antibodies that bind immunologically to CHAMP, and a hybridoma cell that produces a monoclonal antibody that binds immunologically to CHAMP.

In other embodiments, there are provided a method of treating cardiac hypertrophy comprising increasing CHAMP activity in heart cells of a subject; a method of preventing cardiac hypertrophy comprising increasing CHAMP activity in heart cells of a subject; a method of inhibiting progression of cardiac hypertrophy comprising increasing CHAMP activity in heart cells of a subject; a method of treating heart failure comprising increasing CHAMP activity in heart cells of a subject; a method of inhibiting progression of heart failure comprising increasing CHAMP activity in heart cells of a subject; a method of increasing exercise tolerance in a subject with heart failure or cardiac hypertrophy comprising increasing CHAMP activity in heart cells of a subject; a method of reducing hospitalization in a subject with heart failure or cardiac hypertrophy comprising increasing CHAMP activity in heart cells of a subject; a method of improving quality of life in a subject with heart failure or cardiac hypertrophy comprising increasing CHAMP activity in heart cells of a subject; a method of decreasing morbidity in a subject with heart failure or cardiac hypertrophy comprising increasing CHAMP activity in heart cells of a subject; and a method of decreasing mortality in a subject with heart failure or cardiac hypertrophy comprising increasing CHAMP activity in heart cells of a subject. Methods for increasing CHAMP activity include, in particular, various forms of CHAMP gene transfer, as described herein, including, for example the use of viral vectors with muscle-specific promoters.

Further provided herein is a method of enhancing cardiac function in a mammal comprising delivering a nucleic acid encoding a CHAMP polypeptide to the heart of the mammal, whereby the nucleic acid is expressed in the heart and cardiac function is enhanced. In one aspect, the nucleic acid encodes a CHAMP polypeptide comprising the amino acid sequence of SEQ ID NO:2 or 8. In a preferred embodiment, the nucleic acid is contained within a vector, such as a viral vector, which is delivered into the heart of the mammal, for example via direct injection into the heart muscle or via catheter inserted into the lumen of a vessel supplying blood to the heart.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A–B—Subtractive hybridization and differential array analysis to identify MEF2C-dependent genes. FIG. 1A: Schematic diagram of the cDNA subtraction scheme used to identify MEF2C-dependent genes. RNA was isolated from heart tubes from E9.0–9.5 wild-type (WT) and MEF2C mutant (KO) embryos and whole embryos without the heart and used for cDNA synthesis. Forward subtraction (WT–KO) and reverse subtraction (KO–WT) were performed and clones from the forward subtraction were isolated. FIG. 1B: Exemplary differential screen analysis of cDNA arrays obtained from subtractive hybridization. The cDNA fragments from subtractive cloning were subcloned into the pCRII-TOPO cloning vector. The colony PCR products were dot-blotted on duplicate filters, and probed with $^{32}$P-labeled cDNAs from the forward (panel a) and reverse subtractions (panel b). To identify potential heart-specific clones, the duplicate filters were subsequently stripped and reprobed with $^{32}$P-labeled cDNA probes from E9.0 embryos without the heart (panel c). Of the 1,000 clones arrayed, approximately 169 showed higher expression in wild-type as compared to MEF2C mutant heart tubes. Representative clones highlighted in brackets are: A1: calsequestrin; A12, MLC-2; B2, novel; D5, ATPase subunit 6; and H5, R15-C5 (CHAMP).

FIG. 2—R15-C5 expression in wild-type and MEF2C mutant embryos. Mice heterozygous for the MEF2C-null mutation were mated and homozygous-null and wild-type littermates were recovered at E8.0. Expression of R15-C5 (CHAMP) was analyzed by whole-mount in situ hybridization. R15-C5 was specifically expressed in the heart tube of wild-type embryos (left). Expression was not detected in the MEF2Cnull littermate (right).

FIG. 4A: The 1.7 kb CHAMP cDNA contains an ORF of 449 amino acids, a 370 bp 3'UTR and a putative polyadenylation signal (boxed) (SEQ ID NOS:9 and 10). The putative CHAMP protein contains seven motifs that are conserved among members of the RNA helicase Superfamily (underlined). FIG. 4B: Schematic drawing of the common central core region of RNA helicase superfamily 1. FIG. 4C: The conserved seven motifs of CHAMP are shown aligned with similar motifs in RNA helicase SFI members: yeast Upf1p, Sen1p, and Hcs1p, and murine Smubp-2. The number of intervening amino acid residues between the motifs, and of N- and C-terminal sequences flaking the central region, are in parentheses. The conserved functional motifs include an ATPase motif (1, 1a and II), helicase motif (III), and RNA binding motif (VI) (SEQ ID NOS:11–15).

FIG. 5A: E8.0, late cardiac crescent stage embryos where the two bilateral heart primordia have fused at the central midline. CHAMP is expressed in an anterior-posterior gradient in the heart tube. FIG. 5B: E9.5, looping heart stage embryos. FIG. 5C: Transverse vibratome section of embryos shown in FIG. 5B. CHAMP is specifically expressed in the right and left ventricles. FIG. 5D: Transverse section through the heart of E15.5 embryo. CHAMP is expressed in a heart-restricted manner within the myocardial cells, with highest expression in the ventricles and low expression in the atria.

DESCRIPTION OF ILLUSTRATIVE EMBODIMENTS

Figure 3:
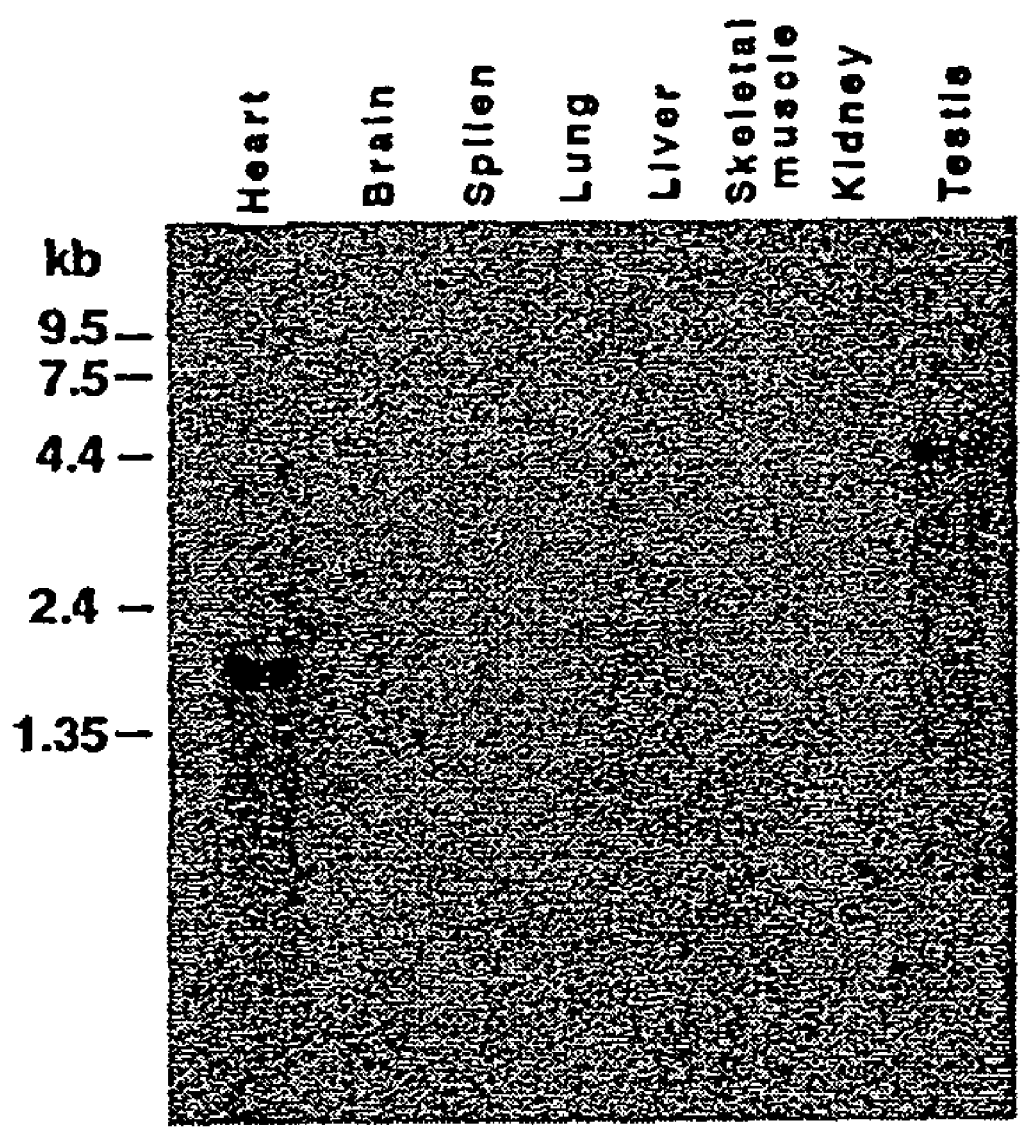
FIG. 3—Northern analysis of CHAMP RNA expression. CHAMP transcripts were detected by Northern analysis of RNA from the indicated adult mouse tissues. A single transcript of about 1.8 kb was detected in adult heart and a larger and less abundant transcript of about 4.4 kb was detected in testis.

As discussed above, heart disease and its manifestations, including coronary artery disease, myocardial infarction, congestive heart failure and cardiac hypertrophy, is a major health risk in the United States today. The cost to diagnose, treat and support patients suffering from these diseases is well into the billions of dollars. Two particularly severe manifestations of heart disease are myocardial infarction and cardiac hypertrophy. With respect to myocardial infarction, typically an acute thrombotic coronary occlusion occurs in a coronary artery as a result of atherosclerosis and causes myocardial cell death. Because cardiomyocytes, the heart muscle cells, are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic. With respect to cardiac hypertrophy, one theory regards this as a disease that resembles aberrant development and, as such, raises the question of whether developmental signals in the heart can contribute to hypertrophic disease. One of the important regulators of gene transcription in the heart, MEF2, provides an attractive tool and target for research in this regard.

The inventors have described herein a novel cardiac helicase-like factor designated as CHAMP (cardiac helicase activated by MEF2 protein). The CHAMP protein contains seven conserved motifs bearing a striking resemblance to RNA helicases involved in RNA processing, and to enhancer binding factors involved in tissue transcription. CHAMP is expressed in cardiomyocytes from the linear tube stage (E8.0) to adulthood. Thus, CHAMP was predicted to play an important role in cardiac differentiation, proliferation and development.

The inventors now show that ectopic expression of CHAMP inhibits proliferation of HeLa cells and blocks cell cycle entry of serum-stimulated NIH-3T3 cells. Further, it is shown that overexpression of CHAMP in primary neonatal cardiomyocytes blocks hypertrophic growth and the induction of fetal genes in response to stimulation by serum and phenylephrine, but does not prevent sarcomere organization or early mitogenic signaling events including activation of extracellular signal-regulated kinases or upregulation of c-fos. Inhibition of cardiomyocyte hypertrophy by CHAMP requires the conserved ATPase domain and is accompanied by up-regulation of the cyclin-dependent protein kinase inhibitor $p_{21}^{CIP1}$. These findings indicate that the presently described novel cardiac-specific CHAMP protein suppresses cardiomyocyte hypertrophy and cell cycle progression and suggest that CHAMP may suppress these processes through the regulation of $p21^{CIP1}$.

I. MEF2 AND CARDIAC GENE REGULATION

Based on the presence of MEF2 binding sites in the control regions of numerous muscle structural genes (Black and Olson, 1998), the inventors anticipated that specific genes controlled by MEF2 could be identified using a screen of differential analysis combined with subtraction hybridization of wildtype versus MEF2C-null heart tissue. As stated above, the genes identified by this method fell into four classes: muscle genes; genes encoding enzymes involved in electron transport and/or energy production; stress and growth related genes; and novel genes not yet classified. The subtraction hybridization method employed by the inventors (and described in detail elsewhere herein) was not completely saturating and thus did not identify all genes down regulated in the hearts of MEF2C mutants. However, several differentially expressed genes were identified multiple independent times thus providing confidence with respect to the MEF2C dependence of those genes that were identified.

Several of the MEF2 dependent muscle genes identified by the inventors have been shown to be direct targets for MEF2. However, others appear to be indirect targets. By way of illustration, MEF2C has been shown to be required for expression of the SM22 promoter in the developing heart (Lin et al., 1997), but this promoter is regulated by serum response factor (SRF) and does not contain a MEF2 site. Thus, MEF2 may regulate some muscle genes indirectly, for example via SRF. Exemplary MEF2C dependent muscle genes include myosin light chain 2, slow skeletal muscle troponin 1, titin, vascular smooth muscle α actin, cTnT, calsequestirn, SERCA Na+/Ca2+ exchanger, muscle LIM protein and MLC-3.

II. CHAMP, A CARDIAC-SPECIFIC HELICASE-LIKE FACTOR DEPENDENT ON MEF2C

Among the several MEF2C-dependent genes down-regulated in the heart tube of MEF2C mutants, the inventors herein have discovered a novel cardiac-restricted gene encoding a putative helicase which the inventors have termed CHAMP (cardiac helicase activated by MEF2C protein). CHAMP shares homology to RNA helicase superfamily I and its expression is restricted to the heart throughout embryonic and postnatal development, with the exception of an alternative transcript expressed at a low level in the testis.

Consistent with the conclusion that CHAMP expression is dependent on MEF2C, CHAMP transcripts were not detected until E8.0, the linear heart tube stage, a half-day after MEF2C is first expressed in the cardiac crescent (Edmondson et al., 1994). CHAMP appears to be expressed in an anterior-posterior gradient along the heart tube at E8.0, an expression pattern similar to those of MLC-2v and desmin transgenes, which require MEF2 binding sites for expression (Ross et al., 1996; Kuisk et al., 1996). Since CHAMP is expressed specifically in the embryonic heart when it is poised to undergo looping, it may be involved in spatial signaling for this morphogenic event.

CHAMP appears to be most closely related to members of RNA helicase superfamily I which includes yeast Upflp, Senlp, DNA helicase Hcslp, and murine Smubp-2. The biological functions of this RNA helicase superfamily are diverse. Members are involved in DNA replication, repair, and recombination, and RNA splicing, transcription, and translation (de la Cruz et al., 1999). Upflp is required for nonsense-mediated mRNA decay to limit the accumulation of aberrant proteins that arise through errors in gene expression such as inefficient splicing and premature termination of translation (Leeds et al., 1991; Cui et al., 1995). Upf proteins are also required to control the accumulation of a large number of mRNAs (Lelivelt et. al, 1999). Senlp is required for tRNA splicing and has been postulated to be involed in biosynthesis and processing of other RNAs such as rRNA and small nuclear and nucleolar RNAs (DeMarini et al., 1992; Kim et al., 1999). Hcs I p is a DNA helicase required for DNA replication and Smubp-2 is a transcription factor (Chen et al., 1997; Sebastiani et al., 1995). It has been shown that Smubp-2 binds two 12-o-tetracanoylphorbol-13-acetate-responsive elements in the Epstein-Barr virus immediate-early BZLF1 promoter (Gulley et al., 1997). Overexpression of Smubp-2 in B lymphocytes represses the BZLF1 gene promoter, possibly by disruption of a functional TBP-TFIIA-TATA box complex (Zhang et al., 1999). The rat homolog of Smubp-2 (cardiac transcription factor 1) was proposed to transactivate the atrial natriuretic factor (ANF) promoter through interaction with a cis-acting myocyte-specific element (Sebastiani et al., 1995). RNA helicases also have been implicated in transcriptional coregulation during development (Nakajima, 1997).

Because of its tissue and developmental stage specific expression, it is reasonable to speculate that CHAMP may be involved in cardiac-specific RNA-splicing and/or transcriptional regulation. In this regard, cardiac-specific RNA binding proteins and splicing events have been described (Siomi and Dreyfuss, 1997), but the specific factors involved have not been identified.

III. CHAMP PEPTIDES AND POLYPEPTIDES

CHAMP is a designation assigned by the present inventors for cardiac helicase activated by MEF2C protein. In addition to an entire CHAMP molecule, the present invention also relates to fragments of the polypeptides that may or may not retain various of the functions described below. Fragments, including the N-terminus of the molecule may be generated by genetic engineering of translation stop sites within the coding region (discussed below). Alternatively, treatment of the CHAMP with proteolytic enzymes, known as proteases, can produce a variety of N-terminal, C-terminal and internal fragments. Examples of fragments may include contiguous residues of SEQ ID NOS:2, 4, 6 and 8 of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Variants of CHAMP

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5± 1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure (Johnson et al, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of CHAMP, but with altered and even improved characteristics.

B. Domain Switching

Domain switching involves the generation of chimeric molecules using different but, in this case, related polypeptides. These molecules may have additional value in that these "chimeras" can be distinguished from natural molecules, while possibly providing the same function. For example, Upflp, Senlp, DNA helicase Hcslp, and murine Smubp-2 all provide suitable candidates for domain switching experiments.

C. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

D. Purification of Proteins

It will be desirable to purify CHAMP or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

E. Synthetic Peptides

The present invention also describes smaller CHAMP-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

F. Antigen Compositions

The present invention also provides for the use of CHAMP proteins or peptides as antigens for the immunization of animals relating to the production of antibodies. It is envisioned that CHAMP, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

IV. NUCLEIC ACIDS

The present invention also provides, in another embodiment, genes encoding CHAMP. Genes for mouse cardiac, mouse testis, human testis and human cardiac CHAMP have been identified. See, for example, SEQ ID NOS: 1, 3 5 and 7 respectively. The present invention is not limited in scope to these genes, however, as one of ordinary skill in the could, using these nucleic acids, readily identify related homologs in these and various other species (e.g., rat, rabbit, dog, monkey, gibbon, human, chimp, ape, baboon, cow, pig, horse, sheep, cat and other species).

In addition, it should be clear that the present invention is not limited to the specific nucleic acids disclosed herein. As discussed below, a "CHAMP gene" may contain a variety of different bases and yet still produce a corresponding polypeptide that is functionally indistinguishable, and in some cases structurally, from the human and mouse genes disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the activity of CHAMP.

A. Nucleic Acids Encoding CHAMP

Nucleic acids according to the present invention may encode an entire CHAMP gene, a domain of CHAMP, or any other fragment of CHAMP as set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given CHAMP from a given species may be represented by natural variants that have slightly different nucleic acid sequences but, nonetheless, encode the same protein (see Table 1 below).

As used in this application, the term "a nucleic acid encoding a CHAMP" refers to a nucleic acid molecule that has been isolated free of total cellular nucleic acid. In preferred embodiments, the invention concerns a nucleic acid sequence essentially as set forth in SEQ ID NOS: 1, 3, 5 or 7 (mouse cardiac, mouse testis, human testis, and human cardiac respectively). The term "as set forth in SEQ ID NOS: 1 or 3, 5 or 7" means that the nucleic acid sequence substantially corresponds to a portion of SEQ ID NO:1 or 3, 5 or 7. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NOS:1 or 3, 5 or 7 are contemplated. Sequences that are essentially the same as those set forth in SEQ ID NOS:1, 3, 5 or 7 may also be functionally defined as sequences that are capable of hybridizing to a nucleic acid segment containing the complement of SEQ ID NOS:1, 3, 5 or 7 under standard conditions.

The DNA segments of the present invention include those encoding biologically functional equivalent CHANIP proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequence set forth in SEQ ID NOS:1, 3, 5 or 7. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NOS:1, 3, 5 or 7 under relatively stringent conditions such as those described herein. Such sequences may encode entire CHAMP proteins or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or 5000 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. Formamide and SDS also may be used to alter the hybridization conditions.

One method of using probes and primers of the present invention is in the search for genes related to CHAMP or, more particularly, homologs of CHAMP from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single-stranded and double-stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

Antisense methodology takes advantage of the fact that nucleic acids tend to pair with "complementary" sequences.

By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 198.7; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

Within certain embodiments expression vectors are employed to express a CHAMP polypeptide product, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(i) Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 2 and Table 3). Additionally, any other promoter/enhancer combination (for example, as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |

TABLE 2-continued

Promoter and/or Enhancer

| Promoter/Enhancer | References |
| --- | --- |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1991; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the α actin promoter (Moss et al., 1996), the troponin 1 promoter (Bhavsar et al., 1996); the $Na^+/Ca^{2+}$ exchanger promoter (Barnes et al., 1997), the dystrophin promoter (Kimura et al., 1997), the creatine kinase promoter (Ritchie, M. E., 1996), the α7 integrin promoter (Ziober & Kramer, 1996), the brain natriuretic peptide promoter (LaPointe et al., 1996), the α B-crystallin/small heat shock protein promoter (Gopal-Srivastava, R., 1995), and α myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(iv) Delivery of Expression Constructs

There are a number of ways in which expression constructs may be introduced into cells. In certain embodiments of the invention, a vector (also referred to herein as a gene delivery vector) is employed to deliver the expression construct. By way of illustration, in some embodiments, the vector comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene delivery vectors were DNA viruses including the papovaviruses (simian virus 40, bovine papilloma virus, and polyoma) (Ridgeway, 1988; Baichwal and Sugden, 1986). Generally, these have a relatively low capacity for foreign DNA sequences and have a restricted host spectrum. They can accommodate only up to 8 kb of foreign genetic material but can be readily introduced in a variety of cell lines and laboratory animals (Nicolas and Rubenstein, 1988; Temin, 1986). Where viral vectors are employed to deliver the gene or genes of interest, it is generally preferred that they be replication-defective, for example as known to those of skill in the art and as described further herein below.

One of the preferred methods for in vivo delivery of expression constructs involves the use of an adenovirus expression vector. "Adenovirus expression vector" is meant to include those constructs containing adenovirus sequences sufficient to (a) support packaging of the construct and (b) to express a polynucleotide that has been cloned therein. In this context, expression does not require that the gene product be synthesized.

In preferred embodiments, the expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage and are able to infect non-dividing cells such as, for example, cardiomyocytes. So far, adenoviral infection appears to be linked only to mild disease such as acute respiratory disease in humans.

Adenovirus is particularly suitable for use as a gene delivery vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is important to minimize this possibility by, for example, reducing or eliminating adnoviral sequence overlaps within the system and/or to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the E3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of such adenovirus vectors is about 7.5 kb, or about 15% of the total length of the vector. Additionally, modified adenoviral vectors are now available which have an even greater capacity to carry foreign DNA.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, a preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be selected from any of the 42 different known serotypes or subgroups A–F. Adenovirus type 5 of subgroup C is a preferred starting material for obtaining a replication-defective adenovirus vector for use in the present invention. This is, in part, because Adenovirus type 5 is a human adenovirus about which a great deal of biochemical and genetic information is known, and it has historically been used for most constructions employing adenovirus as a vector.

As stated above, a preferred adenoviral vector according to the present invention lacks an adenovirus E1 region and thus, is replication. Typically, it is most convenient to introduce the polynucleotide encoding the gene of interest at the position from which the E1-coding sequences have been removed. However, the position of insertion of the construct within the adenovirus sequences is not critical to the invention. Further, other adenoviral sequences may be deleted and/or inactivated in addition to or in lieu of the E1 region. For example, the E2 and E4 regions are both necessary for adenoviral replication and thus may be modified to render an adenovirus vector replication-defective, in which case a helper cell line or helper virus complex may employed to provide such deleted/inactivated genes in trans. The polynucleotide encoding the gene of interest may alternatively be inserted in lieu of a deleted E3 region such as in E3 replacement vectors as described by Karlsson et al. (1986), or in a deleted E4 region where a helper cell line or helper virus complements the E4 defect. Other modifications are known to those of skill in the art and are likewise contemplated herein.

Adenovirus is easy to grow and manipulate and exhibits broad host range in vitro and in vivo. This group of viruses can be obtained in high titers, e.g., $10^9$–$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include administration via intracoronary catheter into one or more coronary arteries of the heart (Hammond, et al., U.S. Pat. Nos. 5,792,453 and 6,100,242) trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. In general, viral vectors accomplish delivery of the expression construct by infecting the target cells of interest. Alternatively to incorporating the expression construct into the genome of a viral vector, the expression construct may be encapsidated in the infectious viral particle.

Several non-viral gene delivery vectors for the transfer of expression constructs into mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression vector may simply consist of naked recombinant DNA or plasmids comprising the expression construct. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention, transferring of a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome, another non-viral gene delivery vector. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endbcytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

V. GENERATING ANTIBODIES REACTIVE WITH CHAMP

In another aspect, the present invention contemplates an antibody that is immunoreactive with a CHAMP molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to CHAMP-related antigen epitopes. Additionally, it is proposed that monoclonal antibodies specific to the particular CHAMP of different species may be utilized in other useful applications In general, both polyclonal and monoclonal antibodies against CHAMP may be used in a variety of embodiments. For example, they may be employed in antibody cloning protocols to obtain cDNAs or genes encoding other CHAMP. They may also be used in inhibition studies to analyze the effects of CHAMP related peptides in cells or animals. CHAMP antibodies will also be useful in immunolocalization studies to analyze the distribution of CHAMP during various cellular events, for example, to determine the cellular or tissue-specific distribution of CHAMP polypeptides under different points in the cell cycle. A particularly useful application of such antibodies is in purifying native or recombinant CHAMP, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are given in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified CHAMP protein, polypeptide or peptide or cell expressing high levels of CHAMP. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

VI. DIAGNOSING AND TREATING DEFECTS IN CHAMP

The inventors believe that CHAMP plays an important role in the development of cardiac tissue and, further, in the mechanisms of heart disease. Thus, in another embodiment, there are provided methods for diagnosing defects in CHAMP expression and function. More specifically, point mutations, deletions, insertions or regulatory pertubations relating to CHAMP, as well as increases or decrease in levels of expression, may be assessed using standard technologies, as described below.

A. Genetic Diagnosis

One embodiment of the instant invention comprises a method for detecting variation in the expression of CHAMP. This may comprise determining the level of CHAMP or determining specific alterations in the expressed product.

A suitable biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Various types of defects may be identified by the present methods. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of CHAMP produced, both by altering the transcription of the gene or in destabilizing or otherwise altering the processing of either the transcript (mRNA) or protein.

It is contemplated that other mutations in the CHAMP genes may be identified in accordance with the present inevntion. A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemillumiscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and ga& chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the CHAMP genes that may then be analyzed by direct sequencing.

(vi) Kit Components

All the essential materials and reagents required for detecting and sequencing CHAMP and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

B. Immunologic Diagnosis

Antibodies of the present invention can be used in characterizing the CHAMP content of healthy and diseased tissues, through techniques such as ELISAs and Western blotting. This may provide a screen for the presence or absence of cardiomyopathy or as a predictor of heart disease.

The use of antibodies of the present invention, in an ELISA assay is contemplated. For example, anti-CHAMP antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for CHAMP that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° C. to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

C. Treating Defects in CHAMP Expression or Function

The present invention also involves, in another embodiment, the treatment of disease states related to the aberrant expression and/or function of CHAMP. In particular, it is envisioned that CHAMP activity plays a role in development of cardiac tissue. Thus, increasing levels of CHAMP, or compensating for mutations that reduce or eliminate the activity of CHAMP, are believed to provide therapeutic intervention in certain cardiomyopathies.

In addition, by increasing levels of CHAMP, it is possible that defects in other cardiac genes may be compensated for. CHAMP may be able to overcome deficiencies in the expression of other cardiac factors.

There also may be situations where one would want to inhibit CHAMP function or activity, for example, where overexpression or unregulated expression had resulted in cardiac dysfunction. In this case, one would take steps to interfere with or block the expression of CHAMP, or inhibit its activity.

D. Genetic Based Therapies

One of the therapeutic embodiments contemplated by the present inventors is the intervention, at the molecular level, in the events involved in cardiac failure. Specifically, the present inventors intend to provide, to a cardiac cell, an expression construct capable of providing CHAMP to that cell. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred are liposomally-encapsulated expression vectors.

Those of skill in the art are aware of how to apply gene delivery to in vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below. Various routes are contemplated, including local and systemic, but targeted provision to the heart is preferred. (See, for example Hammond, et al., supra, hereby incorporated by reference in its entirety.)

E. Combined Therapy

In many clinical situations, it is advisable to use a combination of distinct therapies. Thus, it is envisioned that, in addition to the therapies described above, one would also wish to provide to the patient more "standard" pharmaceutical cardiac therapies. Examples of standard therapies include so-called "beta blockers", anti-hypertensives, cardiotonics, anti-thrombotics, vasodilators, hormone antagonists, endothelin antagonists, cytokine inhibitors/blockers, calcium channel blockers, phosphodiesterase inhibitors and angiotensin type 2 antagonists. Also envisioned are combinations with pharmaceuticals identified according to the screening methods described herein.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a CHAMP gene or protein, or the other agent will be desired. Various combinations may be employed, where CHAMP is "A" and the other agent is "B", as exemplified below:

A/B/A B/A/B B/B/A A/A/B B/A/A A/B/B B/B/B/A B/B/A/
B A/A/B/B A/B/A/B A/B/B/A B/B/A/A B/A/B/A B/A/A/B
B/B/B/A A/A/A/B B/A/A/A A/B/A/A A/A/B/A A/B/B/B B/
A/B/B B/B/A/B

Other combinations are contemplated as well.

F. Formulations and Routes for Administration to Patients

Where clinical applications are contemplated, it will be necessary to prepare pharmaceutical compositions—expression vectors, virus stocks and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal, intravascular or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VII. METHODS OF MAKING TRANSGENIC MICE

A particular embodiment of the present invention provides transgenic animals that contain CHAMP-related constructs. Transgenic animals expressing CHAMP, recombinant cell lines derived from such animals, and transgenic embryos may be useful in methods for screening for and identifying agents that modulate a function or activity of CHAMP, and thereby alleviate pathology related to the over or under expression of these molecules. The use of constitutively expressed CHAMP provides a model for over- or unregulated expression. Also, transgenic animals which are "knocked out" for CHAMP will find use in analysis of developmental aspects of CHAMP.

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA.

Other methods for purification of DNA for microinjection are described in Hogan et al. Manipulating the Mouse Embryo (Cold Spring Harbor Laboratory, Cold Spring Harbor, N.Y., 1986), in Palmiter et al. Nature 300:611 (1982); in *The Qiagenologist, Application Protocols,* 3rd edition, published by Qiagen, Inc., Chatsworth, Calif.; and in Sambrook et al. *Molecular Cloning: A Laboratory Manual* (Cold Spring Harbor Laboratory, Cold Spring Harbor, N.Y., 1989).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG, Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA, Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

VIII. SCREENING ASSAYS

The present invention also contemplates the screening of compounds for various abilities to interact and/or affect CHAMP expression or function. Particularly preferred compounds will be those useful in inhibiting or promoting the actions of CHAMP in cardiac differentiation and development. In the screening assays of the present invention, the candidate substance may first be screened for basic biochemical activity—e.g., binding to CHAMP, helicase activity, etc.—and then tested for its ability to modulate activity or expression, at the cellular, tissue or whole animal level.

A. Assay Formats

The present invention provides methods of screening for modulators of CHAMP. In one embodiment, the present invention is directed to a method of:

(i) providing a CHAMP polypeptide;
(ii) contacting the CHAMP polypeptide with the candidate substance; and
(iii) determining the binding of the candidate substance to the CHAMP polypeptide.

In yet another embodiment, the assay looks not at binding, but at CHAMP expression. Such methods would comprise, for example:

(i) providing a cell that expresses CHAMP polypeptide;
(ii) contacting the cell with the candidate substance; and
(iii) determining the effect of the candidate substance on expression of CHAMP.

In still yet other embodiments, one would look at the effect of a candidate substance on the activity of CHAMP. This may involve looking at any of a number of cardiac cell characteristics, including contractile function, and response to $Ca^{2+}$. Of particular interest will be measuring helicase activity. A model assay is found in Tang et al. (1999).

B. Inhibitors and Activators

An inhibitor according to the present invention may be one which exerts an inhibitory effect on the expression or function/activity of CHAMP. By the same token, an activator according to the present invention may be one which exerts a stimulatory effect on the expression or function/activity of CHAMP.

C. Candidate Substances

As used herein, the term "candidate substance" refers to any molecule that may potentially modulate CHAMP expression or function. The candidate substance may be a protein or fragment thereof, a small molecule inhibitor, or even a nucleic acid molecule. It may prove to be the case that the most useful pharmacological compounds will be compounds that are structurally related to compounds which interact naturally with CHAMP. Creating and examining the action of such molecules is known as "rational drug design," and include making predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a molecule like a CHAMP, and then design a molecule for its abilityt to interact with CHAMP. Alternatively, one could design a partially functional fragment of a CHAMP (binding but no activity), thereby creating a competitive inhibitor. This could be accomplished by x-ray crystallography, computer modeling or by a combination of both approaches.

It also is possible to use antibodies to ascertain the structure of a target compound or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known inhibitors of hypertrophic response.

Other suitable inhibitors include antisense molecules, ribozymes, and antibodies (including single chain antibodies).

It will, of course, be understood that all the screening methods of the present invention are useful in themselves notwithstanding the fact that effective candidates may not be found. The invention provides methods for screening for such candidates, not solely methods of finding them.

B. In Vitro Assays

A quick, inexpensive and easy assay to run is a binding assay. Binding of a molecule to a target may, in and of itself, be inhibitory, due to steric, allosteric or charge—charge interactions. This can be performed in solution or on a solid phase and can be utilized as a first round screen to rapidly eliminate certain compounds before moving into more sophisticated screening assays. In one embodiment of this kind, the screening of compounds that bind to a CHAMP molecule or fragment thereof is provided.

The target may be either free in solution, fixed to a support, expressed in or on the surface of a cell. Either the target or the compound may be labeled, thereby permitting determining of binding. In another embodiment, the assay may measure the inhibition of binding of a target to a natural or artificial substrate or binding partner (such as a CHAMP). Competitive binding assays can be performed in which one of the agents (CHAMP for example) is labeled. Usually, the target will be the labeled species, decreasing the chance that the labeling will interfere with the binding moiety's function. One may measure the amount of free label versus bound label to determine binding or inhibition of binding.

A technique for high throughput screening of compounds is described in WO 84/03564. Large numbers of small peptide test compounds are synthesized on a solid substrate, such as plastic pins or some other surface. The peptide test compounds are reacted with, for example, a CHAMP and washed. Bound polypeptide is detected by various methods.

Purified target, such as a CHAMP, can be coated directly onto plates for use in the aforementioned drug screening techniques. However, non-neutralizing antibodies to the polypeptide can be used to immobilize the polypeptide to a solid phase.

C. In Cyto Assays

Various cell lines that express CHAMP can be utilized for screening of candidate substances. For example, cells containing a CHAMP with engineered indicators can be used to study various functional attributes of candidate compounds. In such assays, the compound would be formulated appropriately, given its biochemical nature, and contacted with a target cell.

Depending on the assay, culture may be required. As discussed above, the cell may then be examined by virtue of a number of different physiologic assays (growth, size, $Ca^{++}$ effects). Alternatively, molecular analysis may be performed in which the function of a CHAMP and related pathways may be explored. This involves assays such as those for protein expression, enzyme function, substrate utilization, mRNA expression (including differential display of whole cell or polyA RNA) and others.

D. In Vivo Assays

The present invention particularly contemplates the use of various animal models. Transgenic animals may be created with constructs that permit CHAMP expression and activity to be controlled and monitored. The generation of these animals has been described elsewhere in this document.

Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply.

E. Production of Inhibitors

In an extension of any of the previously described screening assays, the present invention also provide for method of producing inhibitors. The methods comprising any of the preceding screening steps followed by an additional step of "producing the candidate substance identified as a modulator of" the screened activity.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification, Isolation and Characterization of CHAMP

A. Material and Methods

Breeding of Mice and Genotyping. Mice heterozygous for a MEF2C null mutation were generated as previously described (Lin et al., 1997). Intercrosses of MEF2C heterozygous mice in the 129SVEV/C57BL6 background were performed to obtain homozygous-null embryos between embryonic day 9.0–9.5 (E9.25). Hearts were dissected out from homozygous embryos and stored frozen at –80° C. Care was taken to make sure that only viable embryos with beating hearts were used. For a control, wild-type littermates were recovered at E9.25, and the hearts and remaining embryonic tissues were frozen separately at –80° C. Genotypes of individual embryos were determined by PCR analysis of yolk sac DNA as previously described (Lin et al., 1997).

RNA Preparation, cDNA Synthesis and Subtraction Hybridization. Total RNA was prepared using Trizol reagent (Gibco) from 40 hearts of MEF2C-null and the wild-type littermates, respectively. Five-hundred nanograms each of total RNA was subjected to reverse-transcription and PCR amplification using the SMART cDNA synthesis system (Clontech). Reactions were terminated at 18 cycles in the linear-increase range of PCR amplification. cDNA larger than 1 kb was enriched by size-fractionation and was digested with RsaI.

Subtractive hybridization was performed using wild-type heart cDNA as a tester and MEF2C-null heart cDNA as a driver (forward subtraction, WT-KO) by the PCR-Select system (Clontech). Briefly, wild-type heart cDNA was ligated separately with two different adaptors, and each sample was hybridized with an excess amount of MEF2C-null heart cDNA. These samples were combined and hybridized to form double-stranded cDNA with different adaptors at the ends. cDNA clones representing transcripts specifically expressed in the wild-type heart were preferentially amplified by PCR using the primers specific to the adaptors.

Simultaneously, the reverse subtractive hybridization (KO-WT) was also performed using MEF2C-null heart cDNA as a tester and wild-type heart cDNA as a driver to enrich for cDNA representing transcripts highly expressed in the MEF2C-null hearts.

Differential Array Analysis. Subtracted PCR fragments were subcloned into pCRII-TOPO plasmids (Invitrogen), and 1,000 bacterial clones were recovered and cultured for 5 h. cDNA inserts of the plasmid clones were amplified by PCR using adapter-specific primers and were arrayed in duplicate onto replica nylon membranes.

Subtracted PCR fragments from the forward (WT-KO) and reverse subtractions (KO-WT) were labeled with $^{32}$P-dCTP, respectively. Each membrane was hybridized with either forward or reverse probes in Rapid-hyb buffer (Amersham) at 65° C. and washed serially, with a final wash in 0.1×SSC, 0.1% SDS at 65° C. Autoradiography was performed using Phosphor-imaging (Molecular Dynamics). After stripping and prehybridization, one of the replica membranes was hybridized with $^{32}$P-labeled cDNA probes prepared from whole-embryo without heart tissues.

Southern Blot Analysis of PCR-Amplified cDNA. To examine the expression patterns of isolated genes in MEF2C-null hearts and wild-type hearts, the inventors performed Southern blot analysis of PCR fragments obtained by SMART cDNA synthesis (virtual Northern analysis). Approximately the same amount of cDNA mixtures for the MEF2C-null hearts, wild-type hearts and whole-embryo minus heart tissues was electrophoresed on a 1.5% agarose/TAE gel and transferred onto nylon membranes. The membranes were hybridized with the PCR fragments of individual clones in Rapid-hyb buffer at 65° C. and washed serially, with a final wash in 0.1×SSC, 0.1% SDS at 65° C. The signals were visualized by autoradiography.

Isolation and Characterization of CHAMP. The original 0.6 kb cDNA clone R15-C5, isolated from subtractive cloning, was used to screen a mouse E10.5 heart cDNA library (Stratagene). The screening procedure was described previously (Nakagawa et al., 1999). After plaque purification, eight positive clones were obtained and the cDNAs were excised into pBluescript H plasmids following the protocol provided by the manufacturer (Stratagene). After sequencing the overlapping clones, only a 1.5 kb sequence from the 3'-end of the message was obtained. Using the 5'-end sequence (0.3 kb) of the 1.5 kb clone, cDNA libraries from mouse E10.5 heart (Stratagene) and mouse adult heart (Clontech) were further screened and a total of approximately 1.7 kb sequence was obtained. 5'-RACE cloning provided additional 5' sequence resulting an approximately 2 kb sequence. (SEQ ID NO: 2).

In situ Hybridization. Whole mount in situ hybridization and radioactive section in situ hybridization were performed as previously described (Nakagawa et al., 1999) on mouse embryos from E7.75 to E 15.5, and on adult mouse heart. Plasmids containing nucleotides 589–994 and 1420–2020 of the 2 kb CHAMP cDNA were used as the templates for making $^{35}$S-UTP labeled and digoxigenin-labeled riboprobes for section and whole mount in situ hybridization, respectively. cDNA probes corresponding to these two fragments yielded the same results on Northern blot analysis (see below).

Northern Blot Analysis. Northern blot analysis was performed on a mouse adult tissue poly(A)+ RNA blot (Clontech) using $^{32}$P-labeled CHAMP cDNA fragments corresponding to nucleotides 589–994 and 1420–2020 as probes. The membrane was prehybridized and hybridized in Rapid-hyb buffer at 65° C. and washed serially, with a final wash in 0.2×SSC, 0.1% SDS at 65° C. Autoradiography was performed at −80° C. for 15 h with an intensifying screen.

B. Results

Identification of MEF2C-Dependent Genes. At E8.0–E8.5, MEF2C mutant and wild-type embryos are indistinguishable, whereas by E9.0, when the heart tube should undergo rightward looping to form the future right ventricular chamber, the heart tube of the MEF2C: mutant remains linear, with a single hypoplastic ventricular chamber fused directly to an enlarged atrial chamber (Lin et al., 1997). Cardiomyocytes within the mutant myocardial wall become disorganized at this stage and the heartbeat becomes sluggish and irregular. Mutant embryos also develop pericardial effusion, indicative of hemodynamic insufficiency and heart failure, at about E9.0.

To identify potential MEF2C-dependent genes in the heart tube, the inventors performed differential array analysis using cDNA derived from subtractive hybridization of total RNA isolated from heart tubes of wild-type and MEF2C mutant embryos at E9.0 to E9.5. At this stage, homozygous mutants were viable, but were visually identifiable by cardiac malformation. The genotypes of individual embryos were confirmed by PCR analysis on yolk sac DNA.

The overall strategy of the differential cDNA array coupled with subtractive hybridization is illustrated in FIG. 1A. Approximately 1000 cDNA clones obtained from subtractive hybridization of wild-type and MEF2C-null heart tubes were arrayed in duplicate onto replica nylon membranes. The arrayed membranes were subsequently probed with cDNA from the forward (see, for example, FIG. 1B, panel a) and reverse subtractions (see, for example, FIG. 1B, panel b), respectively, as described above. To identify clones that were potentially cardiac-specific, one of the arrays was subsequently stripped and hybridized with $^{32}$P-labeled cDNA prepared from wild-type whole embryo without the heart (see, for example, FIG. 1B, panel c).

Approximately 169 of 1000 arrayed clones showed higher expression in wild-type as compared to MEF2C mutant heart tubes. The differential expression of the 169 clones was consistent in duplicate membranes. Of these 169 potential MEF2C-dependent clones, approximately forty-seven appeared to be cardiac-specific, based on their lack of hybridization to cDNA from whole embryo without the heart (FIG. 1B, panel c).

Based on sequence analysis, the inventors were able to categorize MEF2C-dependent genes into four major classes: 1) muscle genes, 2) stress- and growth-related genes, 3) genes encoding enzymes involved in electron transport and ATP synthesis, and 4) novel genes. To confirm the differential expression of the above genes, the inventors determined the expression patterns of representative genes from each class by "virtual" Northern analysis, in which RNA from wild-type and MEF2C mutant heart tubes and from E9.25 embryos without the heart was converted to cDNA and probed by Southern blot (data not shown).

Virtual Northern blots showed that transcripts for clone R15-C5 were expressed at levels about 5 to 10-fold higher in heart tubes from wild-type compared to MEF2C mutants. Further confirming this differential expression pattern, R15-C5 transcripts were expressed throughout the heart tube of wild-type embryos at E8.0, as detected by whole-mount in situ hybridization, whereas in MEF2C mutants they were undetectable (FIG. 2).

CHAMP, a Cardiac-Specific Helicase-Like Factor Dependent on MEF2C. The inventors chose to focus on clone R15-C5 one of the novel MEF2C-dependent cDNAs identified in the screen. The initial cDNA for clone R15-C5 was 600 nucleotides in length and contained a short putative open reading frame followed by a polyA stretch preceded by stop codons in all three potential reading frames, suggesting it represented a partial coding sequence and a 3'-untranslated region. At the time it was first identified, there was no match for this sequence in the database. Screening of cDNA libraries of mouse E10.5 and adult heart yielded a cDNA clone of approximately 1.7 kb. Using cDNA fragments derived from this clone as probes in Northern blots of adult mouse tissues, the inventors detected a single approximately 1.8 kb transcript only in the heart and lower levels of an approximately 4.4 kb transcript in testis (FIG. 3). 5'-RACE cloning of the cardiac transcript provided additional 5' sequence resulting in a 2 kb sequence. (SEQ ID NO: 2).

Figure 4:
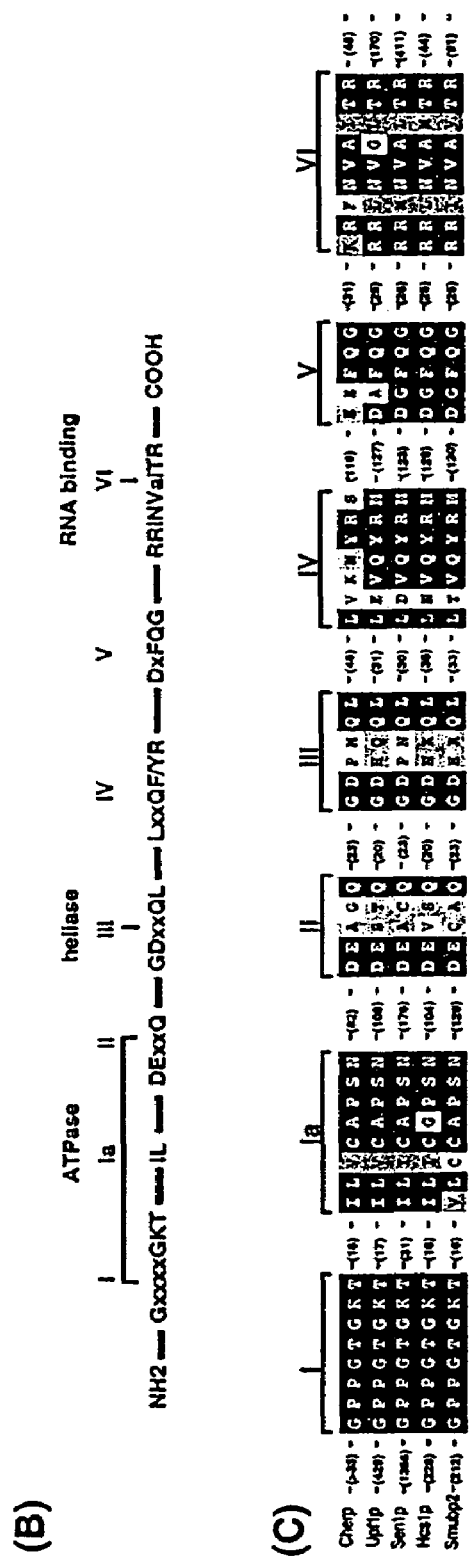
FIGS. 4A–C—Deduced amino acid sequence of CHAMP cDNA and its alignment to other helicases.

Sequencing of the cDNA clone revealed that R15-C5 encoded a novel protein with seven conserved motifs characteristic of RNA helicases, including ATPase motifs (I, Ia, and II), a helicase motif (III), and an RNA binding motif (VI) (FIG. 4A, underlined). Sequencing of the 2 kb cDNA clone revealed a single open reading frame encoding a putative protein of 550 amino acids (SEQ ID NO:2). Based on its cardiac-specific expression and homology to other helicases, the inventors refer to the R15-C5 gene as cardiac helicase activated by MEF2 protein, CHAMP. Searching EST databases, the inventors found an EST clone (accession number ALI 33068) from a human testis library encoding a putative human ortholog of CHAMP. The sequences of human and murine CHAMP are over 90% identical.

Using BLAST search, the inventors found that CHAMP is most clearly related to RNA helicase superfamily 1. FIG. 4C shows the amino acid sequence alignment of the seven conserved motifs of CHAMP with members of RNA helicase superfamily I (yeast Upf I p, Sen I p, and Hcs I p, and murine Smubp-2). Superfamily I includes RNA and DNA helicases, some of which exhibit both RNA and DNA helicase activities (de la Cruz et al., 1999). Members of this RNA helicase superfamily are related by a common central region containing the seven conserved motifs flanked by divergent sequences at both ends. This central region is essential and sufficient for helicase activity which unwinds RNA and/or DNA duplexes with energy derived from ATP hydrolysis. Mutational analyses have revealed that motif I and Ia and II are involved in ATP binding and hydrolysis (Weng et al., 1996). Motifs III and VI are involved in unwinding activity and RNA/DNA binding, respectively. It has been shown that yeast Upflp and Senlp have helicase activities that unwind both RNA and DNA duplexes unidirectionally from 5' to 3' ends (Czaplinski, 1995; Kim et al., 1999). The variable N- and C-terminal regions have been postulated to participate in recognition and subcellular localization of substrates. Some RNA helicases also contain additional DNA and/or RNA binding sites at their N- and/or C-termini. The observation that CHANIP contains all seven motifs conserved in RNA helicase superfamily suggests that its function may be related to those of members of the family.

Figure 5:
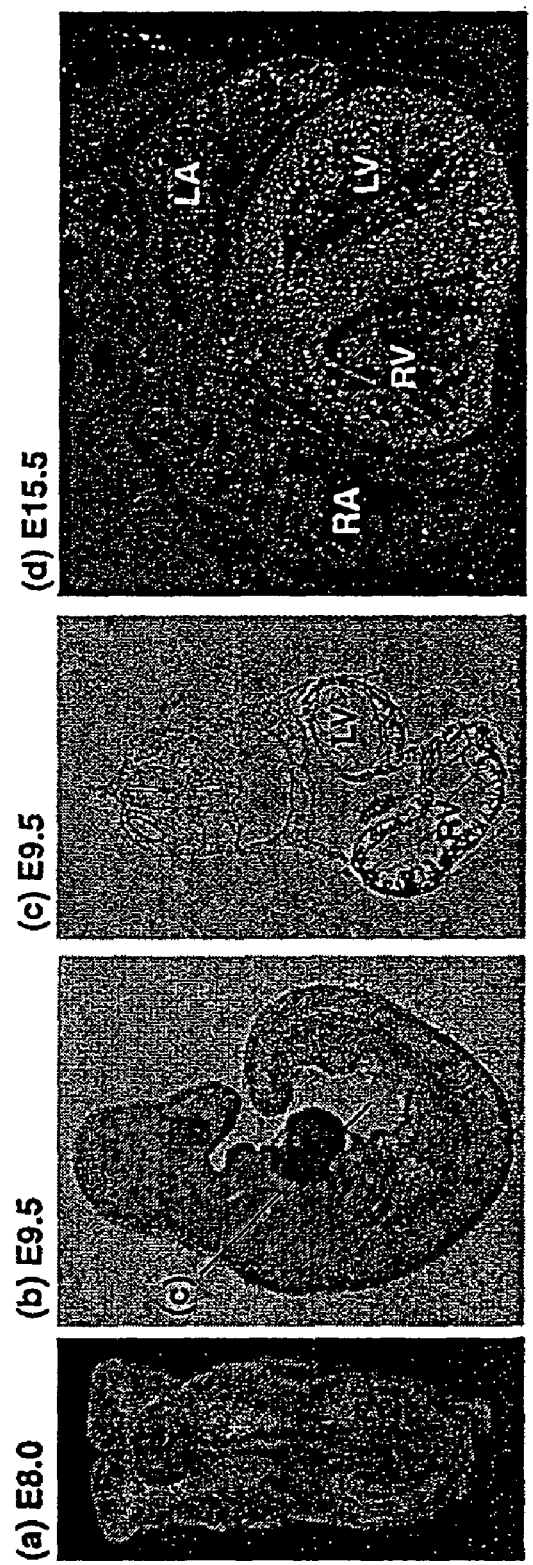
FIGS. 5A–D—CHAMP expression during mouse embryogenesis detected by whole mount and radioactive section in situ hybridization.
Figure 6:
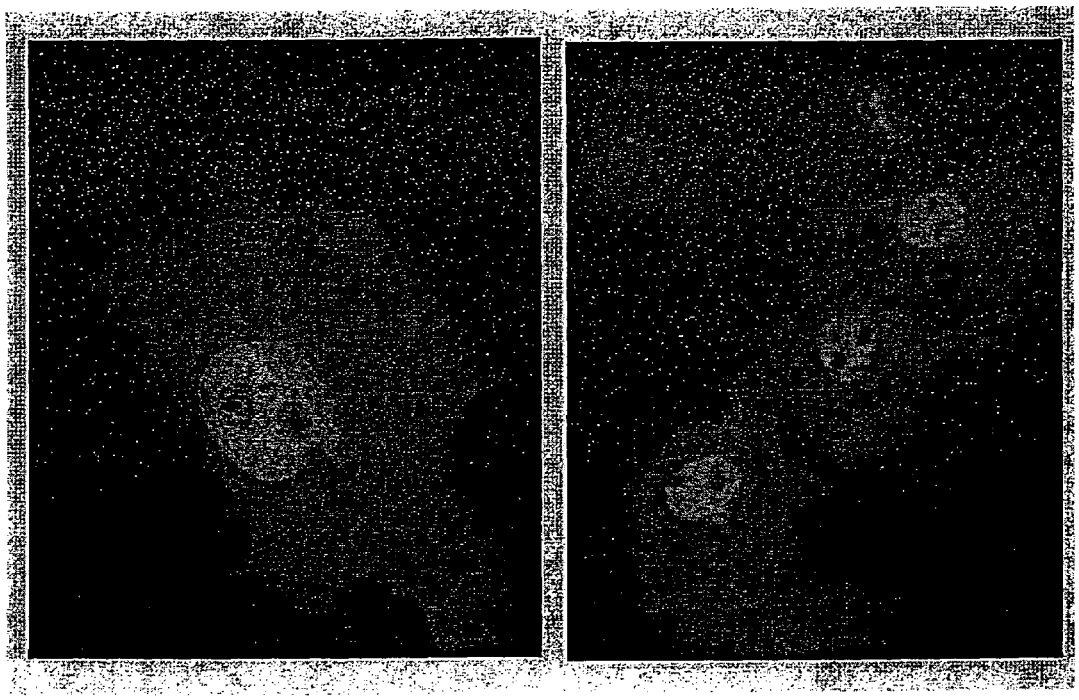
FIG. 6—Nuclear localization of CHAMP. COS cells were transiently transfected with a CHAMP expression vector with an epitope tag and the subcellular location of CHAMP protein was determined by immunofluorescence. The two panels show different magnifications and demonstrate the localization of CHAMP protein to the nucleus.

Embryonic Expression Pattern of CHAMP. The expression pattern of CHAMP during mouse embryogenesis was determined by in situ hybridization. CHAMP transcripts were not detected in the cardiac crescent at E7.5 by whole mount in situ hybridization. CHAMP expression was first observed in the linear heart tube at E8.0 where the two bilateral heart primordia have fused at the central midline (FIG. 5A). CHAMP is expressed in an anterior-posterior gradient fashion in the heart tube at this stage. The highest expression of CHAMP was in the anterior part of the primitive heart tube that is fated to form the ventricular segments. CHAMP expression was not detected at the most posterior branches of the forming heart tube (FIG. 5A). These branches, known as the sinus venosae, later form atrial chambers of the heart (DeHaan, 1965). The onset of CHAMP expression is about a half-day later than the initial expression of MEF2C (Edmondson et al., 1994), which is consistent with CHAMP being a downstream target of MEF2C. The ventricular expression of CHAMP was maintained in the looped heart tube at E9.5 (FIG. 5B). At this stage, a low level of CHAMP expression was also detectable in precursor cells of atria. Subsequently, CHAMP expression was seen predominantly in the ventricular region throughout the developing heart and into adulthood (FIG. 5D). Radioactive section in situ hybridization at E15.5 indicated that CHAMP was specifically expressed within myocardial cells (FIG. 5D). At embryonic day 15.5, ventricular cardiomyocytes form finger-like projections, known as trabeculae. CHAMP appears to be expressed preferentially in the trabecular region where the proliferative rate is diminished relative to the adjacent compact zone. Thus, it was postulated that CHAMP may play a role in suppression of cell proliferation and/or cardiomyocyte hypertrophy. No CHAMP expression was detected in the embryonic vasculature and outflow tract.

Example 2

Suppression of Proliferation and Cardiomyocyte Hypertrophy by CHAMP

A. Materials and Methods

Materials. Phospho-p44/p42 mitogen-activated protein kinase (MAPK) antibodies were purchased from Cell. Signaling Technology Inc. Anti-p21$^{CIP1}$ antibody was purchased from PharMingen International. Rabbit anti-atrial natriuretic factor (ANF) antibody was purchased from Peninsula Laboratory, Inc. Monoclonal anti α-actinin antibody and anti-tubulin antibody were purchased from Sigma. Rabbit anti-calsarcin antibody and anti-CHAMP antibody have been described previously (Liu et al., 2001; Frey et al., 2000). All other antibodies were purchased from Santa Cruz Biotechnology.

Construction of adenovirus and expression vectors. A cDNA clone encoding full-length CHAMP with an amino-terminal FLAG epitope tag was cloned into the pcDNA expression vector using standard techniques(See, e.g., Liu et al., 2001). This cDNA fragment was also used to construct a recombinant adenovirus using the Adeno-X Tet-off system according to manufacturer's protocols (Clontech). Target cells were co-infected with Adeno-X Tet-off virus (adTet-off) and adenovirus encoding FLAG-tagged CHAMP (ad-CHAMP). Cells were infected with a 1:2 ratio of adCHAMP to adTet-off virus at the multiplicities of infection (MOI) specified in the text. The expression level of CHAMP was controlled by the amount of doxycycline added to the medium with maximum expression being achieved in the absence of doxycycline. Because the basal level of CHAMP expression in the presence of doxycycline (1 µg/ml) had significant effects on HeLa cell proliferation and cardiomyocyte growth, no attempt was made to correlate the levels of exogenous CHAMP expression with its anti-proliferative effect on cell growth and no doxycycline was used in the studies reported here. As a control, the inventors routinely infected cells with adenovirus that constitutively expressed β-galactosidase (adβ-gal) at a similar MOI.

A mutant form of CHAMP in which the conserved ATPase domain (DEAGQ) was mutated to GGAAG was generated using the QuickChange Site-Directed Mutagenesis kit from Stratagene. The pcDNA-FLAG-CHAMP expression vector was used as the parental plasmid for mutagenesis.

Cell proliferation assay. Cell proliferation assays were performed in 96-well microtiter plates using cell proliferation ELISA, BrdUrd (chemiluminescence) kit (Roche Molecular Biochemicals). HeLa cells were seeded at a density of $0.5 \times 10^4$ cells/well in a volume of 100 µl medium/well and cultivated in Dulbecco's Modified Eagle's Medium (DMEM) supplemented with 10% fetal bovine serum (FBS). After 24 hrs, cells were infected with adenovirus at an MOI of 40 overnight at 37° C. The medium was replaced with fresh medium after infection and cells were incubated for another 48 hrs. At the end of the incubation, 5-bromo-2'-deoxyuridine (BrdUrd) was added to the medium and cells were incubated for 2 hrs. At the end of the labeling period, cells were fixed and peroxidase-conjugated anti-BrdUrd antibody was added. Immune complexes were detected by addition of substrate and subsequent quantitation of luminescence using a microplate luminometer.

Primary neonatal rat cardiomyocyte cell culture. Primary cultures of neonatal rat ventricular cardiomyocytes were prepared as described previously (Molkentin et al., 1998). Twenty four hours after seeding, infection with adenovirus was carried out in plating medium for 2 hrs at an MOI of 2. After infection, the culture medium was changed to serum-free medium and 24 hrs later hypertrophic stimuli [phenylephrine (PE) (20 μg/ml), 10% FBS, or isopreterenol (10 μM)] were added. Cells were harvested at various time points after hypertrophic stimulation. RNA and protein were isolated for RNA dot blot and Western blot analysis.

Only cultures containing greater than 90% cardiomyocytes were used. At an MOI of 2, greater than 90% of cardiomyocytes were infected by adCHAMP.

Measurements of cell size. For cell size measurements, approximately 100 cells from each condition were randomly chosen and photographed at 40×. Myocyte cross-sectional areas were measured using a computerized morphometric system (Scion Image, National Institutes of Health).

Extracellular Signal-Regulated Kinase (ERK) activity assay. MAPK activities were assayed using phospho-p42/p44 MAPK (ERK1/2) antibodies. Stimulated cardiomyocytes were harvested in SDS sample buffer at various time points. Approximately 20 μg protein was separated on 10% SDS-PAGE and blotted to nitrocellulose membranes. Two identical blots were incubated with antibody specific for the dually phosphorylated, activated forms of ERK1 and ERK2 (Cell Signaling Technology), and an antibody specific for ERK2 that is independent of its phosphorylation state (Santa Cruz Biotechnology). Signals were detected using horse radish peroxidase-conjugated secondary antibody and enhanced chemiluminescence (Amersham Pharmacia).

RNA analysis. Total RNA was isolated from cultured cardiomyocytes using Trizol reagent (GIBCO-BRL) according to manufacturer's instructions. RNA dot blotting was performed with 1 ug total RNA dotted on nitrocellulose membrane and hybridized against a panel of oligonucleotide probes as described (Nicol et al., 2001). Northern blot analysis with CHAMP and $p21^{CIP1}$ cDNA probes and RT-PCR were performed following previously described procedures (See, e.g., Liu et al., 2001).

Western Blot analysis. Extracts from cardiomyocytes or adult mouse hearts containing 20 μg of protein were subjected to SDS-polyacrylamide gel electrophoresis. Protein was transferred to poly(vinylidene difluoride) PVDF membrane and subjected to Western blot analysis with anti-fos antibody, anti-tubulin antibody, and anti-CHAMP as described (Liu et al., 2001).

Immunofluorescence. The immunofluoresecence staining of cardiomyocytes was performed as described (Liu et al., 2001).

B. Results

Inhibition of cell proliferation by CHAMP. In light of the preferential expression of CHAMP in the trabecular region of the developing heart (Nozato et al., 2000), in which the proliferative rate of cardiomyocytes is reduced relative to the adjacent compact zone (Nicol et al., 2001), the inventors investigated whether CHAMP might suppress cell proliferation. To test this possibility, they expressed CHAMP ectopically in HeLa cells using an adenoviral expression vehicle and examined the effect on cell proliferation as measured by incorporation of BrdUrd into newly synthesized DNA. BrdUrd incorporation was inhibited by approximately 75% in HeLa cells infected with adCHAMP compared to cells expressing adβ-gal as a control.

Since HeLa cells are highly transformed and do not undergo complete cell cycle arrest in response to growth restriction, the inventors further examined whether CHAMP could prevent the transition of NIH-3T3 cells from quiescence to S phase in response to serum stimulation. As a control, they also generated a mutant form of CHAMP in which the ATPase domain (domain II), which is conserved in members of the helicase superfamily, was mutated from DEAGQ to GGAAG. The wild-type and mutant forms of CHAMP were expressed at comparable levels in the cytoplasm of transfected cells.

NIH-3T3 cells maintained in 0.5% FBS for 24 hrs were transfected with an expression vector encoding wild-type and mutant CHAMP. Twenty-four hours later, fresh medium supplemented with 10% FBS was added to induce synchronous reentry into the cell cycle and proliferative activity was assayed by staining for proliferating cellular nuclear antigen (PCNA) after an additional 24 hrs. Only 10% of cells that expressed CHAMP were PCNA-positive, compared to 70% of untransfected cells. In contrast, 68% of cells expressing the mutant form of CHAMP were able to enter the cell cycle and show positive PCNA staining. Based on cell morphology and Hoechst staining of nuclei, there was no evidence for apoptosis of CHAMP-expressing cells. These results demonstrate that CHAMP can block cell proliferation and suggest that the ATPase activity of the conserved helicase motif is required for its anti-proliferative effects.

Inhibition of cardiomyocyte hypertrophy by CHAMP. Hypertrophic growth of cardiac myocytes in response to extracellular agonists is controlled by many of the same signal transduction pathways that control proliferation of non-muscle cells. In light of the ability of CHAMP to block cell proliferation, the inventors tested whether it could also interfere with agonist-dependent hypertrophy of cardiomyocytes. Hypertrophy was assayed by expression of fetal genes following stimulation by the α-adrenergic agonist phenylephrine (PE). PE stimulated the expression of atrial natriuretic factor (ANF), brain natriuretic factor (BNP), β-myosin heavy chain (β-MHC), skeletal α-actin and cardiac α-actin to varying levels. In the presence of adCHAMP, the up-regulation of ANF, BNP, β-MHC, and cardiac α-actin by PE was blocked. In contrast, adCHAMP had no effect on expression of skeletal α-actin or glyceraldehyde-3-phosphate dehydrogenase (GAPDH), which is expressed ubiquitously. The suppression of hypertrophic gene expression was a specific response to adCHAMP and was not observed with adβ-gal. A similar inhibitory effect of adCHAMP on induction of hypertrophic marker genes was observed in cardiomyocytes stimulated with serum and isoproterenol.

The inventors also examined the effect of adCHAMP on hypertrophic responsiveness by immunostaining of cardiomyocytes with anti-ANF antibody. Cardiomyocytes were identified by immunostaining for α-actinin, and CHAMP expression was confirmed by staining with a polyclonal anti-CHAMP antibody. ANF shows a perinuclear staining pattern in cardiomyocytes stimulated with PE. In adCHAMP-infected cells stimulated with PE, ANF staining was undetectable. PE also stimulates sarcomere organization, as shown by α-actinin staining, and induces an increase in cell size. AdCHAMP completely inhibited the PE-induced increase in cell size, but it did not appear to prevent the organization of sarcomeres. Cells that expressed ectopic CHAMP appeared healthy, despite their inability to mount a hypertrophic response. There was also no increase in apoptosis in CHAMP-expressing cells, as determined by terminal deoxynucleotidyltransferase-mediated UTP end labeling (TUNEL) staining. The anti-hypertrophic effect of CHAMP on cardiomyocytes was observed over a wide range of adCHAMP expression (from 3 to 100-fold compared to the endogenous level, data not shown).

CHAMP does not affect early mitogenic responses. PE-induced cardiomyocyte hypertrophy involves activation of cascades of MAP kinases, especially p44 (ERK1) and p42 (ERK2) (Clerk and Sugden, 1999). To determine the effect of CHAMP on PE-stimulated ERK1/2 activities, cardiomyocytes were harvested at multiple time points after PE stimulation and MAP kinase assays were performed by immunoblotting with antibodies specific for activated phospho-ERKs. As reported previously, PE stimulation of cultured cardiomyocytes led to a pronounced increase in ERK1 and ERK2 phosphorylation. Cardiomyocytes infected with adCHAMP showed comparable activation of ERKs.

Expression of c-fos is a sensitive marker of early mitogenic signaling events. Up-regulation of c-fos expression by PE, as measured by RT-PCR and Western blot, was unaffected by adCHAMP. Thus, the inhibition of hypertrophic signaling by CHAMP does not appear to be attributable to a disruption of early mitogenic signaling events.

CHAMP up-regulates $p21^{CIP1}$. The CDK inhibitor $p21^{CIP1}$ acts as a suppressor of cell proliferation and has been implicated as a negative regulator of cardiomyocyte hypertrophy (Li & Brooks, 1999; von Harsdorf, et al., 1999). To further investigate the basis for the anti-hypertrophic activity of CHAMP, we analyzed the expression of $p21^{CIP1}$ by immunofluorescence staining of PE-stimulated cardiomyocytes in the presence and absence of adCHAMP. Cardiomyocytes were distinguished from contaminating fibroblasts by staining with an antibody for calsarcin, a muscle-specific component of the Z-band (Liu et al., 2001). Only a small fraction of neonatal cardiomyocytes (<10%) showed $p21^{CIP1}$-positive staining in the absence of adCHAMP. In contrast, more than 80% of adCHAMP-infected cardiomyocytes showed strong $p21^{CIP1}$ staining.

Down-regulation of CHAMP expression in hypertrophic hearts from α-MHC-calcineurin transgenic mice. Based on the ability of CHAMP to block cardiomyocyte hypertrophy in vitro, the inventors investigated whether CHAMP might be down-regulated in response to hypertrophic stimuli in vivo, thereby facilitating a hypertrophic growth response. The possible regulation of CHAMP expression during hypertrophy was examined using transgenic mice that expressed a constitutively activated form of the calcineurin phosphatase under control of the α-MHC promoter. These mice develop severe cardiac hypertrophy by 4 weeks of age, which progresses to dilated cardiomyopathy and heart failure (Molkentin, et al., 1998). CHAMP mRNA and protein were down-regulated 5-fold in hypertrophic hearts from α-MHC-calcineurin transgenic mice at 8-weeks of age.

All of the COMPOSITIONS and METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS and METHODS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 5,354,855
U.S. Pat. No. 5,792,453
U.S. Pat. No. 6,100,242
U.S. Pat. No. 4,196,265
U.S. Pat. No. 4,683,195
U.S. Pat. No. 4,683,202
U.S. Pat. No. 4,800,159
U.S. Pat. No. 4,883,750
U.S. Pat. No. 5,279,721
U.S. Pat. No. 4,873,191
Angel, Bauman, Stein, Dellus, Rahmsdorf, and Herrlich, "12-O-tetradecanoyl-phorbol-13-acetate Induction of the Human Collagenase Gene is Mediated by an Inducible Enhancer Element Located in the 5' Flanking Region," *Mol. Cell. Biol.,* 7:2256, 1987a.
Angel, Imagawa, Chiu, Stein, Imbra, Rahmsdorf, Jonat, Herrlich, and Karin, "Phorbol Ester-Inducible Genes Contain a Common cis Element Recognized by a TPA-Modulated Trans-acting Factor," *Cell,* 49:729, 1987b
Atchison and Perry, "Tandem Kappa Immunoglobulin Promoters are Equally Active in the Presence of the Kappa Enhancer: Implications for Model of Enhancer Function," *Cell,* 46:253, 1986.
Atchison and Perry, "The Role of the Kappa Enhancer and its Binding Factor NF-kappa B in the Developmental Regulation of Kappa Gene Transcription," *Cell,* 48:121, 1987.
Baichwal and Sugden, "Vectors for gene transfer derived from animal DNA viruses: Transient and stable expression of transferred genes", In: *Gene Transfer,* Kucherlapati R, ed., New York, Plenum Press, pp. 117–148, 1986.
Banerji, Olson, and Schaffner, "A lymphocyte-specific cellular enhancer is located downstream of the joining region in immunoglobulin heavy-chain genes," *Cell,* 35:729, 1983.
Barany and Merrifield, The Peptides, Gross and Meienhofer, eds., Academic Press, New York, pp. 1–284, 1979.
Barnes, Cheng, Dawson, Menick, "Cloning of cardiac, kidney, and brain promoters of the feline ncx1 gene," *J. Biol. Chem.,* 272(17):11510–7, 1997.
Baughman, K., *Cardiology Clinics,* 13: 27–34, 1995.
Benvenisty and Neshif, "Direction introduction of genes into rats and expression of the genes", *Proc. Nat'l Acad. Sci. USA,* 83:9551–9555, 1986.
Berkhout et al., "Tat trans-activates the human immunodeficiency virus through a nascent RNA target," *Cell,* 59:273, 1989.

Bhavsar, Brand, Yacoub, Barton, "Isolation and characterization of the human cardiac troponin I gene (TNNI3)," *Genomics*, 35(1):11–23, 1996.

Biben and Harvey, "Homeodomain factor Nkx2-5 controls left/right asymmetric expression of bHLH bene eHand during murine heart development," *Genes Dev.*, 11:1357–1369, 1997.

Black and Olson, "Transcriptional control of muscle development by myocyte enhancer factor-2 (MEF2) proteins," *Annual Rev. Cell Dev. Biol.*, 14:167–196, 1998.

Blanar, Baldwin, Flavell, Sharp, "A gamma-interferon-induced factor that binds the interferon response sequence of the MHC class I gene, H-2 Kb," *EMBO J.*, 8(4): 1139–44, 1989.

Bodine and Ley, "An enhancer element lies 3' to the human A gamma globin gene," *EMBO J.*, 6:2997, 1987.

Boshart, Weber, Jahn, Dorsch-Hasler, Fleckenstein, and Schaffner, "A very strong enhancer is located upstream of an immediate early gene of human cytomegalovirus," *Cell*, 41:521, 1985.

Bosze, Thiesen, and Chamay, "A transcriptional enhancer with specificity for erythroid cells is located in the long terminal repeat of the friend murine leukemia virus," *EMBO J.*, 5:1615, 1986.

Bour, O'Brien, Lockwood, Goldstein, Bodmer, Taghert, Abmayr, Nguyen, "*Drosophila* MEF2, a transcription factor that is essential for myogenesis," *Gene Devel.*, 9:730–741, 1995.

Braddock, Chambers, Wilson, Esnouf, Adams, Kingsman, and Kingsman, "HIV-I Tat activates presynthesized RNA in the nucleus," *Cell*, 58:269, 1989.

Braunwald, E. (ed), In: "Heart Disease," W.B. Saunders, Philadelphia, page 426, 1988.

Brinster, Chen, Trumbauer, Yagle, Palmiter, "Factors affecting the efficiency of introducing foreign DNA into mice by microinjecting eggs," *Proc Nat'l Acad Sci USA*, 82(13):4438–4442, 1985.

Bulla and Siddiqui, "The hepatitis B virus enhancer modulates transcription of the hepatitis B virus surface-antigen gene from an internal location," *J. Virol.*, 62:1437, 1986.

Campbell and Villarreal, "Functional analysis of the individual enhancer core sequences of polyoma virus: cell-specific uncoupling of DNA replication from transcription," *Mol. Cell. Biol.*, 8:1993, 1988.

Campbell, In: *Monoclonal Antibody Technology, Laboratory Techniques in Biochemistry and Molecular Biology*, Vol. 13, Burden and Von Knippenberg, Eds. pp. 75–83, Amsterdam, Elseview, 1984.

Campere and Tilghman, "Postnatal repression of the α-fetoprotein gene is enhancer independent," *Genes and Dev.*, 3:537, 1989.

Campo, Spandidos, Lang, Wilkie, "Transcriptional control signals in the genome of bovine papilloma virus type 1," *Nature*, 303:77, 1983.

Capaldi, Bell, Branchek, "Changes in order of migration of polypeptides in complex III and cytochrome C oxidase under different conditions of SDS polyacrylamide gel electrophoresis," *Biochem. Biophys. Res. Comm.*, 76:425–433, 1977.

Celander and Haseltine, "Glucocorticoid regulation of murine leukemia virus transcription elements is specified by determinants within the viral enhancer region," *J. Virology*, 61:269, 1987.

Celander, Hsu, and Haseltine, "Regulatory Elements Within the Murine Leukemia Virus Enhancer Regions Mediate Glucocorticoid Responsiveness," *J. Virology*, 62:1314, 1988.

Chandler, Maler, and Yamamoto, "DNA Sequences Bound Specifically by Glucocorticoid Receptor in vitro Render a Heterlogous Promoter Hormone Responsive in vivo," *Cell*, 33:489, 1983.

Chang et al., "Foreign gene delivery and expression in hepatocytes using a hepatitis B virus vector", *Hepatology*, 14:124A, 1991.

Chang, Erwin, and Lee, "Glucose-regulated Protein (GRP94 and GRP78) Genes Share Common Regulatory Domains and are Coordinately Regulated by Common Trans-acting Factors," *Mol. Cell. Biol.*, 9:2153, 1989.

Chatterjee, Lee, Rentoumis, and Jameson, "Negative Regulation of the Thyroid-Stimulating Hormone Alpha Gene by Thyroid Hormone: Receptor Interaction Adjacent to the TATA Box," *Proc Nat'l Acad. Sci. U.S.A.*, 86:9114, 1989.

Chen and Okayama, "High-efficiency transfection of mammalian cells by plasmid DNA", *Mol. Cell Biol.*, 7:2745–2752, 1987.

Chen, Kerr, Chang, Honjo, Khalili, "Evidence for regulation of transcription and replication of the human neurotropic virus JCV genome by the human S9mu)bp-2 protein in glial cells," *Gene*, 185:55–62, 1997.

Choi, Chen, Kriegler, and Roninson, "An altered pattern of cross-resistance in multi-drug-resistant human cells results from spontaneous mutations in the mdr-1 (p-glycoprotein) gene," *Cell*, 53:519, 1988.

Clerk, A. & Sugden, P. H. (1999) *Am. J. Cardiol.* 83, 64H–69H.

Coffin, Retroviridae and Their Replication. In: *Virology*, Fields et al., eds., Raven Press, New York, pp. 1437–1500, 1990.

Cohen et al., "A repetitive sequence element 3' of the human c-Ha-ras1 gene has enhancer activity", *J. Cell. Physiol.*, 5:75, 1987

Cook et al., "In vitro splicing of the ribosomal RNA precursor of *Tetrahymena*: involvement of a guanosine nucleotide in the excision of the intervening sequence," *Cell*, 27:487–496, 1981.

Costa, Lai, Grayson, and Darnell, "The Cell-Specific Enhancer of the Mouse Transthyretin (Prealbumin) Gene Binds a Common Factor at One Site and a Liver-Specific Factor(s) at Two Other Sites," *Mol. Cell. Biol.*, 8:81, 1988.

Couch et al., "Immunization with types 4 and 7 adenovirus by selective infection of the intestinal tract," *Am. Rev. Resp. Dis.*, 88:394–403, 1963.

Coupar et al., "A general method for the construction of recombinant vaccinia virus expressing multiple foreign genes", *Gene*, 68:1–10, 1988.

Cripe, Haugen, Turk, Tabatabai, Schmid, Durst, Gissmann, Roman, and Turek, "Transcriptional Regulation of the Human Papilloma Virus-16 E6–E7 Promoter by a Keratinocyte-Dependent Enhancer, and by Viral E2 Trans-Activator and Repressor Gene Products: Implications for Cervical Carcinogenesis," *EMBO J.*, 6:3745, 1987.

Cui, Hagan, Zhang, Peltz, "Identification and characterization of genes that are required for the accelerated degradation of mRNAs containing a premature translational termination codon," *Genes Devel.*, 9:423–436, 1995.

Culotta and Hamer, "Fine Mapping of a Mouse Metallothionein Gene Metal-Response Element," *Mol. Cell. Biol.*, 9:1376, 1989.

Czaplinski, Weng, Hagan, Peltz, "Purification and characterization of the Upf1 protein: a factor involved in translation and mRNA degradation," *Rna*, 1:610–623, 1995.

Dandolo, Blangy, and Kamen, "Regulation of Polyma Virus Transcription in Murine Embryonal Carcinoma Cells," *J. Virology*, 47:55, 1983.

De la Cruz, Kressler, Linder, "Undwinding RNA in *Saccharomyces cerevisiae*, DEAD-box proteins and related families," *Trends in Biochem. Sciences*, 24:192–198, 1999.

Dehaan, In *Organogenesis*, Dehaan and Ursprung (Eds.), Holt, Rinehart & Winston, New York, 377–419, 1965.

DeMarini, Winey, Ursic, Webb, Culbertson, "SEN1, a positive effector of tRNA-splicing endonuclease in *Saccharomyces cerevisiae*," *Molecular Cellular Biol.*, 12:2154–2164, 1992.

Deschamps, Meijlink, and Verma, "Identification of a Transcriptional Enhancer Element Upstream From the Proto-Oncogene Fos," *Science*, 230:1174, 1985.

Dubensky et al., "Direct transfection of viral and plasmid DNA into the liver or spleen of mice", *Proc. Nat'l Acad. Sci. USA*, 81:7529–7533, 1984.

Edbrooke, Burt, Cheshire, and Woo, "Identification of cis-acting sequences responsible for phorbol ester induction of human serum amyloid a gene expression via a nuclear-factor-kappa β-like transcription factor," *Mol. Cell. Biol.*, 9:1908, 1989.

Edlund, Walker, Barr, and Rutter, "Cell-specific expression of the rat insulin gene: evidence for role of two distinct 5' flanking elements," *Science*, 230:912, 1985.

Edmondson, Lyons, Martin, Olson, "Mef2 gene expression marks the cardiac and skeletal muscle lineages during mouse embryogenesis," *Development*, 120:1251–1263, 1994.

European Patent App. No. 0273085

Fechheimer, Boylan, Parker, Sisken, Patel and Zimmer, "Transfection of mammalian cells with plasmid DNA by scrape loading and sonication loading," *Proc Nat'l. Acad. Sci. USA* 84:8463–8467, 1987

Feng and Holland, "HIV-I Tat Trans-Activation Requires the Loop Sequence Within Tar," *Nature*, 334:6178, 1988.

Ferkol et al., "Regulation of the phosphoenolpyruvate carboxykinase/human factor IX gene introduced into the livers of adult rats by receptor-mediated gene transfer", *FASEB J.*, 7:1081–1091, 1993.

Firak and Subramanian, "Minimal Transcription Enhancer of Simian Virus 40 is a 74-Base-Pair Sequence that Has Interacting Domains," *Mol. Cell. Biol.*, 6:3667, 1986.

Firulli, McFadden, Lin, Srivastava, Olson, "Heart and extra-embryonic mesodermal defects in mouse embryos lacking the bHLH transcription factor Hand1," *Nature Gene.*, 18:266–270.

Fishman and Olson, "Parsing the heart: genetic modules for organ assembly," *Cell*, 91:153–156, 1997.

Foecking and Hofstetter, "Powerful and Versatile Enhancer-Promoter Unit for Mammalian Expression Vectors," *Gene*, 45(1):101–105, 1986.

Forster and Symons, "Self-cleavage of plus and minus RNAs of a virusoid and a structural model for the active sites," *Cell*, 49:211–220, 1987.

Fraley, Fomari, Kaplan, "Entrapment of a bacterial plasmid in phospholipid vesicles:potential for gene transfer," *Proc Nat'l. Acad. Sci. USA* 76:3348–3352, 1979.

Franz, Brem, Katus, Klingel, Hofschneider, Kandolf, "Characterization of a cardiac-selective and developmentally upregulated promoter in transgenic mice," *Cardoscience*, 5(4):235–43, 1994.

Freifelder, *Physical Biochemistry Applications to Biochemistry and Molecular Biology*, 2nd ed. Wm. Freeman and Co., New York, N.Y., 1982.

Frey, N., Richardson, J. A., & Olson, E. N., *Proc. Nat'l Acad. Sci. USA* 97, 14632–14637, 2000.

Friedmann, "Progress toward human gene therapy", *Science*, 244:1275–1281, 1989.

Fujita, Shibuya, Hotta, Yamanishi, and Taniguchi, "Interferon-Beta Gene Regulation: Tandemly Repeated Sequences of a Synthetic 6-bp Oligomer Function as a Virus-Inducible Enhancer," *Cell*, 49:357, 1987.

Gefler, Margulies, Scharff, "A simple method for polyethylene glycol-promoted hybridization of mouse myeloma cells," *Somatic Cell Genet.*, 3:231–236, 1977.

Gerlach et al., "Construction of a plant disease resistance gene from the satellite RNA of tobacco rinspot virus," *Nature (London)*, 328:802–805, 1987.

Ghosh and Bachhawat, Targeting of Liposomes to Hepatocytes. In: *Liver Diseases, Targeted Diagnosis and Therapy Using Specific Receptors and Ligands*. Wu et al., eds., Marcel Dekker, New York, pp. 87–104, 1991.

Ghosh-Choudhury et al., "Protein IX, a minor component of the human adenovirus capsid, is essential for the packaging of full-length genomes," *EMBO J.*, 6:1733–1739, 1987.

Gilles, Morris, Oi, and Tonegawa, "A tissue-specific transcription enhancer element is located in the major intron of a rearranged immunoglobulin heavy-chain gene," *Cell*, 33:717, 1983.

Gloss, Bernard, Seedorf, and Klock, "The Upstream Regulatory Region of the Human Papilloma Virus-16 Contains an E2 Protein-Independent Enhancer Which is Specific for Cervical Carcinoma Cells and Regulated by Glucocorticoid Hormones," *EMBO J.*, 6:3735, 1987.

Godbout, Ingram, and Tilghman, "Fine-Structure Mapping of the Three Mouse Alpha-Fetoprotein Gene Enhancers," *Mol. Cell. Biol.*, 8:1169, 1988.

Goding, 1986, In: *Monoclonal Antibodies: Principles and Practice*, 2d ed., Academic Press, Orlando, Fla., pp. 60–61, and 71–74, 1986.

Gomez-Foix et al., "Adenovirus-mediated transfer of the muscle glycogen phosphorylase gene into hepatocytes confers altered regulation of glycogen," *J. Biol. Chem.*, 267:25129–25134, 1992.

Goodbourn and Maniatis, "Overlapping Positive and Negative Regulatory Domains of the Human β-Interferon Gene," *Proc. Nat'l Acad. Sci. USA*, 85:1447, 1988.

Goodbourn, Burstein, and Maniatis, "The Human Beta-Interferon Gene Enhancer is Under Negative Control," *Cell*, 45:601, 1986.

Gopal, "Gene transfer method for transient gene expression, stable transfection, and cotransfection of suspension cell cultures", *Mol. Cell Biol.*, 5:1188–1190, 1985.

Gopal-Srivastava, Haynes, Piatigorsky, "Regulation of the murine αβ-crystallin/small heat shock protein gene in cardiac muscle," *Muscle Cell. Biol.*, 15:7081–7090, 1995.

Graham and Prevec, In: *Methods in Molecular Biology: Gene Transfer and Expression Protocol*, E. J. Murray, ed., Humana Press, Clifton, N.J., 7:109–128, 1991.

Graham and van der Eb, "A new technique for the assay of infectivity of human adenovirus 5 DNA", *Virology*, 52:456–467, 1973.

Graham et al., "Characteristics of a human cell line transformed by DNA from human adenovirus type 5", *J. Gen. Virol.*, 36:59–72, 1977.

Greene, Bohnlein, and Ballard, "HIV-1, and Normal T-Cell Growth: Transcriptional Strategies and Surprises," *Immunology Today*, 10:272, 1989

Grosschedl and Baltimore, "Cell-Type Specificity of Immunoglobulin Gene Expression is Regulated by at Least Three DNA Sequence Elements," *Cell,* 41:885, 1985.

Grunhaus and Horwitz, "Adenovirus as cloning vector", *Seminar in Virology,* 3:237–252, 1992.

Gulley, Zhang, Gascoyne, DuPont, Banks, Cho, Huang, Montalvo, "Translocations of 11q13 in mantle cell lymphoma fail to disrupt the S mu bp-2 gene," *Hematopathology Molecular Hematology,* 11:1–11, 1997.

Han and Prywes, "Regulatory role of MEF2D in serum induction of the c-jun promoter," *Molecular Cellular Biology,* 15:2907–2915, 1995.

Harland and Weintraub, "Translation of mammalian mRNA injected into *Xenopus* oocytes is specifically inhibited by antisense RNA", *J. Cell Biol.,* 101: 1094–1099, 1985.

Harlow and Lane, Antibodies: A Laboratory manual, Cold Spring Harbor Laboratory, 1988.

Haslinger and Karin, "Upstream Promoter Element of the Human Metallothionein-II Gene Can Act Like an Enhancer Element," *Proc Nat'l Acad. Sci. U.S.A.,* 82:8572, 1985.

Hauber and Cullen, "Mutational Analysis of the Trans-Activation-Responsive Region of the Human Immunodeficiency Virus Type I Long Terminal Repeat," *J. Virology,* 62:673, 1988.

Hen, Borrelli, Fromental, Sassone-Corsi, and Chambon, "A Mutated Polyoma Virus Enhancer Which is Active in Undifferentiated Embryonal Carcinoma Cells is not Repressed by Adenovirus-2 E1A Products," *Nature,* 321: 249, 1986.

Hensel, Meichle, Pfizenmaier, and Kronke, "PMA-Responsive 5' Flanking Sequences of the Human TNF Gene," *Lymphokine Res.,* 8:347, 1989.

Hermonat and Muzycska, "Use of adenoassociated virus as a mammalian DNA cloning vector: Transduction of neomycin resistance into mammalian tissue culture cells", *Proc. Nat'l Acad. Sci. USA,* 81:6466–6470, 1984.

Hersdorffer et al., "Efficient gene transfer in live mice using a unique retroviral packaging line," *DNA Cell Biol.,* 9:713–723, 1990.

Herz and Gerard, "Adenovirus-mediated transfer of low density lipoprotein receptor gene acutely accelerates cholesterol clearance in normal mice," *Proc. Nat'l. Acad. Sci. USA* 90:2812–2816, 1993.

Hirochika, Browker, and Chow, "Enhancers and Trans-Acting E2 Transcriptional Factors of Papilloma Viruses," *J. Virol.,* 61:2599, 1987.

Hirsch, Gaugler, Deagostini-Bauzin, Bally-Cuif, and Gordis, "Identification of Positive and Negative Regulatory Elements Governing Cell-Type-Specific Expression of the Neural-Cell-Adhesion-Molecule Gene," *Mol. Cell. Biol.,* 10: 1959, 1990.

Holbrook, Gulino, and Ruscetti, "cis-Acting Transcriptional Regulatory Sequences in the Gibbon Ape Leukemia Virus (GALV) Long Terminal Repeat," *Virology,* 157:211, 1987.

Horlick and Benfield, "The Upstream Muscle-Specific Enhancer of the Rat Muscle Creatine Kinase Gene is Composed of Multiple Elements," *Mol. Cell. Biol.,* 9:2396, 1989.

Horwich, et al., "Synthesis of hepadnavirus particles that contain replication-defective duck hepatitis B virus genomes in cultured HuH7 cells", *J. Virol.,* 64:642–650, 1990.

Huang et al, "A cellular protein that competes with SV40 antigen for binding to the retinoblastoma gene product," *Nature,* 350:160–162, 1991.

Hug, Costas, Staeheli, Aebi, and Weissmann, "Organization of the Murine Mx Gene and Characterization of its Interferon- and Virus-Inducible Promoter," *Mol. Cell. Biol.,* 8:3065, 1988.

Hwang, Lim, and Chae, "Characterization of the S-Phase-Specific Transcription Regulatory Elements in a DNA-Replication-Independent Testis-Specific H2B (TH2B) Histone Gene," *Mol. Cell. Biol.,* 10:585, 1990.

Imagawa, Chiu, and Karin, "Transcription Factor AP-2 Mediates Induction by Two Different Signal-Transduction Pathways: Protein Kinase C and cAMP," *Cell,* 51:251, 1987.

Imbra and Karin, "Phorbol Ester Induces the Transcriptional Stimulatory Activity of the SV40 Enhancer," *Nature,* 323:555, 1986.

Imler, Lemaire, Wasvlyk, and Waslyk, "Negative Regulation Contributes to Tissue Specificity of the Immunoglobulin Heavy-Chain Enhancer," *Mol. Cell. Biol,* 7:2558, 1987.

Imperiale and Nevins, "Adenovirus 5 E2 Transcription Unit: an E1A-Inducible Promoter with an Essential Element that Functions Independently of Position or Orientation," *Mol. Cell. Biol.,* 4:875, 1984.

Innis et al., "DNA sequencing with *Thermus aquaticus* DNA polymerase and direct sequencing of polymerase chain reaction-amplified DNA," *Proc Natl Acad Sci USA.* 85(24):9436–9440, 1988.

Jakobovits, Smith, Jakobovits, and Capon, "A Discrete Element 3' of Human Immunodeficiency Virus 1 (HIV-1) and HIV-2 mRNA Initiation Sites Mediates Transcriptional Activation by an HIV Trans-Activator," *Mol. Cell. Biol.,* 8:2555, 1988.

Jameel and Siddiqui, "The Human Hepatitis B Virus Enhancer Requires Transacting Cellular Factor(s) for Activity," *Mol. Cell. Biol.,* 6:710, 1986.

Jaynes, Johnson, Buskin, Gartside, and Hauschka, "The Muscle Creatine Kinase Gene is Regulated by Multiple Upstream Elements, Including a Muscle-Specific Enhancer," *Mol. Cell. Biol.,* 8:62, 1988.

Johnson et al., Peptide Turn Mimetics" IN: *Biotechnology And Pharmacy,* Pezzuto et al., eds., Chapman and Hall, New York, 1993.

Johnson, Wold, and Hauschka, "Muscle creatine kinase sequence elements regulating skeletal and cardiac muscle expression in transgenic mice," *Mol. Cell. Biol.,* 9:3393, 1989.

Jones and Shenk, "Isolation of deletion and substitution mutants of adenovirus type 5," *Cell,* 13:181–188, 1978.

Joyce, "RNA evolution and the origins of life," *Nature,* 338:217–244, 1989.

Kadesch and Berg, "Effects of the Position of the Simian Virus 40 Enhancer on Expression of Multiple Transcription Units in a Single Plasmid," *Mol Cell. Biol.,* 6:2593, 1986.

Kaneda et al., "Increased expression of DNA cointroduced with nuclear protein in adult rat liver", *Science,* 243: 375–378, 1989.

Karin, Haslinger, Heguy, Dietlin, and Cooke, "Metal-Responsive Elements Act as Positive Modulators of Human Metallothionein-IIA Enhancer Activity," *Mol. Cell. Biol.,* 7:606, 1987.

Karlsson et al, *EMBO J,* 5:2377–2385, 1986.

Katinka, Vasseur, Montreau, Yaniv, and Blangy, "Polyoma DNA Sequences Involved in the Control of Viral Gene Expression in Murine Embryonal Carcinoma Cells," *Nature,* 290:720, 1981.

Katinka, Yaniv, Vasseur, and Blangy, "Expression of Polyoma Early Functions in Mouse Embryonal Carcinoma Cells Depends on Sequence Rearrangements in the Beginning of the Late Region," *Cell,* 20:393, 1980.

Kato et al., "Expression of hepatitis β virus surface antigen in adult rat liver. Co-introduction of DNA and nuclear protein by a simplified liposome method," *J Biol. Chem.,* 266(6):3361–3364, 1991.

Kawamoto, Makino, Niw, Sugiyama, Kimura, Anemura, Nakata, and Kakunaga, "Identification of the Human Beta-Actin Enhancer and its Binding Factor," *Mol. Cell. Biol.,* 8:267, 1988.

Kelly, Alonso, Tajbakhsh, Cossu, Buckingham, "Myosin light chain 3F regulatory sequences confer regionalized cardiac and skeletal muscle expression in transgenic mice," *J. Cell Biol.,* 129(2):383–96, 1995.

Kiledjian, Su, Kadesch, "Identification and characterization of two functional domains within the murine heavy-chain enhancer," *Mol. Cell. Biol.,* 8:145, 1988.

Kim and Cook, "Three dimensional model of the active site of the self-splicing rRNA precursor or Tetrahymena," *Proc. Nat'l Acad. Sci. USA,* 84:8788–8792, 1987.

Kim, Choe, Seo, "The sen1(+) gene of *Schizosaccharomyces pombe*, a homologue of budding yeast SEN1, encodes an RNA and DNA helicase," *Biochemistry,* 38:14697–14710, 1999.

Kimura, Abe, Suzuki, Ogawa, Yoshioka, Kaname, Miike, Yamamura, "A 900 bp genomic region from the mouse dystrophin promoter directs lacZ reporter expression only to the right heart of transgenic mice," *Dev. Growth Differ.,* 39(3):257–65, 1997.

Klamut, Gangopadyhay, Worton, and Ray, "Molecular and Functional Analysis of the Muscle-Specific Promoter Region of the Duchenne Muscular Dystrophy Gene," *Mol. Cell. Biol.,* 10:193, 1990.

Klein et al., "High-velocity microprojectiles for delivering nucleic acids into living cells", *Nature,* 327:70–73, 1987.

Koch, Benoist, and Mathis, "Anatomy of a new β-cell-specific enhancer," *Mol. Cell. Biol.,* 9:303, 1989.

Kohler and Milstein, "Continuous cultures of fused cells secreting antibody of predefined specificity," *Nature,* 256: 495–497, 1975.

Kohler and Milstein, "Derivation of specific antibody-producing tissue culture and tumor lines by cell fusion," *Eur. J. Immunol.,* 6:511–519, 1976.

Kriegler and Botchan, "Enhanced transformation by a simian virus 40 recombinant virus containing a Harvey murine sarcoma virus long terminal repeat," *Mol. Cell. Biol.* 3:325, 1983.

Kriegler and Botchan, *In: Eukaryotic Viral Vectors,* Y. Gluzman, ed., Cold Spring Harbor: Cold Spring Harbor Laboratory, NY, 1982.

Kriegler et al., "Promoter substitution and enhancer augmentation increases the penetrance of the sv40 a gene to levels comparable to that of the harvey murine sarcoma virus ras gene in morphologic transformation," *In: Gene Expression,* Alan Liss (Ed.), Hamer and Rosenberg, New York, 1983.

Kriegler et al., "Transformation Mediated by the SV40 T Antigens: Separation of the Overlapping SV40 Early Genes with a Retroviral Vector," *Cell,* 38:483, 1984.

Kriegler et al., "Viral Integration and Early Gene Expression Both Affect the Efficiency of SV40 Transformation of Murine Cells: Biochemical and Biological Characterization of an SV40 Retrovirus," In: *Cancer Cells 2/Oncogenes and Viral Genes,* Van de Woude et al. eds, Cold Spring Harbor: Cold Spring Harbor Laboratory, 1984.

Kriegler, Perez, Defay, Albert and Liu, "A Novel Form of TNF/Cachectin Is a Cell-Surface Cytotoxix Transmembrane Protein: Ramifications for the Complex Physiology of TNF," *Cell,* 53:45, 1988.

Kuhl, De La Fuenta, Chaturvedi, Parinool, Ryals, Meyer, and Weissman, "Reversible Silencing of Enhancers by Sequences Derived From the Human IFN-alpha Promoter," *Cell,* 50:1057, 1987.

Kuisk, Li, Tran, Capetanaki, "A single MEF2 site governs desmin transcription in both heart and skeletal muscle during mouse embryogenesis," *Developmental Biology,* 174:1–13, 1996.

Kunz, Zimmerman, Heisig, and Heinrich, "Identification of the Promoter Sequences Involved in the Interleukin-6-Dependent Expression of the Rat Alpha-2-Macroglobulin Gene," *Nucl. Acids Res.,* 17:1121, 1989.

Kuo, Morrisey, Anandappa, Sigrist, Lu, Parmacek, Soudais, Leiden, "GATA4 transcription factor is required for ventral morphogenesis and heart tube formation," *Genes Development,* 11:1048–1060, 1997.

Kyte and Doolittle, "A simple method for displaying the hydropathic character of a protein," *J. Mol. Biol.,* 157(1): 105–132, 1982.

LaPointe, Wu, Greenberg, Gardner, "Upstream sequences confer atrial-specific expression on the human atrial natriuretic factor gene." *J. Biol. Chem.,* 263(19):9075–8, 1988.

Larsen, Harney, and Moore, "Repression medaites cell-type-specific expression of the rat growth hormone gene," *Proc Nat'l Acad. Sci. USA.,* 83:8283, 1986.

Laspia, Rice, and Mathews, "HIV-1 Tat protein increases transcriptional initiation and stabilizes elongation," *Cell,* 59:283, 1989.

Latimer, Berger, and Baumann, "Highly conserved upstream regions of the $\alpha_1$-antitrypsin gene in two mouse species govern liver-specific expression by different mechanisms," *Mol. Cell. Biol.,* 10:760, 1990.

Le Gal La Salle et al., "An adenovirus vector for gene transfer into neurons and glia in the brain," *Science,* 259:988–990, 1993.

Lee, Mulligan, Berg, and Ringold, "Glucocorticoids Regulate Expression of Dihydrofolate Reductase cDNA in Mouse Mammary Tumor Virus Chimaeric Plasmids," *Nature,* 294:228, 1981.

Leeds, Peltz, Jacobson, Culbertson, "The product of the yeast UPF1 gene is required for rapid turnover of mRNAs containing a premature translational termination codon," *Genes Development,* 5:2303–2314, 1991.

Lelivelt and Culbertson, "Yeast Upf proteins required for RNA surveillance affect global expression of the eyast transcriptome," *Molecular Cellular Biology,* 19:6710–6719, 1999.

Levinson, Khoury, VanDeWoude, and Gruss, "Activation of SV40 Genome by 72-Base-Pair Tandem Repeats of Moloney Sarcoma Virus," *Nature,* 295:79, 1982.

Levrero et al., "Defective and nondefective adenovirus vectors for expressing foreign genes in vitro and in vivo," *Gene,* 101:195–202, 1991.

Li, J. M. & Grooks, G., *Eur. Heart J* 20, 406–420, 1999.

Lilly, Galewsky, Firulli, Schulz, Olson, "D-MEF2: a MADs box transcription factor expressed in differentiating mesoderm and muscle cell lineages during *Drosophila* embryogenesis," *Proc. Nat'l Acad. Sci. USA,* 91:5662–5666, 1994.

Lilly, Zhao, Ranganayakulu, Paterson, Schulz, Olson "Requirement of MADS domain transcription factor D-MEF2 for muscle formation in *Drosophila,*" *Science,* 267:688–693, 1995.

Lin, Cross, Halden, Dragos, Toledano, and Leonard, "Delineation of an enhancer like positive regulatory element in the interleukin-2 receptor α-chain gene," *Mol. Cell. Biol.*, 10:850, 1990.

Lin, Schwarz, Bucana, Olson, "Control of mouse cardiac morphogenesis and myogenesis by transcription factor MEF2C," *Science*, 276:1404–1407, 1997.

Liu, Z. P., Nakagawa, O., Nakagawa, M., Yanagisawa, H., Passier, R., Richardson, J. A., Srivastava, D., & Olson, E. N. *Dev. Biol.* 234, 497–509, 2001.

Luria, Gross, Horowitz, and Givol, "Promoter Enhancer Elements in the Rearranged Alpha-Chain Gene of the Human T-Cell Receptor," *EMBO J.*, 6:3307, 1987.

Lusky and Botchan, "Transient Replication of Bovine Papilloma Virus Type 1 Plasmids: cis and trans Requirements," *Proc Nat'l Acad. Sci. U.S.A.*, 83:3609, 1986.

Lusky, Berg, Weiher, and Botchan, "Bovine Papilloma Virus Contains an Activator of Gene Expression at the Distal End of the Early Transcription Unit," *Mol. Cell. Biol.* 3:1108, 1983.

Macejak and Sarnow, "Internal initiation of translation mediated by the 5' leader of a cellular mRNA," *Nature*, 353:90–94, 1991.

Majors and Varmus, "A Small Region of the Mouse Mammary Tumor Virus Long Terminal Repeat Confers Glucocorticoid Hormone Regulation on a Linked Heterologous Gene," *Proc. Nat'l Acad. Sci. USA*, 80:5866, 1983.

Manipulating the Mouse Embryo: A Laboratory Manual, 2nd ed., Hogan et al., eds., Cold Spring Harbor Laboratory Press, 1994.

Mann et al., "Construction of a retrovirus packaging mutant and its use to produce helper-free defective retrovirus", *Cell*, 33:153–159, 1983.

Markowitz et al., "A safe packaging line for gene transfer: Separating viral genes on two different plasmids," *J. Virol.*, 62:1120–1124, 1988.

McNeall, Sanchez, Gray, Chesterman, and Sleigh, "Hyperinducible Gene Expression From a Metallotionein Promoter Containing Additional Metal-Responsive Elements," *Gene*, 76:81, 1989.

Merrifield, "Solid phase synthesis," *Science*, 232: 341–347, 1986.

Michel and Westhof, "Modeling of the three-dimensional architecture of group I catalytic introns based on comparative sequence analysis," *J. Mol. Biol.*, 216:585–610, 1990.

Miksicek, Heber, Schmid, Danesch, Posseckert, Beato, and Schutz, "Glucocorticoid Responsiveness of the Transcriptional Enhancer of Moloney Murine Sarcoma Virus," *Cell*, 46:203, 1986.

Molkentin and Olson, "GATA4: a novel transcriptional regulator of cardiac hypertrophy?" *Circulation*, 96:3833–3835, 1997.

Molkentin, J. D., Lu, J. R., Antos, C. L., Markham, B., Richardson, J., Robbins J., Grant, S. R., & Olson, E. N. (1998) *Cell* 93, 215–228.

Mordacq and Linzer, "Co-localization of Elements Required for Phorbol Ester Stimulation and Glucocorticoid Repression of Proliferin Gene Expression," *Genes and Dev.*, 3:760, 1989.

Moreau, Hen, Wasylyk, Everett, Gaub, and Chambon, "The SV40 base-repair repeat has a striking effect on gene expression both in sv40 and other chimeric recombinants," *Nucl. Acids Res.*, 9:6047, 1981.

Moss, Marshall, Moczydlowski, "Hypothesis for a serine proteinase-like domain at the COOH terminus of Slowpoke calcium-activated potassium channels," *J. Gen. Physiol.*, 108(6):473–84, 1996.

Musesing, Smith, and Capon, "Regulation of mRNA Accumulation by a Human Immunodeficiency Virus Trans-Activator Protein," *Cell*, 48:691, 1987.

Nakagawa, Nakagawa, Richardson, Olson, Srivastava, "HRT1, HRT2, and HRT3: a new subclass of bHLH transcription factors marking specific cardiac, somitic, and pharyngeal arch segment,"*Develop. Biol.*, 216:72–84, 1999.

Nakajima, Uchida, Anderson, Lee, Hurwitz, Parvin, Montminy, "RNA helicase A mediates association of CBP with RNA polymerase II," *Cell*, 90:1107–1112, 1997.

Naya and Olson, "MEF2: a transcriptional target for signaling pathways controlling skeletal muscle growth and differentiation," *Curr. Opinion Cell Biol.*, 11:683–688, 1999.

Ng, Gunning, Liu, Leavitt, and Kedes, "Regulation of the Human Beta-Actin Promoter by Upstream and Intron Domains," *Nuc. Acids Res.*, 17:601, 1989.

Nguyen, Bodmer, Abmayr, McDermott, Spoerel, "D-mef2: a Drosophila mesoderm-specific MADS box-containing gene with a biphasic expresssion profile during embryogenesis," *Proc. Nat'l Acad. Sci. USA*, 91:7520–7524, 1994.

Nicol, R. L., Frey, N., Pearson, G., Cobb, M., Richardson, J., & Olson, E. N., *EMBO J.* 20, 2757–2767, 2001.

Nicolas and Rubinstein, In: *Vectors: A survey of molecular cloning vectors and their uses*, Rodriguez and Denhardt, eds., Stoneham: Butterworth, pp. 494–513, 1988.

Nicolau and Sene, "Liposome-mediated DNA transfer in eukaryotic cells", *Biochim. Biophys. Acta*, 721:185–190, 1982.

Nicolau et al., "Liposomes as carriers for in vivo gene transfer and expression," *Methods Enzymol.*, 149:157–176, 1987.

Nozato, T., Ito, H., Watanabe, M., Ono, Y., Adachi, S., Tanaka, H., Hiroe, M., Sunamori, M., & Marum, F., *J. Mol. Cell. Cardiol.* 33, 1493–1504, 2000.

Olson and Srivastava, "Molecular pathways controlling heart development," *Science*, 272:671–676, 1996.

Ondek, Sheppard, and Herr, "Discrete Elements Within the SV40 Enhancer Region Display Different Cell-Specific Enhancer Activities," *EMBO J.*, 6:1017, 1987.

Ornitz, Hammer, Davison, Brinster, and Palmiter, "Promoter and enhancer elements from the rat elastase i gene function independently of each other and of heterologous enhancers," Mol. Cell. Biol. 7:3466, 1987.

Palmiter, Chen, and Brinster, "Differential regulation of metallothionein-thymidine kinase fusion genes in transgenic mice and their offspring," *Cell*, 29:701, 1982.

Paskind et al., "Dependence of moloney murine leukemia virus production on cell growth", *Virology*, 67:242–248, 1975.

Passier, Xheng, Frey, Naya, Nicol, McKinsey, Overbeek, Richardson, Grant, Olson, "CaM kinase signaling induces cardiac hypertrophy and activates the MEF2 transcription factor in vivo," *J. Clin. Invest.*, 105(10):1395–406, 2000.

Pech, Rao, Robbins, and Aaronson, "Functional identification of regulatory elements within the promoter region of platelet-derived growth factor 2," *Mol. Cell. Biol.*, 9:396, 1989.

Pelletier and Sonenberg, "Internal initiation of translation of eukaryotic mRNA directed by a sequence derived from poliovirus RNA," *Nature*, 334:320–325, 1988.

Perales, Ferkol, Beegen, Ratnoff, Hanson, "Gene transfer in vivo: sustained expression and regulation of genes introduced into the liver by receptor-targeted uptake," *Proc. Nat'l Acad. Sci. USA,* 91(9):4086–4090, 1994.

Perez-Stable and Constantini, "Roles of fetal γ-globin promoter elements and the adult β-globin 3' enhancer in the stage-specific expression of globin genes," *Mol. Cell. Biol.,* 10:1116, 1990.

Picard and Schaffner, "A lymphocyte-specific enhancer in the mouse immunoglobulin kappa gene," *Nature,* 307:83, 1984.

Pignon, Vinatier, Fanen, Jonveaux, Tournilhac, Imbert, Rochant, Goossens, "Exhaustive analysis of the P53 gene coding sequence by denaturing gradient gel electrophoresis: application to the detection of point mutations in acute leukemias," *Hum. Mutat.,* 3: 126–132, 1994.

Pinkert, Omitz, Brinster, and Palmiter, "An albumin enhancer located 10 kb upstream functions along with its promoter to direct efficient, liver-specific expression in transgenic mice," *Genes and Dev.,* 1:268, 1987.

Ponta, Kennedy, Skroch, Hynes, and Groner, "Hormonal Response Region in the Mouse Mammary Tumor Virus Long Terminal Repeat Can Be Dissociated From the Proviral Promoter and Has Enhancer Properties," *Proc. Nat'l Acad. Sci. U.S.A.,* 82:1020, 1985.

Porton, Zaller, Lieberson, and Eckhardt, "Immunoglobulin heavy-chain enhancer is required to maintain transfected .gamma.2a gene expression in a pre-b-cell line," *Mol. Cell. Biol.,* 10:1076, 1990.

Potter et al., "Enhancer-dependent expression of human k immunoglobulin genes introduced into mouse pre-B lymphocytes by electroporation," *Proc. Nat'l Acad. Sci. USA,* 81:7161–7165, 1984.

Queen and Baltimore, "Immunoglobulin gene transcription is activated by downstream sequence elements," *Cell,* 35:741, 1983.

Quinn, Farina, Gardner, Krutzsch, and Levens, "Multiple components are required for sequence recognition of the ap1 site in the gibbon ape leukemia virus enhancer," *Mol. Cell. Biol.,* 9:4713, 1989.

Racher et al., *Biotechnology Techniques,* 9:169–174, 1995.

Ragot et al., "Efficient adenovirus-mediated transfer of a human minidystrophin gene to skeletal muscle of mdx mice," *Nature,* 361:647–650, 1993.

Ranganayakulu, Zhao, Dokidis, Molentin, Olson, Schulz, "A series of mutations in the D-MEF2 transcription factor reveal multiple functions in larval and adult myogenesis in *Drosophila, Dev. Biology,* 171:169–181, 1995.

Redondo, Hata, Brocklehurst, and Krangel, "A T-Cell-Specific Transcriptional Enhancer Within the Human T-Cell Receptor delta Locus," *Science,* 247:1225, 1990.

Reinhold-Hurek and Shub, "Self-splicing introns in tRNA genes of widely divergent bacteria," *Nature,* 357:173–176, 1992.

Reisman and Rotter, "Induced expression from the moloney murine leukemia virus long terminal repeat during differentiation of human myeloid cells is mediated through its transcriptional enhancer," *Mol. Cell. Biol.,* 9:3571, 1989.

Reiter, Alexander, Rodaway, Yelon, Pateint, Holder, Stainer, "Gata5 is required for the development of theart and endoderm in zebrafish," *Genes Develop.,* 13:2983–2995, 1999.

Renan, "Cancer genes: Current status, future prospects and applications in radiotherapyloncology," *Radiother. Oncol.,* 19:197–218, 1990.

Resendez Jr., Wooden, and Lee, "Identification of highly conserved regulatory domains and protein-binding sites in the promoters of the rat and human genes encoding the stress-inducible 78-kilodalton glucose-regulated protein," *Mol. Cell. Biol.,* 8:4579, 1988.

Rich et al., "Development and analysis of recombinant adenoviruses for gene therapy of cystic fibrosis," *Hum. Gene Ther.,* 4:461–476, 1993

Ridgeway, Mammalian Expression Vectors, In: *Vectors: A Survey of Molecular Cloning Vectors and Their Uses,* Rodriguez et al., eds., Stoneham: Butterworth, pp. 467492, 1988.

Ripe, Lorenzen, Brenner, and Breindl, "Regulatory elements in the 5' flanking region and the first intron contribute to transcriptional control of the mouse alpha-1-type collagen gene," *Mol. Cell. Biol.,* 9:2224, 1989.

Rippe, Brenner and Leffert, "DNA-mediated gene transfer into adult rat hepatocytes in primary culture," *Mol. Cell Biol.,* 10:689–695, 1990.

Rittling, Coutinho, Amarm, and Kolbe, "AP-1/jun-binding Sites Mediate Serum Inducibility of the Human Vimentin Promoter," *Nuc. Acids Res.,* 17:1619, 1989.

Rosen, Sodroski, and Haseltine, "The location of cis-acting regulatory sequences in the human t-cell lymphotropic virus type III (HTLV-111/LAV) long terminal repeat," *Cell,* 41:813, 1988.

Rosenfeld, Siegfried, Yoshimura, Yoneyama, Fukayama, Stier, Paakko, Gilardi, Stratford-Perricaudet, Perricaudet, Jallat, Pavirani, Lecocq, Crystal, "Adenovirus-mediated transfer of a recombinant α1-antitrypsin gene to the lung epithelium in vivo," *Science,* 252:431–434, 1991.

Rosenfeld, Yoshimura, Trapnell, Yoneyama, Rosenthal, Dalemans, Fukayama, Bargon, Stier, Stratford-Perricaudet, Perricaudet, Guggino, Pavirani, Lecocq, Crystal, "In vivo transfer of the human cystic fibrosis transmembrane conductance regulator gene to the airway epithelium," *Cell,* 68:143–155, 1992.

Ross, Navankasattusas, Harvey, Chien, "An HF-1a/HF-1b/MEF-2 combinatorial element confers cardiac ventricular specificity and established an anterior-posterior gradient of expression," *Development,* 122:1799–1809, 1996.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses", *Proc. Nat'l Acad. Sci. USA,* 86:9079–9083, 1989.

Sakai, Helms, Carlstedt-Duke, Gustafsson, Rottman, and Yamamoto, "Hormone-Mediated Repression: A Negative Glucocorticoid-Response Element From the Bovine Prolactin Gene," *Genes and Dev.,* 2:1144, 1988.

Sambrook, Fritsch, Maniatis, *Molecular Cloning: A Laboratory Manual,* 2nd Ed., Cold Spring Harbor Press, Cold Spring Harbor, N.Y., 1989.

Sarver, et al, "Ribozymes as potential anti-HIV-1 therapeutic agents," *Science,* 247:1222–1225, 1990.

Satake, Furukawa, and Ito, "Biological activities of oligonucleotides spanning the f9 point mutation within the enhancer region of polyoma virus DNA," *J. Virology,* 62:970, 1988.

Scanlon et al., "Ribozyme-mediated cleavages of c-fos mRNA reduce gene expression of DNA synthesis enzymes and metallothionein," *Proc. Nat'l Acad. Sci. USA,* 88:10591–10595, 1991.

Schaffner, Schirm, Muller-Baden, Wever, and Schaffner, "Redundancy of Information in Enhancers as a Principle of Mammalian Transcription Control," *J. Mol. Biol.,* 201:81, 1988.

Searle, Stuart, and Palmiter, "Building a metal-responsive promoter with synthetic regulatory elements," *Mol. Cell. Biol.,* 5:1480, 1985.

Sebastiani, Durocher, Gros, Nemer, Malo, "Localization of the Catfl transcription factor gene to mouse chromosome 19," *Mammalian Genome,* 6:147–148, 1995.

Sedmera, D., Pexieder, T., Vuillemin, M., Thompson, R. P., & Anderson, R. H., *Anat. Rec.* 258, 319–337, 2000.

Sharp and Marciniak, "HIV Tar: an RNA Enhancer?," *Cell,* 59:229, 1989.

Shaul and Ben-Levy, "Multiple Nuclear Proteins in Liver Cells are Bound to Hepatitis B Virus Enhancer Element and its Upstream Sequences," *EMBO J.,* 6:1913, 1987.

Sherman, Basta, Moore, Brown, and Ting, "Class II Box Consensus Sequences in the HLA-DRα. Gene: Transcriptional Function and Interaction with Nuclear Proteins," *Mol. Cell. Biol.,* 9:50, 1989. Siomi and Dreyfuss, "RNA-binding proteins as regulators of gene expression," *Curr. Opinion Genetics Dev.,* 7:345–353, 1997.

Sleigh and Lockett, "SV40 Enhancer Activation During Retinoic-Acid-Induced Differentiation of F9 Embryonal Carcinoma Cells," *J. EMBO,* 4:3831, 1985.

Spalholz, Yang, and Howley, "Transactivation of a Bovine Papilloma Virus Transcriptional Regulatory Element by the E2 Gene Product," Cell, 42:183, 1985.

Spandau and Lee, "Trans-Activation of Viral Enhancers by the Hepatitis B Virus X Protein," *J. Virology,* 62:427, 1988.

Spandidos and Wilkie, "Host-Specificities of Papilloma Virus, Moloney Murine Sarcoma Virus and Simian Virus 40 Enhancer Sequences," *EMBO J.,* 2:1193, 1983.

Srivastava, "HAND proteins: molecular mediators of cardiac development and congenital heart disease," *Trends in Cardiovascular Medicine,* 9:11–18, 1999.

Srivastava, Cserjesi, Olson, "A subclass of bHLH proteins required for cardiac morphogenesis, *Sciences,* 270:1995–1999, 1995.

Srivastava, Thomas, Lin, Kirby, Brown, Olson, "Regulation of cardiac mesodermal and neural crest development by the bHLH transcription factor, dHAND," *Nature Genetics,* 16:5477–5490, 1996.

Stephens and Hentschel, "The Bovine Papilloma Virus Genome and its Uses as a Eukaryotic Vector," *Biochem. J,* 248:1, 1987.

Stewart and Young, Solid Phase Peptide Synthesis, 2d. ed., Pierce Chemical Co., 1984.

Stratford-Perricaudet and Perricaudet, Gene transfer into animals: the promise of adenovirus. In: *Human Gene Transfer,* O. Cohen-Haguenauer et al., eds., John Libbey Eurotext, France, pp. 51–61, 1991.

Stratford-Perricaudet et al., "Evaluation of the transfer and expression in mice of an enzyme-encoding gene using a human adenovirus vector", *Hum. Gene. Ther.,* 1:241–256, 1990.

Stuart, Searle, and Palmiter, "Identification of Multiple Metal Regulatory Elements in Mouse Metallothionein-I Promoter by Assaying Synthetic Sequences," *Nature,* 317:828, 1985.

Sullivan and Peterlin, "Transcriptional Enhancers in the HLA-DQ Subregion," *Mol. Cell. Biol.,* 7:3315, 1987.

Swartzendruber and Lehman, "Neoplastic Differentiation: Interaction of Simian Virus 40 and Polyoma Virus with Murine Teratocarcinoma Cells," *J. Cell. Physiology,* 85:179, 1975 Takebe et al., *Mol. Cell. Biol.,* 8:466, 1988.

Tam et al., *J. Am. Chem. Soc.,* 105:6442, 1983.

Tang et al., "A novel Gonadotropin-regulated Testicular RNA Helicase," *J. Biol. Chem.* 274:37932–37940, 1999.

Tavernier, Gheysen, Duerinck, Can Der Heyden, and Fiers, "Deletion Mapping of the Inducible Promoter of Human IFN-beta Gene," *Nature,* 301:634, 1983.

Taylor and Kingston, "E1A Trans-Activation of Human HSP70 Gene Promoter Substitution Mutants is Independent of the Composition of Upstream and TATA Elements," *Mol. Cell. Biol.,* 10:176, 1990.

Taylor and Kingston, "Factor Substitution in a Human HSP70 Gene Promoter: TATA-Dependent and TATA-Independent Interactions," *Mol. Cell. Biol.,* 10:165, 1990a.

Taylor, Solomon, Weiner, Paucha, Bradley, and Kingston, "Stimulation of the Human Heat-Shock Protein 70 Promoter in vitro by Simian Virus 40 Large T Antigen," *J. Biol. Chem.,* 264:15160, 1989.

Temin, Retrovirus vectors for gene transfer: Efficient integration into and expression of exogenous DNA in vertebrate cell genome. In: *Gene Transfer,* Kucherlapati R, ed., New York, Plenum Press, pp. 149–188, 1986.

Thiesen, Bosze, Henry, and Charnay, "A DNA Element Responsible for the Different Tissue Specificities of Friend and Moloney Retroviral Enhancers," *J. Virology,* 62:614, 1988.

Top et al., "Immunization with live types 7 and 4 adenovirus vaccines. II. Antibody response and protective effect against acute respiratory disease due to adenovirus type 7," *J. Infect. Dis.* 124:155–160, 1971.

Treisman, "Transient Accumulation of c-fos RNA Following Serum Stimulation Requires a Conserved 5' Element and c-fos 3' Sequences," *Cell,* 42:889, 1986.

Tronche, Rollier, Herbomel, Bach, Cereghini, Weiss, and Yaniv, "Anatomy of the Rat Albumin Promoter," *Mol. Biol. Med.,* 7:173, 1990.

Tur-Kaspa, Teicher, Levine, Skoultchi and Shafritz, "Use of electroporation to introduce biologically active foreign genes into primary rat hepatocytes," *Mol. Cell Biol.,* 6:716–718, 1986.

Tyndall, La Mantia, Thacker, Favaloro, and Kamen, "A Region of the Polyoma Virus Genome Between the Replication Origin and Late Protein-Coding Sequences is Required in cis for Both Early Gene Expression and Viral DNA Replication," *Nuc. Acids. Res.,* 9:6231, 1981.

Vannice and Levinson, "Properties of the Human Hepatitis B Virus Enhancer: Position Effects and Cell-Type Non-specificity," *J. Virology,* 62:1305, 1988.

Varmus etal., *Cell,* 25:23–36, 1981.

Vasseur, Kress, Montreau, and Blangy, "Isolation and Characterization of Polyoma Virus Mutants Able to Develop in Multipotential Murine Embryonal Carcinoma Cells," *Proc Nat'l Acad. Sci. U.S.A.,* 77:1068, 1980.

Von Harsdorf, R., Hauck, L., Mehrhof, F., Wegenka, U., Cardoso, M. C. & Deitz, R. *Cir. Res.* 85, 128–136, 1999.

Wagner, Zenke, Cotten, Beug, Birnstiel, "Transferrin-polycation conjugates as carriers for DNA uptake into cells," *Proc. Nat'l Acad. Sci. USA* 87(9):3410–3414, 1990.

Wang and Calame, "SV40 enhancer-binding factors are required at the establishment but not the maintenance step of enhancer-dependent transcriptional activation," *Cell,* 47:241, 1986.

Weber, De Villiers, and Schaffner, "An SV40 'Enhancer Trap' Incorporates Exogenous Enhancers or Generates Enhancers From its Own Sequences," *Cell,* 36:983, 1984.

Weinberger, Jat, and Sharp, "Localization of a Repressive Sequence Contributing to B-cell Specificity in the Immunoglobulin Heavy-Chain Enhancer," *Mol. Cell. Biol.,* 8:988, 1984.

Weng, Czaplinski, Peltz, "Genetic and biochemical characterization of mutations in the ATPase and helicase regions of the Upf1 protein," *Molecular Cellular Biol.*, 16:154–160, 1996.

Wilson-Rawls, Molkentin, Black, Olson, "Activated notch inhibits myogenic activity of the MADS-Box taqnscritpion factor myocyte enhancer factor 2C," *Molecular Cellular Biology*, 19:2853–2862, 1999.

Winoto and Baltimore, "αβ-lineage-specific Expression of the α T-Cell Receptor Gene by Nearby Silencers," *Cell*, 59:649, 1989.

WO 84/03564

WO 90/07641, 1990

Wong et al., "Appearance of b-lactamase activity in animal cells upon liposome mediated gene transfer", *Gene*, 10:87–94, 1980.

Wu and Wallace, "The ligation amplification reaction (LAR)—amplification of specific DNA sequences using sequential rounds of template-dependent ligation," *Genomics*, 4:560, 1989.

Wu and Wu, "Evidence for targeted gene delivery to HepG2 hepatoma cells in vitro" *Biochemistry*, 27:887–892, 1988.

Wu and Wu, "Receptor-mediated in vitro gene transfections by a soluble DNA carrier system", *J. Biol. Chem.*, 262: 4429–4432, 1987.

Wu and Wu, *Adv. Drug Delivery Rev.*, 12:159–167, 1993.

Yamauchi-Takihara, Sole, Liew, Ing, Liew, "Characterization of human cardiac myosin heavy chain genes," *Proc. Nat'l Acad. Sci. USA*, 86(10):3504–8, 1989.

Yang, Burkholder, Roberts, Martinell and McCabe, "In vivo and in vitro gene transfer to mammalian somatic cells by particle bombardment," *Proc Nat'l Acad. Sci. USA*, 87:9568–9572, 1990.

Yutzey, Kline, and Konieczny, "An Internal Regulatory Element Controls Troponin I Gene Expression," *Mol. Cell. Biol.*, 9:1397, 1989.

Zelenin et al., "High-velocity mechanical DNA transfer of the chloramphenicol acetyltransferase gene into rodent liver, kidney and mammary gland cells in organ explants and in vivo", *FEBS Lett.*, 280:94–96, 1991.

Zhang, Wang, Montalvo, "Smubp-2 represses the Epstein-Bar virus lytic switch promoter," *Virology*, 255:160–170, 1999.

Ziober and Kramer, "Identification and characterization of the cell type-specific and developmentally regulated α7 integrin gene promoter," *J. Bio. Chem.*, 271(37):22915–22, 1996.

The invention claimed is:

1. An isolated polynucleotide encoding a polypeptide having the sequence of SEQ ID NO:8.

2. The polynucleotide of claim 1, wherein said polynucleotide has a nucleic acid sequence of SEQ ID NO:7, or a full length complement thereof.

3. The polynucleotide of claim 1, wherein said polynucleotide further comprises a promoter operable in eukaryotic cells.

4. The polynucleotide of claim 3, wherein said promoter is selected from the group consisting of hsp68, SV40, CMV, MKC, GAL4$_{UAS}$, HSV and β-actin.

5. The polynucleotide of claim 3, wherein said promoter is a tissue specific promoter.

6. An expression construct comprising a polynucleotide encoding a polypeptide operably linked to a regulatory sequence, wherein said polypeptide has the sequence of SEQ ID NO:8.

7. The expression construct of claim 6, wherein said regulatory sequence is a tissue specific promoter.

8. The expression construct of claim 7, wherein said promoter is a muscle specific promoter.

9. The expression construct of claim 8, wherein said muscle specific promoter is selected from the group consisting of myosin light chain-2 promoter, alpha actin promoter, troponin 1 promoter, Na$^+$/Ca$^{2+}$ exchanger promoter, dystrophin promoter, creatine kinase promoter, alpha7 integrin promoter, brain natriuretic peptide promoter, alpha B-crystallin/small heat shock protein promoter, alpha myosin heavy chain promoter and atrial natriuretic factor promoter.

10. The expression vector of claim 6, wherein said regulatory sequence is an inducible promoter.

11. The expression construct of claim 6, wherein said expression construct is contained in a viral vector.

12. The expression construct of claim 11, wherein said viral vector is selected from the group consisting of a retroviral vector, an adenoviral vector, and adeno-associated viral vector, a vaccinia viral vector, a herpesviral vector, a polyoma viral construct or a Sindbis viral vector.

13. The expression construct of claim 6, wherein said expression construct comprises a polyadenylation signal.

14. The expression construct of claim 6, wherein said expression construct comprises a second polynucleotide encoding a second polypeptide.

15. The expression construct of claim 14, wherein said second polynucleotide is under the control of a second regulatory sequence.

16. The expression construct of claim 6, wherein said polynucleotide has a nucleic acid sequence of SEQ ID NO:7.

* * * * *

UNITED STATES PATENT AND TRADEMARK OFFICE
CERTIFICATE OF CORRECTION

PATENT NO. : 7,160,720 B1  Page 1 of 1
APPLICATION NO. : 10/077583
DATED : January 9, 2007
INVENTOR(S) : Olson et al.

It is certified that error appears in the above-identified patent and that said Letters Patent is hereby corrected as shown below:

In claim 10, column 104, line 21, delete "vector" and insert --construct-- therefor.

Signed and Sealed this

Twenty-ninth Day of May, 2007

JON W. DUDAS
*Director of the United States Patent and Trademark Office*

SEQUENCE LISTING

<160> NUMBER OF SEQ ID NOS: 8

<210> SEQ ID NO 1
<211> LENGTH: 2029
<212> TYPE: DNA
<213> ORGANISM: Mus musculus

<400> SEQUENCE: 1

```
cagtccatga ccaaggtaac cagaaatgac agccagtcca tcaccaacat catcagaaat      60
gatggacagt ccatcaccaa cgtcaccaga aatgacgggc agcccatcac caaggtaacc     120
agaaataaca gccagtcaat caccaacatc accagaaatg acgggcagcc catcaccaag     180
aacaagaaaa cagtgaagga ccaaactaaa cacacaacag aggaaaggca cgtgggtacc     240
acggaccagc cagagaaggc ttcctccact gcagagacta tggatgaaat ccagatccca     300
aaagcacgag ataaggagtt cttcaaccca gtgctcaatg aaaaccaaaa gctgaccgtg     360
aggaggatcc tgagtggcga ctgccggcct ctcccatata tccctttttgg acctccggga     420 actggaaaga ctgtgactat aatcgaggct gttttgcagg tacattatgc tttgccggac     480
agtcggattt tggtctgcgc tccttccaac agtgctgctg accttgtgtg tttgcgactt     540
catgagagca aggtgctgaa gccagctgcc atggtccggg tgaatgccac ctgcagattt     600
gaagagacta ttattgatgc catcaaaccg tattgcagag atggagaaga tatctggaga     660
gcctcacgct tcaggataat aatcactaca tgtagcagtg caggactgtt ttaccaaata     720
ggagtgagag ttgatactt cacacatgta tttgtggacg aggcaggaca ggcaagtgag     780
ccagaatgcc ttattccttt gggactgatt tcagacatca atggccagat cgtgcttgct     840
ggagacccca tgcagctcgg cccagtcatc aagtccaggc tggccatggc ctatgggttg     900
aatgtgtcca tgttggagag gctgatgtcc agaccagcgt acctgagaga cgaaaatgcc     960
tttggcgctt gcggtgcata taccccattg ttggtcacaa agcttgtgaa gaactacagg    1020
tcccactcgg ctctgctggc actgcccta cgcctgttct accataggga gcttgaggtc    1080
```

-continued

```
tgtgctgatc ccaaagtagt gacttcactg ctgggctggg agaagctgcc cagaaaaggc    1140
ttccctctca tcttccatgg agtgagggg aacgaggctc gtgaaggag aagcccatcg      1200 tggttcagcc cagccgaggc tgtccaggtc atgcgctact gttgcctctt ggcccggagt    1260
gtctccagtc aagtgtcttc caaggatata ggtgtcatca caccctatcg aagcaggtg     1320 gaaaaaataa aaatccttct gcgaaatgtg gatttgactg acataaaggt tggctcggta    1380
gaggagttcc agggacaaga gtacctggtc atcgtcatct ccactgtgcg gtcaaatgaa    1440
gatagatttg aagatgaccg ttatttttg ggtttcttgt ccaattcaaa aagatttaat     1500
gttgcaatca caagacccaa agcactgctg atcattctgg gaaaccctca tgtgcttgtc    1560
agagatccct gttttggagc gctgctagaa tacagtgtta gcaatggtgt ctacacaggg    1620
tgtgatctgc tcctgaact ccaggctctc caaaagtgag cactccagtc cacttcctaa     1680
aaggtaaagc accgtggagg aaagagtgtg gctccacgtg ttcaccttaa gcaggctgtg    1740
gctagacagc tgtgccagga cctgtggaca tggtggagtc tgctacaaca gggagccatt    1800
gagcctcacc ctatgggcca ttagtccagc catgcttcag tcttctgtga ctcctgcggc    1860
ttcctggtct caagactgaa tgttggtatg catgggacca ctgagtcagc tgggctgctc    1920
ctgcttcctt ggactgacct tggttcctaa cagttagttt ctgcctgtgg gcaatcactg    1980
ccactacact cccccaaata aacacttcca taacccagaa aaaaaaaa                 2029
```

<210> SEQ ID NO 2
<211> LENGTH: 550
<212> TYPE: PRT
<213> ORGANISM: Mus musculus

<400> SEQUENCE: 2

```
Met Thr Lys Val Thr Arg Asn Asp Ser Gln Ser Ile Thr Asn Ile Ile
  1               5                  10                  15

Arg Asn Asp Gly Gln Ser Ile Thr Asn Val Thr Arg Asn Asp Gly Gln
             20                  25                  30

Pro Ile Thr Lys Val Thr Arg Asn Asn Ser Gln Ser Ile Thr Asn Ile
         35                  40                  45

Thr Arg Asn Asp Gly Gln Pro Ile Thr Lys Asn Lys Thr Val Lys
     50                  55                  60

Asp Gln Thr Lys His Thr Thr Glu Glu Arg His Val Gly Thr Thr Asp
 65                  70                  75                  80

Gln Pro Glu Lys Ala Ser Ser Thr Ala Glu Thr Met Asp Glu Ile Gln
                 85                  90                  95

Ile Pro Lys Ala Arg Asp Lys Glu Phe Phe Asn Pro Val Leu Asn Glu
            100                 105                 110

Asn Gln Lys Leu Thr Val Arg Arg Ile Leu Ser Gly Asp Cys Arg Pro
        115                 120                 125

Leu Pro Tyr Ile Pro Phe Gly Pro Pro Gly Thr Gly Lys Thr Val Thr
    130                 135                 140

Ile Ile Glu Ala Val Leu Gln Val His Tyr Ala Leu Pro Asp Ser Arg
145                 150                 155                 160

Ile Leu Val Cys Ala Pro Ser Asn Ser Ala Ala Asp Leu Val Cys Leu
                165                 170                 175

Arg Leu His Glu Ser Lys Val Leu Lys Pro Ala Ala Met Val Arg Val
            180                 185                 190

Asn Ala Thr Cys Arg Phe Glu Glu Thr Ile Ile Asp Ala Ile Lys Pro
        195                 200                 205
```

| | | | | | | | | | | | | |
|---|---|---|---|---|---|---|---|---|---|---|---|---|
|Tyr|Cys|Arg|Asp|Gly|Glu|Asp|Ile|Trp|Arg|Ala|Ser|Arg|Phe|Arg|Ile|
| |210| | | | |215| | | | |220| | | | |

Tyr Cys Arg Asp Gly Glu Asp Ile Trp Arg Ala Ser Arg Phe Arg Ile
    210                 215                 220

Ile Ile Thr Thr Cys Ser Ser Ala Gly Leu Phe Tyr Gln Ile Gly Val
225                 230                 235                 240

Arg Val Gly Tyr Phe Thr His Val Phe Val Asp Glu Ala Gly Gln Ala
                245                 250                 255

Ser Glu Pro Glu Cys Leu Ile Pro Leu Gly Leu Ile Ser Asp Ile Asn
            260                 265                 270

Gly Gln Ile Val Leu Ala Gly Asp Pro Met Gln Leu Gly Pro Val Ile
        275                 280                 285

Lys Ser Arg Leu Ala Met Ala Tyr Gly Leu Asn Val Ser Met Leu Glu
    290                 295                 300

Arg Leu Met Ser Arg Pro Ala Tyr Leu Arg Asp Glu Asn Ala Phe Gly
305                 310                 315                 320

Ala Cys Gly Ala Tyr Asn Pro Leu Leu Val Thr Lys Leu Val Lys Asn
                325                 330                 335

Tyr Arg Ser His Ser Ala Leu Leu Ala Leu Pro Ser Arg Leu Phe Tyr
            340                 345                 350

His Arg Glu Leu Glu Val Cys Ala Asp Pro Lys Val Val Thr Ser Leu
        355                 360                 365

Leu Gly Trp Glu Lys Leu Pro Arg Lys Gly Phe Pro Leu Ile Phe His
370                 375                 380

Gly Val Arg Gly Asn Glu Ala Arg Glu Gly Arg Ser Pro Ser Trp Phe
385                 390                 395                 400

Ser Pro Ala Glu Ala Val Gln Val Met Arg Tyr Cys Cys Leu Leu Ala
                405                 410                 415

Arg Ser Val Ser Ser Gln Val Ser Ser Lys Asp Ile Gly Val Ile Thr
            420                 425                 430

Pro Tyr Arg Lys Gln Val Glu Lys Ile Lys Ile Leu Leu Arg Asn Val
        435                 440                 445

Asp Leu Thr Asp Ile Lys Val Gly Ser Val Glu Glu Phe Gln Gly Gln
450                 455                 460

Glu Tyr Leu Val Ile Val Ile Ser Thr Val Arg Ser Asn Glu Asp Arg
465                 470                 475                 480

Phe Glu Asp Asp Arg Tyr Phe Leu Gly Phe Leu Ser Asn Ser Lys Arg
                485                 490                 495

Phe Asn Val Ala Ile Thr Arg Pro Lys Ala Leu Leu Ile Ile Leu Gly
            500                 505                 510

Asn Pro His Val Leu Val Arg Asp Pro Cys Phe Gly Ala Leu Leu Glu
        515                 520                 525

Tyr Ser Val Ser Asn Gly Val Tyr Thr Gly Cys Asp Leu Pro Pro Glu
530                 535                 540

Leu Gln Ala Leu Gln Lys
545                 550

<210> SEQ ID NO 3
<211> LENGTH: 3997
<212> TYPE: DNA
<213> ORGANISM: Mus musculus

<400> SEQUENCE: 3
gaaggtgaca ccaggttgaa aacggtgcag ggcgttgtga caaggtactg cagtgactat    60
ggcatgattg acgacttgat ctacttttcc aatgacgctg tgacgagtaa agtgcttctg   120

-continued

| | |
|---|---|
| aacgtgggac aggaagtcat tgctgtcgtt gaagaaaaca aagtgtcaaa tggactgaaa | 180 |
| gcaatcagag tagaagctgt ctctgacaaa tgggaagatg atagcaaaaa ctctagcaaa | 240 |
| gggttgtcag actccagccc cagagtgctg attggctgtg tgacttccat gttggaaggt | 300 |
| gctggctata tcagccagac cacatacttc tctttggaga gtgtgtgtga aggtttccac | 360 |
| ccatgcaagg gtgactgggt agaggctgag tattggatca ggccagggac atggagcagt | 420 |
| gaggcaatct ctgtgaagcc tctgaggtac aagcgtgtgg acaaggtttg catttccagc | 480 |
| ctgtgtggga ggaacggggt gatagaggac agcatcttct tcagcctgga ctccttgaag | 540 |
| ctgccggaag ggtacatacc gaggagacac gacattgtca atgctgtggt tgtggagagc | 600 |
| agccagtcat gctacatctg gagagcactg tgcatgaccc ctgtgaagag agatgccact | 660 |
| cttggtgagg cccctcagga gccctatgga gcactcttac tgaaaaacaa aggggacatt | 720 |
| gaagttacaa gaatgaccag ttttggaaca ttgaaggaag gagaaagcaa atcaatcgtg | 780 |
| atctggatag agaataaagg gaaggtctct cgggagcttg tcagttgcag actggctaac | 840 |
| tgggataaag cacaccagtt tagatttgag acacagggca gaagcaagtc ctgcccagga | 900 |
| gcggctgctg gtctgttcc tgaaggtgaa aatgttaatt cattgaatca tcacagagaa | 960 |
| gacaaaactg atgagattcc agagagccgt ctggcgaaca gcacagaaat ctctccagat | 1020 |
| ggctgcgctt gtaaagaaga agtagagaa aaaggaaaca cgccagagaa acaggagcca | 1080 |
| gagcctgggg ggctcattcc tccgggggag aagactcaca ttgtggtcac atgcagtgcc | 1140 |
| aaaaaccctg gccgttgcaa ggagctgctt ctgctctgtt tctccgactt tctcattggg | 1200 |
| cggcatcttg aagtgagtgt ggtgagcagc gaggaggccc tgatagctgt gcgtgagccg | 1260 |
| tttcttgga agaagcctaa agctcccaa acattagtgt ctgcaaagac tacagttgtt | 1320 |
| gtaaccacac aaaaaggaa ctcgaggcga caacttccaa gttttcttcc acagtatcca | 1380 |
| ataccagata gacttaaaaa atgtgtggag cagaagattg acatcctgac tttccagccg | 1440 |
| cttcttgcag agctcttgaa catgtcaaac tacaaggaga agttctccac cctgctgtgg | 1500 |
| ctagaggaga tccatgcaga aatcgagctg aaggagtaca acatgagcag agttgtcctc | 1560 |
| aagaggaagg gggatctgct ggtcctggag gtccccgggc tcgcagagag ccggccttcc | 1620 |
| ctctatgcag gtgacaaact gatttttaaaa tctcaagaat acaatggaca tgtcattgaa | 1680 |
| tatatcggct atgtcatgga gattcatgaa gaagatgtaa ctcttaaact taatccagga | 1740 |
| tttgaacaaa tgtataattt tgaacctatg gatgtggagt ttacatacaa tcggaccaca | 1800 |
| agcagacggt gtcactatgc acttgagcag gtcatccatt ggggtgtaaa agtattattt | 1860 |
| ccagaagaaa tcattttaca gtctcctcag gtgacaggga attggagcct gcacaggac | 1920 |
| accaaaaatg atgggcagtc catcaccaac atcaccagaa tgatggaca gtccatgacc | 1980 |
| aagtaaccca gaaatgacag ccagtccatc accaacatca tcagaaatga tggacagtcc | 2040 |
| atcaccaacg tcaccagaaa tgacgggcag cccatcacca aggtaaccag aaataacagc | 2100 |
| cagtcaatca ccaacatcac cagaaatgac gggcagccca tcaccaagaa caagaaaaca | 2160 |
| gtgaaggacc aaactaaaca cacaacagag gaaaggcacg tgggtaccac ggaccagcca | 2220 |
| gagaaggctt cctccactgc agagactatg gatgaaatcc agatcccaaa agcacgagat | 2280 |
| aaggagttct tcaacccagt gctcaatgaa aaccaaaagc tgaccgtgag gaggatcctg | 2340 |
| agtggcgact gccggcctct cccatatatc cctttggac ctccgggaac tggaaagact | 2400 |
| gtgactataa tcgaggctgt tttgcaggta cattatgctt tgccggacag tcggattttg | 2460 |
| gtctgcgctc cttccaacag tgctgctgac cttgtgtgtt tgcgacttca tgagagcaag | 2520 |

-continued

```
gtgctgaagc cagctgccat ggtccgggtg aatgccacct gcagatttga agagactatt    2580
attgatgcca tcaaaccgta ttgcagagat ggagaagata tctggagagc ctcacgcttc    2640
aggataataa tcactacatg tagcagtgca ggactgtttt accaaatagg agtgagagtt    2700
ggatacttca cacatgtatt tgtggacgag gcaggacagg caagtgagcc agaatgcctt    2760
attcctttgg gactgatttc agacatcaat ggccagatcg tgcttgctgg agaccccatg    2820
cagctcggcc cagtcatcaa gtccaggctg ccatggcct atgggttgaa tgtgtccatg    2880
ttggagaggc tgatgtccag accagcgtac ctgagagacg aaaatgcctt ggcgcttgc     2940 ggtgcatata acccattgtt ggtcacaaag cttgtgaaga actacaggtc ccactcggct    3000
ctgctggcac tgccctcacg cctgttctac cataggagc ttgaggtctg tgctgatccc     3060
aaagtagtga cttcactgct gggctgggag aagctgccca gaaaaggctt ccctctcatc    3120
ttccatggag tgagggggaa cgaggctcgt gaagggagaa gcccatcgtg gttcagccca    3180
gccgaggctg tccaggtcat gcgctactgt tgcctcttgg cccggagtgt ctccagtcaa    3240
gtgtcttcca aggatatagg tgtcatcaca ccctatcgga agcaggtgga aaaaataaaa    3300
atccttctgc gaaatgtgga tttgactgac ataaaggttg gctcggtaga ggagttccag    3360
ggacaagagt acctggtcat cgtcatctcc actgtgcggt caaatgaaga tagatttgaa    3420
gatgaccgtt attttttggg tttcttgtcc aattcaaaaa gatttaatgt tgcaatcaca    3480
agacccaaag cactgctgat cattctggga accctcatg tgcttgtcag agatccctgt     3540
tttggagcgc tgctagaata cagtgttagc aatggtgtct acacagggtg tgatctgcct    3600
cctgaactcc aggctctcca aaagtgagca ctccagtcca cttcctaaaa ggtaaagcac    3660
cgtggaggaa agagtgtggc tccacgtgtt caccttaagc aggctgtggc tagacagctg    3720
tgccaggacc tgtggacatg gtggagtctg ctacaacagg gagccattga gcctcaccct    3780
atgggccatt agtccagcca tgcttcagtc ttctgtgact cctgcggctt cctggtctca    3840
agactgaatg ttggtatgca tgggaccact gagtcagctg ggctgctcct gcttccttgg    3900
actgaccttg gttcctaaca gttagtttct gcctgtgggc aatcactgcc actacactcc    3960
cccaaataaa cacttccata accccagaaa aaaaaaa                             3997
```

```
<210> SEQ ID NO 4
<211> LENGTH: 1208
<212> TYPE: PRT
<213> ORGANISM: Mus musculus

<400> SEQUENCE: 4
```

Glu Gly Asp Thr Arg Leu Lys Thr Val Gln Gly Val Val Thr Arg Tyr
 1               5                  10                  15

Cys Ser Asp Tyr Gly Met Ile Asp Asp Leu Ile Tyr Phe Ser Asn Asp
            20                  25                  30

Ala Val Thr Ser Lys Val Leu Leu Asn Val Gly Gln Glu Val Ile Ala
        35                  40                  45

Val Val Glu Glu Asn Lys Val Ser Asn Gly Leu Lys Ala Ile Arg Val
    50                  55                  60

Glu Ala Val Ser Asp Lys Trp Glu Asp Ser Lys Asn Ser Ser Lys
65                  70                  75                  80

Gly Leu Ser Asp Ser Ser Pro Arg Val Leu Ile Gly Cys Val Thr Ser
                85                  90                  95

Met Leu Glu Gly Ala Gly Tyr Ile Ser Gln Thr Thr Tyr Phe Ser Leu
            100                 105                 110

-continued

```
Glu Ser Val Cys Glu Gly Phe His Pro Cys Lys Gly Asp Trp Val Glu
            115                 120                 125
Ala Glu Tyr Trp Ile Arg Pro Gly Thr Trp Ser Ser Glu Ala Ile Ser
        130                 135                 140
Val Lys Pro Leu Arg Tyr Lys Arg Val Asp Lys Val Cys Ile Ser Ser
145                 150                 155                 160
Leu Cys Gly Arg Asn Gly Val Ile Glu Asp Ser Ile Phe Phe Ser Leu
                165                 170                 175
Asp Ser Leu Lys Leu Pro Glu Gly Tyr Ile Pro Arg Arg His Asp Ile
            180                 185                 190
Val Asn Ala Val Val Glu Ser Ser Gln Ser Cys Tyr Ile Trp Arg
        195                 200                 205
Ala Leu Cys Met Thr Pro Val Lys Arg Asp Ala Thr Leu Gly Glu Ala
            210                 215                 220
Pro Gln Glu Pro Tyr Gly Ala Leu Leu Leu Lys Asn Lys Gly Asp Ile
225                 230                 235                 240
Glu Val Thr Arg Met Thr Ser Phe Gly Thr Leu Lys Glu Gly Glu Ser
                245                 250                 255
Lys Ser Ile Val Ile Trp Ile Glu Asn Lys Gly Lys Val Ser Arg Glu
            260                 265                 270
Leu Val Ser Cys Arg Leu Ala Asn Trp Asp Lys Ala His Gln Phe Arg
        275                 280                 285
Phe Glu Thr Gln Gly Arg Ser Lys Ser Cys Pro Gly Ala Ala Ala Gly
        290                 295                 300
Ser Val Pro Glu Gly Glu Asn Val Asn Ser Leu Asn His His Arg Glu
305                 310                 315                 320
Asp Lys Thr Asp Glu Ile Pro Glu Ser Arg Leu Ala Asn Ser Thr Glu
                325                 330                 335
Ile Ser Pro Asp Gly Cys Ala Cys Lys Glu Glu Ser Arg Glu Lys Gly
            340                 345                 350
Asn Thr Pro Glu Lys Gln Glu Pro Glu Pro Gly Gly Leu Ile Pro Pro
        355                 360                 365
Gly Glu Lys Thr His Ile Val Val Thr Cys Ser Ala Lys Asn Pro Gly
370                 375                 380
Arg Cys Lys Glu Leu Leu Leu Cys Phe Ser Asp Phe Leu Ile Gly
385                 390                 395                 400
Arg His Leu Glu Val Ser Val Val Ser Ser Glu Glu Ala Leu Ile Ala
                405                 410                 415
Val Arg Glu Pro Phe Ser Trp Lys Lys Pro Lys Ser Ser Gln Thr Leu
            420                 425                 430
Val Ser Ala Lys Thr Thr Val Val Thr Thr Gln Lys Arg Asn Ser
        435                 440                 445
Arg Arg Gln Leu Pro Ser Phe Leu Pro Gln Tyr Pro Ile Pro Asp Arg
        450                 455                 460
Leu Lys Lys Cys Val Glu Gln Lys Ile Asp Ile Leu Thr Phe Gln Pro
465                 470                 475                 480
Leu Leu Ala Glu Leu Leu Asn Met Ser Asn Tyr Lys Glu Lys Phe Ser
                485                 490                 495
Thr Leu Leu Trp Leu Glu Glu Ile His Ala Glu Ile Glu Leu Lys Glu
            500                 505                 510
Tyr Asn Met Ser Arg Val Val Leu Lys Arg Lys Gly Asp Leu Leu Val
        515                 520                 525
```

-continued

```
Leu Glu Val Pro Gly Leu Ala Glu Ser Arg Pro Ser Leu Tyr Ala Gly
    530                 535                 540

Asp Lys Leu Ile Leu Lys Ser Gln Glu Tyr Asn Gly His Val Ile Glu
545                 550                 555                 560

Tyr Ile Gly Tyr Val Met Glu Ile His Glu Glu Asp Val Thr Leu Lys
                565                 570                 575

Leu Asn Pro Gly Phe Glu Gln Met Tyr Asn Phe Glu Pro Met Asp Val
            580                 585                 590

Glu Phe Thr Tyr Asn Arg Thr Thr Ser Arg Arg Cys His Tyr Ala Leu
        595                 600                 605

Glu Gln Val Ile His Leu Gly Val Lys Val Leu Phe Pro Glu Glu Ile
    610                 615                 620

Ile Leu Gln Ser Pro Gln Val Thr Gly Asn Trp Ser Leu Ala Gln Asp
625                 630                 635                 640

Thr Lys Asn Asp Gly Gln Ser Ile Thr Asn Ile Thr Arg Asn Asp Gly
                645                 650                 655

Gln Ser Met Thr Lys Val Thr Arg Asn Asp Ser Gln Ser Ile Thr Asn
            660                 665                 670

Ile Ile Arg Asn Asp Gly Gln Ser Ile Thr Asn Val Thr Arg Asn Asp
        675                 680                 685

Gly Gln Pro Ile Thr Lys Val Thr Arg Asn Asn Ser Gln Ser Ile Thr
    690                 695                 700

Asn Ile Thr Arg Asn Asp Gly Gln Pro Ile Thr Lys Asn Lys Lys Thr
705                 710                 715                 720

Val Lys Asp Gln Thr Lys His Thr Thr Glu Arg His Val Gly Thr
                725                 730                 735

Thr Asp Gln Pro Glu Lys Ala Ser Ser Thr Ala Glu Thr Met Asp Glu
            740                 745                 750

Ile Gln Ile Pro Lys Ala Arg Asp Lys Glu Phe Phe Asn Pro Val Leu
        755                 760                 765

Asn Glu Asn Gln Lys Leu Thr Val Arg Arg Ile Leu Ser Gly Asp Cys
    770                 775                 780

Arg Pro Leu Pro Tyr Ile Pro Phe Gly Pro Gly Thr Gly Lys Thr
785                 790                 795                 800

Val Thr Ile Ile Glu Ala Val Leu Gln Val His Tyr Ala Leu Pro Asp
                805                 810                 815

Ser Arg Ile Leu Val Cys Ala Pro Ser Asn Ser Ala Ala Asp Leu Val
            820                 825                 830

Cys Leu Arg Leu His Glu Ser Lys Val Leu Lys Pro Ala Ala Met Val
        835                 840                 845

Arg Val Asn Ala Thr Cys Arg Phe Glu Glu Thr Ile Ile Asp Ala Ile
    850                 855                 860

Lys Pro Tyr Cys Arg Asp Gly Glu Asp Ile Trp Arg Ala Ser Arg Phe
865                 870                 875                 880

Arg Ile Ile Ile Thr Thr Cys Ser Ser Ala Gly Leu Phe Tyr Gln Ile
                885                 890                 895

Gly Val Arg Val Gly Tyr Phe Thr His Val Phe Val Asp Glu Ala Gly
            900                 905                 910

Gln Ala Ser Glu Pro Glu Cys Leu Ile Pro Leu Gly Leu Ile Ser Asp
        915                 920                 925

Ile Asn Gly Gln Ile Val Leu Ala Gly Asp Pro Met Gln Leu Gly Pro
    930                 935                 940

Val Ile Lys Ser Arg Leu Ala Met Ala Tyr Gly Leu Asn Val Ser Met
```

-continued

```
                945                 950                 955                 960
Leu Glu Arg Leu Met Ser Arg Pro Ala Tyr Leu Arg Asp Glu Asn Ala
                965                 970                 975
Phe Gly Ala Cys Gly Ala Tyr Asn Pro Leu Leu Val Thr Lys Leu Val
                980                 985                 990
Lys Asn Tyr Arg Ser His Ser Ala Leu Leu Ala Leu Pro Ser Arg Leu
                995                 1000                1005
Phe Tyr His Arg Glu Leu Glu Val Cys Ala Asp Pro Lys Val Val Thr
    1010                1015                1020
Ser Leu Leu Gly Trp Glu Lys Leu Pro Arg Lys Gly Phe Pro Leu Ile
1025                1030                1035                1040
Phe His Gly Val Arg Gly Asn Glu Ala Arg Glu Gly Arg Ser Pro Ser
                1045                1050                1055
Trp Phe Ser Pro Ala Glu Ala Val Gln Val Met Arg Tyr Cys Cys Leu
                1060                1065                1070
Leu Ala Arg Ser Val Ser Ser Gln Val Ser Ser Lys Asp Ile Gly Val
            1075                1080                1085
Ile Thr Pro Tyr Arg Lys Gln Val Glu Lys Ile Lys Ile Leu Leu Arg
    1090                1095                1100
Asn Val Asp Leu Thr Asp Ile Lys Val Gly Ser Val Glu Glu Phe Gln
1105                1110                1115                1120
Gly Gln Glu Tyr Leu Val Ile Val Ile Ser Thr Val Arg Ser Asn Glu
                1125                1130                1135
Asp Arg Phe Glu Asp Asp Arg Tyr Phe Leu Gly Phe Leu Ser Asn Ser
            1140                1145                1150
Lys Arg Phe Asn Val Ala Ile Thr Arg Pro Lys Ala Leu Leu Ile Ile
        1155                1160                1165
Leu Gly Asn Pro His Val Leu Val Arg Asp Pro Cys Phe Gly Ala Leu
    1170                1175                1180
Leu Glu Tyr Ser Val Ser Asn Gly Val Tyr Thr Gly Cys Asp Leu Pro
1185                1190                1195                1200
Pro Glu Leu Gln Ala Leu Gln Lys
            1205
```

<210> SEQ ID NO 5
<211> LENGTH: 4367
<212> TYPE: DNA
<213> ORGANISM: Homo sapiens

<400> SEQUENCE: 5

| | | | | | |
|---|---|---|---|---|---|
| atgacgtcac | tcccaccagg | cacctcgcct | tgtcaggagc | tgccaggcgc | caaccgccga | 60 |
| cctctgaccg | ctacgggtcc | cggctcgcgc | aacgacccca | aggcgcatgc | ccaggcgcgg | 120 |
| cgacccatt | ggtggcgggc | ggcgggagcg | gcgcgggcgc | gtgcgggcgg | cggcagcggc | 180 |
| ggtgacggca | gcctaggccg | ggcgagggcc | atgctgagcc | tcgcagccaa | gctggtggcc | 240 |
| ttcttctgga | ggacggcgga | cacccctagg | aggaagccg | ggcagctgga | gcccgagctc | 300 |
| gcggaaggtg | gcttccgacc | ccacagcatc | ccgccgctct | gggcgcccgt | cctctgtgag | 360 |
| gtctctccgg | tgacaccagc | ccctcttccc | gccctcactt | tgtgtgttta | cgccgagcag | 420 |
| ctgccaagtc | gtctctccat | gtcgttcctc | cctgtccgca | gcgtcattgg | cggtggtgac | 480 |
| actaagctga | aaactgtacg | gggtgtcgtg | acaaggtact | gcagcgatta | tggcatgatt | 540 |
| gatgatatga | tctacttctc | cagtgatgct | gtgactagca | gagtgcttct | gaatgttgga | 600 |
| caggaagtga | ttgcagttgt | ggaagaaaat | aaagtgtcca | atggactgaa | agcaatcagg | 660 |

-continued

```
gtagaagctg tctctgataa gtgggaagac gacagcagaa accatgggag tccctcagac    720
tgcggccccc gagtgttgat tggctgtgtg acttccctgg tggagggcgc aggctgtatc    780
agtcagacca cctacttctc tctggagagt gtgtgcgaag gtttcgagcc ctgcaaggga    840
gactgggtgg aggctgagta ccggatccgg cctggcacgt ggagcagcga agccacctca    900
gtgaagccac tgagatacaa gcgcgtggac aaggtctgca tctctagcct ctgtggaagg    960
aacgggtgt  tagaggaaag catcttcttt accttggact ccttgaaact gccagatggg   1020
tacacacccc ggagaggtga cgtggtcaat gcagtggtgg tggagagcag ccagtcatgc   1080
tatgtctgga gggcactttg tatgacccta gtgaagaggc gggacgccgc ccctgttcat   1140
gaggccactc atttctatgg aacgattttg ctgaagaaca aggtgatat  tgaagttaca   1200
caggtgacgc attttggaac cctaaaggaa ggaagaagta aaaccatggt gatctggata   1260
gagaataaag gagacattcc tcaaaactta gtcagctgta aactggctgg ctgggataaa   1320
tctaaacaat tcagattcca aatgctggat aaagaccaga tgtgcccgt  ggtatctttt   1380
gtttctgttc ctgagaagga gaattcatca gatgaaaata ttaattcatt aaatagccac   1440
acaaaaaaca aacctctca  gatgtcggag agcagtttgg tgaacaacag aggaatctct   1500
ccaggtagtg gacgtttcgg ctgtcactgc gtgaggtcgg gtgattgtac ctgtaaagga   1560
gaaaatggag aaaaagacaa cattctatca aggaagcaga tgacagagcc tgagcctggg   1620
gggcttgtcc ctccagggg  aaaaaccttc attgtggtca tctgtgacgg aaagaatcct   1680
ggccgctgca aggagctcct tttgctctgt ttttccgatt tcctaattgg gcgataccct   1740
gaagtaaatg ttatcagtgg ggaggagtca ctaattgctg cgcgcgaacc attttcttgg   1800
aaaaagctta aagttcaca  agcgttaaca tccgcaaaaa ctacagttgt tgtgaccgca   1860
cagaaaagga actcaagacg acaacttcca agttttcttc cccaatatcc aatcccagat   1920
agacttagaa aatgtgtgga acaaaaaatt gacatcctga cttccagcc  attacttgca   1980
gagcttctga acatgtcaaa ttacaaggag aagttttcga ctttgctgtg cttgaggag   2040
atttatgcag aaatggaact gaaagagtat aacatgagcg ggatcatctt aagaaggaat   2100
ggggatctgc tggttctgga ggtcccaggg ttggccgaag ggaggccttc tctctacgca   2160
ggtgataaac tgattttaaa aactcaagag tacaatggac atgccatcga atacatcagc   2220
tacgtgactg agattcatga agaagatgta actcttaaaa ttaatccaga atttgaacaa   2280
gcctataact ttgaacctat ggatgtggaa tttacatata ataggaccac aagcagacgg   2340
tgtcactttg cacttgaaca cgtcatccac ttaggtgtaa agtgttgtt  tccagaagaa   2400
attatttac  agtctccaca agtgacggga aattggaacc atgcacaaga caccaaaagc   2460
agtggacagt ccaccagcaa aaagaatagg aaaacaatga cggaccaagc tgagcatgga   2520
acagaggaga ggcgtgttgg tgacaaggac ctgccggtgc tggcacccct tactgcagag   2580
atgagcgatt gggtagatga aattcagacc cctaaagcaa gaaagatgga gttttcaac   2640
ccagtgctaa atgaaaatca gaagttagca gttaaaagga ttctgagtgg tgactgccgt   2700
cccctcccgt atattctctt tggacctcct ggtactggaa agacagtgac aataatagag   2760
gctgttttac aggtacactt tgccttgccg gacagtcgga ttttagtctg tgcgccctcc   2820
aacagtgctg ctgacctcgt gtgtctgcgg ctgcacgaga gcaaggtgct acagccggcc   2880
accatggtcc gggtgaacgc cacctgcagg ttcgaggaga tagttattga cgccgtcaaa   2940
ccgtattgca gagacggaga agacatctgg aaagcctcac gcttccggat aatcatcacc   3000
```

-continued

```
acatgcagca gctcagggct gttttaccaa ataggagtga gagttgggca cttcactcac  3060
gtgtttgtgg acgaggctgg gcaggcaagt gagccggaat gcctcattcc tctgggctg   3120
atgtcggaca tcagtggcca gatcgtgctg gcaggagacc ccatgcagct cggcccagtc  3180
attaagtcca gactcgccat ggcctatggg ctgaacgtgt cctttttgga acggctgatg  3240
tctcgacccg cgtaccagag ggacgaaaat gctttcggtg cttgtggcgc acataatccc  3300
ctgttggtca caaagctggt gaagaactac cggtcccacg aggccctgct gatgctgccc  3360
tcacggctgt tctaccacag ggaactcgag gtctgtgcgg accccacagt ggtgacctcc  3420
ttgctgggct gggagaagtt gcctaagaaa ggcttccctc tcatcttcca tggtgtgcgg  3480
ggcagcgagg cacgggaggg aaaaagccca tcgtggttca acccggccga ggccgtccag  3540
gtcctgcgct actgctgcct cctggcccac agcatctcca gtcaggtgtc tgccagcgac  3600
attggcgtca tcacgcccta ccggaagcag gtggagaaaa tcagaattct tttgcgtaat  3660
gttgatctga tggatataaa ggttggatca gtagaggagt tcaaggaca agagtatctg   3720
gtcatcatca tttcgaccgt acggtcaaat gaagatagat ttgaagatga tcgatatttt  3780
ttgggttct tgtccaactc aaaaagattt aatgttgcaa tcaccagacc caaagctttg   3840
ctgatagtgc tgggaaaccc ccatgttctc gttcgagacc cctgttttgg tgctttgctg   3900
gaatacagta ttacaaacgg tgtttacatg ggatgcgatt tacctcctgc actgcagtct  3960
ctgcaaaact gtggcgaggg ggtggcagac ccctcctacc cagtggtgcc agaatccaca  4020
ggaccagaga agcatcagga gcccagctga tctgcagtgg ctgacagcag ggaggccatg  4080
tgctcagcct ggccacgttg ccgttacagt ctgctccgtg gctcctgtgg cctgcccttg   4140
tctcgcagcc aggcagggtc gtgtgtgggt gtggggctgc caggttggac gcagctgctg   4200
ctgccctgac tttggcatat gccagcctgt tcctgccaca gggcagtcac tgccgcctac  4260
cctgaaataa accctcgagt gaccccccaga aaaaaaaaaa aaaaaaaaaa aaaaaaaaa  4320
ggggcggccg ttctagagga tccaaaaaaa aaaaaaaaaa aaaagg               4367
```

<210> SEQ ID NO 6
<211> LENGTH: 1349
<212> TYPE: PRT
<213> ORGANISM: Homo sapiens

<400> SEQUENCE: 6

```
Met Thr Ser Leu Pro Pro Gly Thr Ser Pro Cys Gln Glu Leu Pro Gly
  1               5                  10                  15

Ala Asn Arg Arg Pro Leu Thr Ala Thr Gly Pro Gly Ser Arg Asn Asp
                 20                  25                  30

Pro Lys Ala His Ala Gln Ala Arg Arg Pro His Trp Trp Arg Ala Ala
             35                  40                  45

Gly Ala Ala Arg Ala Arg Ala Gly Gly Ser Gly Gly Asp Gly Ser
         50                  55                  60

Leu Gly Arg Ala Arg Ala Met Leu Ser Leu Ala Ala Lys Leu Val Ala
 65                  70                  75                  80

Phe Phe Trp Arg Thr Ala Asp Thr Pro Arg Glu Ala Gly Gln Leu
                 85                  90                  95

Glu Pro Glu Leu Ala Glu Gly Gly Phe Arg Pro His Ser Ile Pro Pro
            100                 105                 110

Leu Trp Ala Pro Val Leu Cys Glu Val Ser Pro Val Thr Pro Ala Pro
        115                 120                 125

Leu Pro Ala Leu Thr Leu Cys Val Tyr Ala Glu Gln Leu Pro Ser Arg
```

-continued

```
            130                 135                 140
Leu Ser Met Ser Phe Leu Pro Val Arg Ser Val Ile Gly Gly Asp
145                 150                 155                 160
Thr Lys Leu Lys Thr Val Arg Gly Val Val Thr Arg Tyr Cys Ser Asp
                    165                 170                 175
Tyr Gly Met Ile Asp Asp Met Ile Tyr Phe Ser Ser Asp Ala Val Thr
                180                 185                 190
Ser Arg Val Leu Leu Asn Val Gly Gln Glu Val Ile Ala Val Val Glu
                195                 200                 205
Glu Asn Lys Val Ser Asn Gly Leu Lys Ala Ile Arg Val Glu Ala Val
210                 215                 220
Ser Asp Lys Trp Glu Asp Asp Ser Arg Asn His Gly Ser Pro Ser Asp
225                 230                 235                 240
Cys Gly Pro Arg Val Leu Ile Gly Cys Val Thr Ser Leu Val Glu Gly
                245                 250                 255
Ala Gly Cys Ile Ser Gln Thr Thr Tyr Phe Ser Leu Glu Ser Val Cys
                260                 265                 270
Glu Gly Phe Glu Pro Cys Lys Gly Asp Trp Val Glu Ala Glu Tyr Arg
                275                 280                 285
Ile Arg Pro Gly Thr Trp Ser Ser Glu Ala Thr Ser Val Lys Pro Leu
                290                 295                 300
Arg Tyr Lys Arg Val Asp Lys Val Cys Ile Ser Ser Leu Cys Gly Arg
305                 310                 315                 320
Asn Gly Val Leu Glu Glu Ser Ile Phe Phe Thr Leu Asp Ser Leu Lys
                325                 330                 335
Leu Pro Asp Gly Tyr Thr Pro Arg Arg Gly Asp Val Val Asn Ala Val
                340                 345                 350
Val Val Glu Ser Ser Gln Ser Cys Tyr Val Trp Arg Ala Leu Cys Met
                355                 360                 365
Thr Leu Val Lys Arg Arg Asp Ala Ala Pro Val His Glu Ala Thr His
                370                 375                 380
Phe Tyr Gly Thr Ile Leu Leu Lys Asn Lys Gly Asp Ile Glu Val Thr
385                 390                 395                 400
Gln Val Thr His Phe Gly Thr Leu Lys Glu Gly Arg Ser Lys Thr Met
                    405                 410                 415
Val Ile Trp Ile Glu Asn Lys Gly Asp Ile Pro Gln Asn Leu Val Ser
                420                 425                 430
Cys Lys Leu Ala Gly Trp Asp Lys Ser Lys Gln Phe Arg Phe Gln Met
                435                 440                 445
Leu Asp Lys Asp Gln Met Cys Pro Val Val Ser Phe Val Ser Val Pro
450                 455                 460
Glu Lys Glu Asn Ser Ser Asp Glu Asn Ile Asn Ser Leu Asn Ser His
465                 470                 475                 480
Thr Lys Asn Lys Thr Ser Gln Met Ser Glu Ser Ser Leu Val Asn Asn
                    485                 490                 495
Arg Gly Ile Ser Pro Gly Ser Gly Arg Phe Gly Cys His Cys Val Arg
                500                 505                 510
Ser Gly Asp Cys Thr Cys Lys Gly Glu Asn Gly Glu Lys Asp Asn Ile
                515                 520                 525
Leu Ser Arg Lys Gln Met Thr Glu Pro Glu Pro Gly Gly Leu Val Pro
                530                 535                 540
Pro Gly Gly Lys Thr Phe Ile Val Val Ile Cys Asp Gly Lys Asn Pro
545                 550                 555                 560
```

-continued

```
Gly Arg Cys Lys Glu Leu Leu Leu Cys Phe Ser Asp Phe Leu Ile
            565                 570                 575
Gly Arg Tyr Leu Glu Val Asn Val Ile Ser Gly Glu Glu Ser Leu Ile
            580                 585                 590
Ala Ala Arg Glu Pro Phe Ser Trp Lys Lys Leu Lys Ser Ser Gln Ala
            595                 600                 605
Leu Thr Ser Ala Lys Thr Thr Val Val Thr Ala Gln Lys Arg Asn
    610                 615                 620
Ser Arg Arg Gln Leu Pro Ser Phe Leu Pro Gln Tyr Pro Ile Pro Asp
625                 630                 635                 640
Arg Leu Arg Lys Cys Val Glu Gln Lys Ile Asp Ile Leu Thr Phe Gln
                645                 650                 655
Pro Leu Leu Ala Glu Leu Leu Asn Met Ser Asn Tyr Lys Glu Lys Phe
            660                 665                 670
Ser Thr Leu Leu Trp Leu Glu Glu Ile Tyr Ala Glu Met Glu Leu Lys
            675                 680                 685
Glu Tyr Asn Met Ser Gly Ile Ile Leu Arg Arg Asn Gly Asp Leu Leu
    690                 695                 700
Val Leu Glu Val Pro Gly Leu Ala Glu Gly Arg Pro Ser Leu Tyr Ala
705                 710                 715                 720
Gly Asp Lys Leu Ile Leu Lys Thr Gln Glu Tyr Asn Gly His Ala Ile
                725                 730                 735
Glu Tyr Ile Ser Tyr Val Thr Glu Ile His Glu Glu Asp Val Thr Leu
            740                 745                 750
Lys Ile Asn Pro Glu Phe Glu Gln Ala Tyr Asn Phe Glu Pro Met Asp
            755                 760                 765
Val Glu Phe Thr Tyr Asn Arg Thr Thr Ser Arg Arg Cys His Phe Ala
    770                 775                 780
Leu Glu His Val Ile His Leu Gly Val Lys Val Leu Phe Pro Glu Glu
785                 790                 795                 800
Ile Ile Leu Gln Ser Pro Gln Val Thr Gly Asn Trp Asn His Ala Gln
                805                 810                 815
Asp Thr Lys Ser Ser Gly Gln Ser Thr Ser Lys Lys Asn Arg Lys Thr
            820                 825                 830
Met Thr Asp Gln Ala Glu His Gly Thr Glu Glu Arg Arg Val Gly Asp
            835                 840                 845
Lys Asp Leu Pro Val Leu Ala Pro Phe Thr Ala Glu Met Ser Asp Trp
    850                 855                 860
Val Asp Glu Ile Gln Thr Pro Lys Ala Arg Lys Met Glu Phe Phe Asn
865                 870                 875                 880
Pro Val Leu Asn Glu Asn Gln Lys Leu Ala Val Lys Arg Ile Leu Ser
                885                 890                 895
Gly Asp Cys Arg Pro Leu Pro Tyr Ile Leu Phe Gly Pro Pro Gly Thr
            900                 905                 910
Gly Lys Thr Val Thr Ile Ile Glu Ala Val Leu Gln Val His Phe Ala
            915                 920                 925
Leu Pro Asp Ser Arg Ile Leu Val Cys Ala Pro Ser Asn Ser Ala Ala
    930                 935                 940
Asp Leu Val Cys Leu Arg Leu His Glu Ser Lys Val Leu Gln Pro Ala
945                 950                 955                 960
Thr Met Val Arg Val Asn Ala Thr Cys Arg Phe Glu Glu Ile Val Ile
                965                 970                 975
```

-continued

```
Asp Ala Val Lys Pro Tyr Cys Arg Asp Gly Glu Asp Ile Trp Lys Ala
            980                 985                 990
Ser Arg Phe Arg Ile Ile Ile Thr Thr Cys Ser Ser Ser Gly Leu Phe
        995                1000                1005
Tyr Gln Ile Gly Val Arg Val Gly His Phe Thr His Val Phe Val Asp
   1010                1015                1020
Glu Ala Gly Gln Ala Ser Glu Pro Glu Cys Leu Ile Pro Leu Gly Leu
1025                1030                1035                1040
Met Ser Asp Ile Ser Gly Gln Ile Val Leu Ala Gly Asp Pro Met Gln
                1045                1050                1055
Leu Gly Pro Val Ile Lys Ser Arg Leu Ala Met Ala Tyr Gly Leu Asn
            1060                1065                1070
Val Ser Phe Leu Glu Arg Leu Met Ser Arg Pro Ala Tyr Gln Arg Asp
        1075                1080                1085
Glu Asn Ala Phe Gly Ala Cys Gly Ala His Asn Pro Leu Leu Val Thr
   1090                1095                1100
Lys Leu Val Lys Asn Tyr Arg Ser His Glu Ala Leu Leu Met Leu Pro
1105                1110                1115                1120
Ser Arg Leu Phe Tyr His Arg Glu Leu Glu Val Cys Ala Asp Pro Thr
                1125                1130                1135
Val Val Thr Ser Leu Leu Gly Trp Glu Lys Leu Pro Lys Lys Gly Phe
            1140                1145                1150
Pro Leu Ile Phe His Gly Val Arg Gly Ser Glu Ala Arg Glu Gly Lys
        1155                1160                1165
Ser Pro Ser Trp Phe Asn Pro Ala Glu Ala Val Gln Val Leu Arg Tyr
   1170                1175                1180
Cys Cys Leu Leu Ala His Ser Ile Ser Ser Gln Val Ser Ala Ser Asp
1185                1190                1195                1200
Ile Gly Val Ile Thr Pro Tyr Arg Lys Gln Val Glu Lys Ile Arg Ile
                1205                1210                1215
Leu Leu Arg Asn Val Asp Leu Met Asp Ile Lys Val Gly Ser Val Glu
            1220                1225                1230
Glu Phe Gln Gly Gln Glu Tyr Leu Val Ile Ile Ser Thr Val Arg
        1235                1240                1245
Ser Asn Glu Asp Arg Phe Glu Asp Asp Arg Tyr Phe Leu Gly Phe Leu
   1250                1255                1260
Ser Asn Ser Lys Arg Phe Asn Val Ala Ile Thr Arg Pro Lys Ala Leu
1265                1270                1275                1280
Leu Ile Val Leu Gly Asn Pro His Val Leu Val Arg Asp Pro Cys Phe
                1285                1290                1295
Gly Ala Leu Leu Glu Tyr Ser Ile Thr Asn Gly Val Tyr Met Gly Cys
            1300                1305                1310
Asp Leu Pro Pro Ala Leu Gln Ser Leu Gln Asn Cys Gly Glu Gly Val
        1315                1320                1325
Ala Asp Pro Ser Tyr Pro Val Val Pro Glu Ser Thr Gly Pro Glu Lys
   1330                1335                1340
His Gln Glu Pro Ser
1345

<210> SEQ ID NO 7
<211> LENGTH: 1801
<212> TYPE: DNA
<213> ORGANISM: Homo sapiens
<220> FEATURE:
<221> NAME/KEY: CDS
```

<222> LOCATION: (1)..(1551)

<400> SEQUENCE: 7

| | |
|---|---|
| atg acg gac caa gct gag cat gga aca gag gag agg cgt gtt ggt gac<br>Met Thr Asp Gln Ala Glu His Gly Thr Glu Glu Arg Arg Val Gly Asp<br>1                5                  10                15 | 48 |
| aag gac ctg ccg gtg ctg gca ccc ttt act gca gag atg agc gat tgg<br>Lys Asp Leu Pro Val Leu Ala Pro Phe Thr Ala Glu Met Ser Asp Trp<br>                20                  25                  30 | 96 |
| gta gat gaa att cag acc cct aaa gca aga aag atg gag ttt ttc aac<br>Val Asp Glu Ile Gln Thr Pro Lys Ala Arg Lys Met Glu Phe Phe Asn<br>             35                  40                  45 | 144 |
| cca gtg cta aat gaa aat cag aag tta gca gtt aaa agg att ctg agt<br>Pro Val Leu Asn Glu Asn Gln Lys Leu Ala Val Lys Arg Ile Leu Ser<br>50                  55                  60 | 192 |
| ggt gac tgc cgt ccc ctc ccg tat att ctc ttt gga cct cct ggt act<br>Gly Asp Cys Arg Pro Leu Pro Tyr Ile Leu Phe Gly Pro Pro Gly Thr<br>65                  70                  75                  80 | 240 |
| gga aag aca gtg aca ata ata gag gct gtt tta cag gta cac ttt gcc<br>Gly Lys Thr Val Thr Ile Ile Glu Ala Val Leu Gln Val His Phe Ala<br>                85                  90                  95 | 288 |
| ttg ccg gac agt cgg att tta gtc tgt gcg ccc tcc aac agt gct gct<br>Leu Pro Asp Ser Arg Ile Leu Val Cys Ala Pro Ser Asn Ser Ala Ala<br>                100               105               110 | 336 |
| gac ctc gtg tgt ctg cgg ctg cac gag agc aag gtg cta cag ccg gcc<br>Asp Leu Val Cys Leu Arg Leu His Glu Ser Lys Val Leu Gln Pro Ala<br>                115               120               125 | 384 |
| acc atg gtc cgg gtg aac gcc acc tgc agg ttc gag gag ata gtt att<br>Thr Met Val Arg Val Asn Ala Thr Cys Arg Phe Glu Glu Ile Val Ile<br>130                  135               140 | 432 |
| gac gcc gtc aaa ccg tat tgc aga gac gga gaa gac atc tgg aaa gcc<br>Asp Ala Val Lys Pro Tyr Cys Arg Asp Gly Glu Asp Ile Trp Lys Ala<br>145                  150               155               160 | 480 |
| tca cgc ttc cgg ata atc atc acc aca tgc agc agc tca ggg ctg ttt<br>Ser Arg Phe Arg Ile Ile Ile Thr Thr Cys Ser Ser Ser Gly Leu Phe<br>                165               170               175 | 528 |
| tac caa ata gga gtg aga gtt ggg cac ttc act cac gtg ttt gtg gac<br>Tyr Gln Ile Gly Val Arg Val Gly His Phe Thr His Val Phe Val Asp<br>                180               185               190 | 576 |
| gag gct ggg cag gca agt gag ccg gaa tgc ctc att cct ctg ggg ctg<br>Glu Ala Gly Gln Ala Ser Glu Pro Glu Cys Leu Ile Pro Leu Gly Leu<br>                195               200               205 | 624 |
| atg tcg gac atc agt ggc cag atc gtg ctg gca gga gac ccc atg cag<br>Met Ser Asp Ile Ser Gly Gln Ile Val Leu Ala Gly Asp Pro Met Gln<br>210                  215               220 | 672 |
| ctc gga cca gtc att aag tcc aga ctc gcc atg gcc tat ggg ctg aac<br>Leu Gly Pro Val Ile Lys Ser Arg Leu Ala Met Ala Tyr Gly Leu Asn<br>225                  230               235               240 | 720 |
| gtg tcc ttt ttg gaa cgg ctg atg tct cga ccc gcg tac cag agg gac<br>Val Ser Phe Leu Glu Arg Leu Met Ser Arg Pro Ala Tyr Gln Arg Asp<br>                245               250               255 | 768 |
| gaa aat gct ttc ggt gct tgt ggc gca cat aat ccc ctg ttg gtc aca<br>Glu Asn Ala Phe Gly Ala Cys Gly Ala His Asn Pro Leu Leu Val Thr<br>                260               265               270 | 816 |
| aag ctg gtg aag aac tac cgg tcc cac gag gcc ctg ctg atg ctg ccc<br>Lys Leu Val Lys Asn Tyr Arg Ser His Glu Ala Leu Leu Met Leu Pro<br>                275               280               285 | 864 |
| tca cgg ctg ttc tac cac agg gaa ctc gag gtc tgt gcg gac ccc aca<br>Ser Arg Leu Phe Tyr His Arg Glu Leu Glu Val Cys Ala Asp Pro Thr<br>290                  295               300 | 912 |

| | | | | | | | | | | | | | |
|---|---|---|---|---|---|---|---|---|---|---|---|---|---|
| gtg | gtg | acc | tcc | ttg | ctg | ggc | tgg | gag | aag | ttg | cct | aag | aaa | ggc | ttc |
| Val | Val | Thr | Ser | Leu | Leu | Gly | Trp | Glu | Lys | Leu | Pro | Lys | Lys | Gly | Phe |
| 305 | | | | 310 | | | | | 315 | | | | | 320 | |

960 cct ctc atc ttc cat ggt gtg cgg ggc agc gag gca cgg gag gga aaa
Pro Leu Ile Phe His Gly Val Arg Gly Ser Glu Ala Arg Glu Gly Lys
              325                 330                 335

1008 agc cca tcg tgg ttc aac ccg gcc gag gcc gtc cag gtc ctg cgc tac
Ser Pro Ser Trp Phe Asn Pro Ala Glu Ala Val Gln Val Leu Arg Tyr
          340                 345                 350

1056 tgc tgc ctc ctg gcc cac agc atc tcc agt cag gtg tct gcc agc gac
Cys Cys Leu Leu Ala His Ser Ile Ser Ser Gln Val Ser Ala Ser Asp
      355                 360                 365

1104 att ggc gtc atc acg ccc tac cgg aag cag gtg gag aaa atc aga att
Ile Gly Val Ile Thr Pro Tyr Arg Lys Gln Val Glu Lys Ile Arg Ile
370                 375                 380

1152 ctt ttg cgt aat gtt gat ctg atg gat ata aag gtt gga tca gta gag
Leu Leu Arg Asn Val Asp Leu Met Asp Ile Lys Val Gly Ser Val Glu
385                 390                 395                 400

1200 gag ttt caa gga caa gag tat ctg gtc atc atc att tcg acc gta cgg
Glu Phe Gln Gly Gln Glu Tyr Leu Val Ile Ile Ile Ser Thr Val Arg
              405                 410                 415

1248 tca aat gaa gat aga ttt gaa gat gat cga tat ttt ttg ggt ttc ttg
Ser Asn Glu Asp Arg Phe Glu Asp Asp Arg Tyr Phe Leu Gly Phe Leu
          420                 425                 430

1296 tcc aac tca aaa aga ttt aat gtt gca atc acc aga ccc aaa gct ttg
Ser Asn Ser Lys Arg Phe Asn Val Ala Ile Thr Arg Pro Lys Ala Leu
      435                 440                 445

1344 ctg ata gtg ctg gga aac ccc cat gtt ctc gtt cga gac ccc tgt ttt
Leu Ile Val Leu Gly Asn Pro His Val Leu Val Arg Asp Pro Cys Phe
450                 455                 460

1392 ggt gct ttg ctg gaa tac agt att aca aac ggt gtt tac atg gga tgc
Gly Ala Leu Leu Glu Tyr Ser Ile Thr Asn Gly Val Tyr Met Gly Cys
465                 470                 475                 480

1440 gat tta cct cct gca ctg cag tct ctg caa aac tgt ggc gag ggg gtg
Asp Leu Pro Pro Ala Leu Gln Ser Leu Gln Asn Cys Gly Glu Gly Val
              485                 490                 495

1488 gca gac ccc tcc tac cca gtg gtg cca gaa tcc aca gga cca gag aag
Ala Asp Pro Ser Tyr Pro Val Val Pro Glu Ser Thr Gly Pro Glu Lys
          500                 505                 510

1536 cat cag gag ccc agc tgatctgcag tggctgacag cagggaggcc atgtgctcag
His Gln Glu Pro Ser
          515

1591 cctggccacg ttgccgttac agtctgctcc gtggctcctg tggcctgccc ttgtctcgca

1651 gccaggcagg gtcgtgtgtg ggtgtggggc tgccaggttg gacgcagctg ctgctgccct

1711 gactttggca tatgccagcc tgttcctgcc acagggcagt cactgccgcc taccctgaaa

1771 taaaccctcg agtgaccccc aaaaaaaaaa

1801

<210> SEQ ID NO 8
<211> LENGTH: 517
<212> TYPE: PRT
<213> ORGANISM: Homo sapiens

<400> SEQUENCE: 8

Met Thr Asp Gln Ala Glu His Gly Thr Glu Glu Arg Arg Val Gly Asp
1               5                   10                  15

Lys Asp Leu Pro Val Leu Ala Pro Phe Thr Ala Glu Met Ser Asp Trp
            20                  25                  30

-continued

```
Val Asp Glu Ile Gln Thr Pro Lys Ala Arg Lys Met Glu Phe Phe Asn
     35                  40                  45

Pro Val Leu Asn Glu Asn Gln Lys Leu Ala Val Lys Arg Ile Leu Ser
 50                  55                  60

Gly Asp Cys Arg Pro Leu Pro Tyr Ile Leu Phe Gly Pro Pro Gly Thr
 65                  70                  75                  80

Gly Lys Thr Val Thr Ile Ile Glu Ala Val Leu Gln Val His Phe Ala
                 85                  90                  95

Leu Pro Asp Ser Arg Ile Leu Val Cys Ala Pro Ser Asn Ser Ala Ala
                100                 105                 110

Asp Leu Val Cys Leu Arg Leu His Glu Ser Lys Val Leu Gln Pro Ala
            115                 120                 125

Thr Met Val Arg Val Asn Ala Thr Cys Arg Phe Glu Glu Ile Val Ile
    130                 135                 140

Asp Ala Val Lys Pro Tyr Cys Arg Asp Gly Glu Asp Ile Trp Lys Ala
145                 150                 155                 160

Ser Arg Phe Arg Ile Ile Ile Thr Thr Cys Ser Ser Gly Leu Phe
                165                 170                 175

Tyr Gln Ile Gly Val Arg Val Gly His Phe Thr His Val Phe Val Asp
            180                 185                 190

Glu Ala Gly Gln Ala Ser Glu Pro Glu Cys Leu Ile Pro Leu Gly Leu
        195                 200                 205

Met Ser Asp Ile Ser Gly Gln Ile Val Leu Ala Gly Asp Pro Met Gln
    210                 215                 220

Leu Gly Pro Val Ile Lys Ser Arg Leu Ala Met Ala Tyr Gly Leu Asn
225                 230                 235                 240

Val Ser Phe Leu Glu Arg Leu Met Ser Arg Pro Ala Tyr Gln Arg Asp
                245                 250                 255

Glu Asn Ala Phe Gly Ala Cys Gly Ala His Asn Pro Leu Leu Val Thr
            260                 265                 270

Lys Leu Val Lys Asn Tyr Arg Ser His Glu Ala Leu Leu Met Leu Pro
        275                 280                 285

Ser Arg Leu Phe Tyr His Arg Glu Leu Glu Val Cys Ala Asp Pro Thr
    290                 295                 300

Val Val Thr Ser Leu Leu Gly Trp Glu Lys Leu Pro Lys Lys Gly Phe
305                 310                 315                 320

Pro Leu Ile Phe His Gly Val Arg Gly Ser Glu Ala Arg Glu Gly Lys
                325                 330                 335

Ser Pro Ser Trp Phe Asn Pro Ala Glu Ala Val Gln Val Leu Arg Tyr
            340                 345                 350

Cys Cys Leu Leu Ala His Ser Ile Ser Ser Gln Val Ser Ala Ser Asp
        355                 360                 365

Ile Gly Val Ile Thr Pro Tyr Arg Lys Gln Val Glu Lys Ile Arg Ile
    370                 375                 380

Leu Leu Arg Asn Val Asp Leu Met Asp Ile Lys Val Gly Ser Val Glu
385                 390                 395                 400

Glu Phe Gln Gly Gln Glu Tyr Leu Val Ile Ile Ser Thr Val Arg
                405                 410                 415

Ser Asn Glu Asp Arg Phe Glu Asp Arg Tyr Phe Leu Gly Phe Leu
            420                 425                 430

Ser Asn Ser Lys Arg Phe Asn Val Ala Ile Thr Arg Pro Lys Ala Leu
        435                 440                 445

Leu Ile Val Leu Gly Asn Pro His Val Leu Val Arg Asp Pro Cys Phe
```

-continued

```
               450                 455             460
Gly Ala Leu Leu Glu Tyr Ser Ile Thr Asn Gly Val Tyr Met Gly Cys
465                     470                 475             480

Asp Leu Pro Pro Ala Leu Gln Ser Leu Gln Asn Cys Gly Glu Gly Val
                485                 490                 495

Ala Asp Pro Ser Tyr Pro Val Val Pro Glu Ser Thr Gly Pro Glu Lys
                500                 505                 510

His Gln Glu Pro Ser
            515
```